US008053447B2

(12) United States Patent
Ebdrup et al.

(10) Patent No.: US 8,053,447 B2
(45) Date of Patent: Nov. 8, 2011

(54) 11β-HYDROXYSTEROID DEHYDROGENASE TYPE 1 ACTIVE COMPOUNDS

(75) Inventors: Soren Ebdrup, Roskilde (DK); Henrik Sune Andersen, Lyngby (DK)

(73) Assignee: High Point Pharmaceuticals, LLC, High Point, NC (US)

( * ) Notice: Subject to any disclaimer, the term of this patent is extended or adjusted under 35 U.S.C. 154(b) by 304 days.

(21) Appl. No.: 12/294,475

(22) PCT Filed: Mar. 27, 2007

(86) PCT No.: PCT/EP2007/052929

§ 371 (c)(1),
(2), (4) Date: Sep. 25, 2008

(87) PCT Pub. No.: WO2007/115935

PCT Pub. Date: Oct. 18, 2007

(65) Prior Publication Data

US 2010/0292215 A1 Nov. 18, 2010

(30) Foreign Application Priority Data

Apr. 7, 2006 (EP) ..................................... 06112359

(51) Int. Cl.
*A61K 31/445* (2006.01)
*C07D 211/00* (2006.01)

(52) U.S. Cl. ......... 514/315; 514/317; 546/184; 546/192

(58) Field of Classification Search .................. 514/315, 514/317; 546/184, 192
See application file for complete search history.

(56) References Cited

U.S. PATENT DOCUMENTS

| | | | |
|---|---|---|---|
| 2,913,454 | A | 11/1959 | Petersen et al. |
| 3,723,442 | A | 3/1973 | Nakanishi et al. |
| 3,784,551 | A | 1/1974 | Nakanishi et al. |
| 4,350,696 | A | 9/1982 | Cross et al. |
| 4,482,555 | A | 11/1984 | Doria et al. |
| 4,851,423 | A | 7/1989 | Girijavallabhan et al. |
| 4,963,590 | A | 10/1990 | Backstrom et al. |
| 5,001,133 | A | 3/1991 | Richardson et al. |
| 5,049,695 | A | 9/1991 | Abraham et al. |
| 5,112,861 | A | 5/1992 | Backstrom et al. |
| 5,122,539 | A | 6/1992 | Abraham et al. |
| 5,169,850 | A | 12/1992 | Dusza et al. |
| 5,225,402 | A | 7/1993 | Ogawa et al. |
| 5,258,407 | A | 11/1993 | Washburn et al. |
| 5,260,325 | A | 11/1993 | Markwalder et al. |
| 5,272,167 | A | 12/1993 | Girijavallabhan et al. |
| 5,274,104 | A | 12/1993 | Arnaud et al. |
| 5,290,803 | A | 3/1994 | Abraham et al. |
| 5,314,880 | A | 5/1994 | Whittaker et al. |
| 5,356,904 | A | 10/1994 | Freidinger et al. |
| 5,382,680 | A | 1/1995 | Abraham et al. |
| 5,426,105 | A | 6/1995 | Manning et al. |
| 5,432,191 | A | 7/1995 | Abraham et al. |
| 5,436,254 | A | 7/1995 | Ogawa et al. |
| 5,446,194 | A | 8/1995 | Backstrom et al. |
| 5,459,144 | A | 10/1995 | Girijavallabhan et al. |
| 5,585,394 | A | 12/1996 | Di Malta et al. |
| 5,591,892 | A | 1/1997 | Abraham et al. |
| 5,596,020 | A | 1/1997 | Morris et al. |
| 5,602,137 | A | 2/1997 | Ruhter et al. |
| 5,648,375 | A | 7/1997 | Abraham et al. |
| 5,650,513 | A | 7/1997 | Langhals et al. |
| 5,652,247 | A | 7/1997 | Ogawa et al. |
| 5,674,879 | A | 10/1997 | Manning et al. |
| 5,677,330 | A | 10/1997 | Abraham et al. |
| 5,705,521 | A | 1/1998 | Abraham et al. |
| 5,731,454 | A | 3/1998 | Abraham et al. |
| 5,750,532 | A | 5/1998 | Girijavallabhan et al. |
| 5,786,379 | A | 7/1998 | Bernardon |
| 5,795,907 | A | 8/1998 | Kalindjian et al. |
| 5,872,282 | A | 2/1999 | Abraham et al. |
| 5,912,260 | A | 6/1999 | Kalindjian et al. |
| 5,919,829 | A | 7/1999 | Kalindjian et al. |
| 5,927,283 | A | 7/1999 | Abraham et al. |
| 5,932,569 | A | 8/1999 | Janssens et al. |
| 5,939,437 | A | 8/1999 | Kalindjian et al. |

(Continued)

FOREIGN PATENT DOCUMENTS

CN 1736485 2/2006

(Continued)

OTHER PUBLICATIONS

Allen et al., 2010, CAS: 152: 592058.*

Barf T et al: "Recent progress in 11-[beta]-hydroxysteroid dehydrogenase type 1 (11-[beta]-HSD1) inhibitor development" Drugs of the Future 2006 Spain, vol. 31, No. 3, Mar. 2006, pp. 231-243.

European Search Report for European Patent Application No. 06112359.2 dated Jun. 21, 2006.

(Continued)

*Primary Examiner* — Rei-tsang Shiao

(74) *Attorney, Agent, or Firm* — Samuel B. Rollins; Robert S. Dailey

(57) ABSTRACT

A novel class of compounds of the general formula (I), their use in therapy, pharmaceutical compositions comprising the compounds, as well as their use in the manufacture of medicaments are described. The present compounds modulate the activity of 11β-hydroxy-steroid dehydrogenase type 1 (11βHSD1) and are accordingly useful in the treatment of diseases in which such a modulation is beneficial, e.g. the metabolic syndrome.

(I)

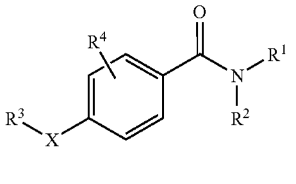

10 Claims, No Drawings

U.S. PATENT DOCUMENTS

| | | | | |
|---|---|---|---|---|
| 6,001,879 | A | 12/1999 | Seitz et al. | |
| 6,096,736 | A | 8/2000 | Ogawa et al. | |
| 6,124,289 | A | 9/2000 | He et al. | |
| 6,458,803 | B1 | 10/2002 | Sikorski et al. | |
| 6,506,783 | B1 | 1/2003 | Camden | |
| 6,521,641 | B1 | 2/2003 | Klein et al. | |
| 6,548,549 | B1 | 4/2003 | Seitz et al. | |
| 6,613,803 | B1 | 9/2003 | Wang et al. | |
| 6,638,947 | B2 | 10/2003 | Wang et al. | |
| 6,696,442 | B2 | 2/2004 | Wang et al. | |
| 6,833,371 | B2 | 12/2004 | Atkinson et al. | |
| 7,129,242 | B2 * | 10/2006 | Satoh et al. | 514/247 |
| 7,157,490 | B2 | 1/2007 | Colandrea et al. | |
| 7,186,735 | B2 | 3/2007 | Strobel et al. | |
| 7,265,122 | B2 | 9/2007 | Wu et al. | |
| 7,358,238 | B2 | 4/2008 | Andersen et al. | |
| 7,501,405 | B2 | 3/2009 | Kampen et al. | |
| 7,557,110 | B2 | 7/2009 | Kataoka et al. | |
| 7,700,583 | B2 * | 4/2010 | Gundertofte et al. | 514/213.01 |
| 7,723,323 | B2 | 5/2010 | Andersen et al. | |
| 2002/0006932 | A1 | 1/2002 | Galley et al. | |
| 2002/0115671 | A1 | 8/2002 | Goehring | |
| 2003/0144256 | A1 | 7/2003 | Klein et al. | |
| 2004/0142922 | A1 | 7/2004 | Alanine et al. | |
| 2004/0186102 | A1 | 9/2004 | Wu et al. | |
| 2005/0009871 | A1 | 1/2005 | Ramesh et al. | |
| 2005/0054850 | A1 | 3/2005 | Wu et al. | |
| 2005/0080087 | A1 | 4/2005 | Pendri et al. | |
| 2005/0154202 | A1 | 7/2005 | Hagmann et al. | |
| 2005/0261302 | A1 | 11/2005 | Hoff et al. | |
| 2006/0009918 | A1 | 1/2006 | Mallik et al. | |
| 2006/0079506 | A1 | 4/2006 | Linders et al. | |
| 2006/0094699 | A1 | 5/2006 | Kampen et al. | |
| 2006/0111366 | A1 | 5/2006 | Andersen et al. | |
| 2006/0149070 | A1 | 7/2006 | Rohde et al. | |
| 2006/0281773 | A1 | 12/2006 | Patel et al. | |
| 2007/0054882 | A1 | 3/2007 | Klein et al. | |
| 2007/0270408 | A1 | 11/2007 | Andersen et al. | |
| 2008/0108598 | A1 | 5/2008 | Andersen et al. | |
| 2009/0105289 | A1 | 4/2009 | Kilburn et al. | |
| 2009/0118259 | A1 | 5/2009 | Kilburn et al. | |
| 2009/0124598 | A1 | 5/2009 | Andersen et al. | |
| 2009/0137574 | A1 | 5/2009 | Kampen et al. | |
| 2009/0264412 | A1 | 10/2009 | Kampen et al. | |
| 2009/0264414 | A1 | 10/2009 | Andersen et al. | |
| 2009/0306048 | A1 | 12/2009 | Kilburn et al. | |
| 2009/0325932 | A1 | 12/2009 | Ebdrup et al. | |
| 2010/0056600 | A1 | 3/2010 | Ebdrup et al. | |
| 2010/0076041 | A1 | 3/2010 | Kilburn et al. | |
| 2010/0087543 | A1 | 4/2010 | Ebdrup et al. | |
| 2010/0120743 | A1 | 5/2010 | Gundertofte et al. | |
| 2010/0137377 | A1 | 6/2010 | Petersen et al. | |
| 2010/0168083 | A1 | 7/2010 | Ebdrup | |
| 2010/0197658 | A1 | 8/2010 | Andersen et al. | |
| 2010/0331366 | A1 | 12/2010 | Ebdrup | |
| 2011/0003852 | A1 | 1/2011 | Ebdrup | |
| 2011/0003856 | A1 | 1/2011 | Ebdrup | |
| 2011/0039853 | A1 | 2/2011 | Ebdrup | |

FOREIGN PATENT DOCUMENTS

| | | | |
|---|---|---|---|
| DE | 4338784 | | 5/1995 |
| EP | 1 669 350 | | 6/2006 |
| FR | 2456731 | | 12/1980 |
| GB | 825514 | | 11/1956 |
| JP | 08-048662 | | 2/1996 |
| JP | 09-221476 | | 8/1997 |
| JP | 11-152269 | | 6/1999 |
| JP | 2001 139574 | | 5/2001 |
| JP | 2003-286171 | | 10/2003 |
| JP | 2007-231005 | | 9/2007 |
| WO | WO 94/01113 | | 1/1994 |
| WO | WO 94/18193 | | 8/1994 |
| WO | WO 97/07789 | | 3/1997 |
| WO | WO 97/22588 | | 6/1997 |
| WO | WO 97/24328 | | 7/1997 |
| WO | WO 98/46559 | | 10/1998 |
| WO | WO 99/30699 | | 6/1999 |
| WO | WO 99/61013 | | 12/1999 |
| WO | WO 00/12074 | | 3/2000 |
| WO | WO 00/46197 | | 8/2000 |
| WO | WO 00/47558 | | 8/2000 |
| WO | WO 00/63165 | | 10/2000 |
| WO | WO 00/73283 | | 12/2000 |
| WO | WO 01/02385 | | 1/2001 |
| WO | WO 01/22969 | | 4/2001 |
| WO | WO 01/32621 | | 5/2001 |
| WO | WO 01/44213 | | 6/2001 |
| WO | WO 01/64676 | | 9/2001 |
| WO | WO 01/90090 | | 11/2001 |
| WO | WO 01/90091 | | 11/2001 |
| WO | WO 01/90092 | | 11/2001 |
| WO | WO 01/90093 | | 11/2001 |
| WO | WO 01/90094 | | 11/2001 |
| WO | WO 02/00626 | | 1/2002 |
| WO | WO 02/02797 | | 1/2002 |
| WO | WO 02/10191 | | 2/2002 |
| WO | WO 02/072084 | | 9/2002 |
| WO | WO 02/076435 | | 10/2002 |
| WO | WO 02/094799 | | 11/2002 |
| WO | WO 20/089781 | | 11/2002 |
| WO | WO 02/100819 | | 12/2002 |
| WO | WO 03/000649 | | 1/2003 |
| WO | WO 03/028641 | | 4/2003 |
| WO | WO 03/028730 | | 4/2003 |
| WO | WO 03/029246 | | 5/2003 |
| WO | WO 03/037274 | | 5/2003 |
| WO | WO 03/037900 | | 5/2003 |
| WO | WO 03/065983 | | 8/2003 |
| WO | WO 03/070732 | | 8/2003 |
| WO | WO 03/086410 | | 10/2003 |
| WO | WO 2004/024896 | | 3/2004 |
| WO | WO 2004/024897 | | 3/2004 |
| WO | WO 2004/033427 | | 4/2004 |
| WO | WO 2004/052461 | | 6/2004 |
| WO | WO 2004/056744 | | 7/2004 |
| WO | WO 2004/056745 | | 7/2004 |
| WO | WO 2004/065351 | | 8/2004 |
| WO | WO 2004/075823 | | 9/2004 |
| WO | WO 2004/087159 | | 10/2004 |
| WO | WO 2004/089380 | | 10/2004 |
| WO | WO 2004/089415 | | 10/2004 |
| WO | WO 2004/089416 | | 10/2004 |
| WO | WO 2004/089470 | | 10/2004 |
| WO | WO 2004/089471 | | 10/2004 |
| WO | WO 2004/089896 | | 10/2004 |
| WO | WO2004/089896 | * | 10/2004 |
| WO | WO 2004/091610 | | 10/2004 |
| WO | WO 2005/013950 | | 2/2005 |
| WO | WO 2005/032484 | | 4/2005 |
| WO | WO 2005/035534 | | 4/2005 |
| WO | WO 2005/085202 | | 9/2005 |
| WO | WO 2005/095397 | | 10/2005 |
| WO | WO 2005/115975 | | 12/2005 |
| WO | WO 2006/009835 | | 1/2006 |
| WO | WO 2006/014012 | | 2/2006 |
| WO | WO 2006/028958 | | 3/2006 |
| WO | WO 2006/040329 | | 4/2006 |
| WO | WO 2006/044645 | | 4/2006 |
| WO | WO 2006/048330 | | 5/2006 |
| WO | WO 2006/055752 | | 5/2006 |
| WO | WO 2006/094633 | | 9/2006 |
| WO | WO 2006/105127 | | 10/2006 |
| WO | WO 2006/113261 | | 10/2006 |
| WO | WO 2006/136402 | | 12/2006 |
| WO | WO 2007/046001 | | 4/2007 |
| WO | WO 2007/051810 | | 5/2007 |
| WO | WO 2007/051811 | | 5/2007 |
| WO | WO 2007/058960 | | 5/2007 |
| WO | WO 2007/059905 | | 5/2007 |
| WO | WO 2007/066784 | | 6/2007 |
| WO | WO 2007/107550 | | 9/2007 |
| WO | WO 2007/109160 | | 9/2007 |
| WO | WO 2007/144394 | | 12/2007 |
| WO | WO 2008/002244 | | 1/2008 |
| WO | WO 2008/006702 | | 1/2008 |
| WO | WO 2008/006703 | | 1/2008 |

| | | |
|---|---|---|
| WO | WO 2008/101885 | 8/2008 |
| WO | WO 2008/101886 | 8/2008 |
| WO | WO 2008/101907 | 8/2008 |
| WO | WO 2008/101914 | 8/2008 |
| WO | WO 2008/110196 | 9/2008 |
| WO | WO 2008/119017 | 10/2008 |
| WO | WO 2008/127924 | 10/2008 |
| WO | WO 2008/134221 | 11/2008 |
| WO | WO 2009/126863 | 10/2009 |
| WO | WO 2010/057126 | 5/2010 |
| WO | WO 2010/059618 | 5/2010 |

OTHER PUBLICATIONS

European Search Report for European Patent Application No. 06115591.7 dated Dec. 19, 2006.
European Search Report for European Patent Application No. 06117119.5 dated Dec. 18, 2006.
European Search Report for European Patent Application No. 06117120.3 dated Apr. 16, 2007.
Fotsch C. et al., "11[beta]-Hydroxysteroid dehydrogenase-1 as a therapeutic target for metabolic diseases" Expert Opinion on Therapeutic Patents, Ashley Publications, GB, vol. 15, No. 3, 2005, pp. 289-303.
Ganguly A.K. et al.; "Sythesis of heterocyclic compounds using radical reactions" Tetrahedron Letters, Elsevier, Amsterdam, NL, vol. 43, No. 38, Sep. 16, 2002, pp. 6865-6868.
Kazumi Kondo et al: "Characterization of Orally Active Nonpeptide Vasopressin V2 Receptor Agonist" Journal of Medicinal Chemistry, vol. 45, No. 17, 2002, pp. 3805-3808.
Kazumi Kondo et al: "Novel Design of Nonpeptide AVP V2 Receptor Agonists: Structural Requirements for and Agonist Having 1-(4-Aminobenzoyl)-2,3,4,5,-tetrahydro-1H-1-benezazepine as a Template" Journal of Medicinal Chemistry, vol. 43, No. 23, 2000, pp. 4388-4397.
M Skowronska-Ptasinska et al: "Effect of Different Dialkylamino Groups on the Regioselectivity of Lithiation of 0-Protected 3-(Dialkylamino)phenols" Journal of Organic Chemistry, vol. 50, No. 15, 1985, pp. 2690-2698.
PCT International Search Report for Application No. PCT/EP2007/052929 dated Jun. 4, 2007.
PCT International Search Report for Application No. PCT/EP2007/055865 dated Oct. 29, 2007.
PCT International Search Report for Application No. PCT/EP2007/056467 dated Nov. 20, 2007.
PCT International Search Report for Application No. PCT/EP2007/056470 dated Sep. 27, 2007.
PCT Written Opinion for Application No. PCT/EP2007/052929 dated Jun. 4, 2007.
PCT Written Opinion for Application No. PCT/EP2007/055865 dated Oct. 29, 2007.
PCT Written Opinion for Application No. PCT/EP2007/056467 dated Nov. 20, 2007.
PCT Written Opinion for Application No. PCT/EP2007/056470 dated Sep. 27, 2007.
Tabuchi, S. et al.: "Novel Potent Antagonists of Human Neuropeptide Y Y5 Receptor. Part 1: 2-Oxobenzothiazolin-3-acetic Acid Derivatives" Bioorganic & Medicinal Chemistry Letters, vol. 12, 2002, pp. 1171-1175.
Villani, F.J. et al.; "Derivatives of 2-Azabicyclo[2.2.2]octane" Journal of Medicinal Chemistry, 1966, pp. 264-265.
Willoughby C A et al: "Solid Phase Synthesis of Aryl Amines" Tetrahedron Letters, Elsevier, Amsterdam, NL, vol. 37, No. 40, Sep. 30, 1996, pp. 7181-7184 XP004030858 ISSN: 0040-4039 table 2; compound 1.
Andrew et al., J. Clin. Endocrinol. Metab. vol. 87, pp. 277-285 (2002).
Andrews et al., J. Clin. Endocrinol. Metab. vol. 88, pp. 285-291 (2003).
Bird et al., J. Physiology vol. 585, pp. 187-201 (2007).
Brem et al., Hypertension vol. 31, pp. 459-462 (1998).
Brindley et al., Progress Lipid Res. vol. 30, pp. 349-360 (1991).
Bujalska et al., Endocrinology vol. 140, pp. 3188-3196 (1999).
Carruthers et al., J. Chem. Soc. Perkin Trans. 1 vol. 10, pp. 2854-2856 (1990).
Cooper et al., Bone vol. 27, pp. 375-381 (2000).
Coppola et al., J. Med. Chem. vol. 48, pp. 6696-6712 (2005).
Davani et al., J. Biol. Chem. vol. 275, pp. 34841-34844 (2000).
Demchenko, Chem. Hetero. Comp. vol. 36, pp. 985-988 (2000).
Desai et al., Tetrahedron Lett. vol. 34, pp. 7685-7688 (1993).
Donohue et al., J. Comb. Chem. vol. 4, pp. 23-32 (2002).
Evans et al., J. Med. Chem. vol. 35, pp. 3919-3927 (1992).
Giacomelli et al. Eur. J. Org. Chem. vol. 3, pp. 537-541 (2003).
Hashigaki et al., Chem. Pharm. Bull. vol. 32, pp. 3561-3568 (1984).
Hosfield et al., J. Biol. Chem. vol. 280, pp. 4639-4648 (2005).
Ignatova Irena D. et al.: "Tumor necrosis factor-alpha upregulates 11 beta-hydroxysteroid dehydrogenase type 1 expression by CCAAT/enhancer binding protein-beta in HepG2 cells" American Journal of Physiology—endocrinology and Metabolism, vol. 296, No. 2, Feb. 2009, pp. E367-E377.
Johnson et al., J. Org. Chem. vol. 35, pp. 622-626 (1970).
Koteletsev et al., Proc. Nat'l Acad. Sci. vol. 94, pp. 14924-14929 (1997).
Leyendecker et al., Nouveau J. de Chimie vol. 9, pp. 13-19 (1985).
Mariani et al., Farmaco vol. 38, pp. 653-663 (1983).
Massa et al., J. Heterocycl. Chem. vol. 27, pp. 1805-1808 (1990).
Masuzaki et al., J. Clin. Invest. vol. 112, pp. 83-90 (2003).
Masuzaki et al., Science vol. 294, pp. 2166-2170 (2001).
McCullough et al., J. Chem. Soc. Perkin Trans. 1 vol. 20, pp. 2553-2560 (1996).
Moisan et al., Endocrinology, vol. 127, pp. 1450-1455 (1990).
Morton et al., J. Biol. Chem. vol. 276, pp. 41293-41300 (2001).
Nankervis et al.: "Calcium sensitizazion as a positive inotropic mechanism . . . " Journal of Cardiovascular Pharmacology, vol. 24, No. 4, 1994, pp. 612-617.
Nieczypor et al., Eu. J. Org. Chem. vol. 2004, pp. 812-819 (2004).
Pending Claims for U.S. Appl. No. 11/665,103, filed Mar. 24, 2011.
Pending Claims for U.S. Appl. No. 12/092,223, filed Mar. 24, 2011.
Pending Claims for U.S. Appl. No. 12/092,230, filed Mar. 25, 2011.
Pending Claims for U.S. Appl. No. 12/293,709, filed Mar. 25, 2011.
Pending Claims for U.S. Appl. No. 12/304,501, filed Mar. 25, 2011.
Pending Claims for U.S. Appl. No. 12/307,999, filed May 23, 2011.
Pending Claims for U.S. Appl. No. 12/308,000, filed Mar. 28, 2011.
Pending Claims for U.S. Appl. No. 12/528,227, filed Mar. 28, 2011.
Pending Claims for U.S. Appl. No. 12/528,229, filed Mar. 29, 2011.
Pending Claims for U.S. Appl. No. 12/528,231, filed Mar. 28, 2011.
Pending Claims for U.S. Appl. No. 12/528,233, filed Mar. 29, 2011.
Pending Claims for U.S. Appl. No. 12/529,956, filed Mar. 29, 2011.
Pending Claims for U.S. Appl. No. 12/593,456, filed Mar. 29, 2011.
Pending Claims for U.S. Appl. No. 12/595,310, filed Mar. 29, 2011.
Pending Claims for U.S. Appl. No. 12/597,129, filed Mar. 29, 2011.
Pending Claims for U.S. Appl. No. 13/078,221, filed Apr. 1, 2011.
Pending Claims for U.S. Appl. No. 13/128,045, filed May 6, 2011.
Rauz et al., Invest. Opthalmol. Vis. Sci. vol. 42, pp. 2037-2042 (2001).
Reed et al., Scand. J. Gastroentreol. vol. 15, pp. 51-56 (1980).
Schwartz et al., Nature vol. 404, pp. 661-671 (2000).
Seefelter et al., Chemische Berichte vol. 96, pp. 3243-3253 (1963).
Sohar R et al: "Conformational Analysis of N-Acylazabycyclooctanes," Magnetic Resonance in Chemistry, John Wiley, Chichester, GB, vol. 23, No. 7, Jan. 1, 1985, pp. 506-513.
Souness et al., Steroids vol. 67, pp. 195-201 (2002).
Tannin et al., J. Biol. Chem. vol. 266, pp. 16653-16658 (1991).
Tomlinson et al., J. Clin. Endocrinol. Metab. vol. 87, pp. 57-62 (2002).
Walker et al., J. Clin. Endocrinol. Metab. vol. 80, pp. 3155-3159 (1995).
Whitworth et al., J. Hypertens. vol. 20, pp. 1035-1043 (2002).
Whorwood et al., J. Clin. Endocrinol. Metab. vol. 86, pp. 2296-2308 (2001).
Wu et al., Toxicology vol. 236, pp. 1-6 (2007).
Yang et al., Bioorg. Med. Chem. Lett. vol. 8, pp. 107-112 (1998).
Yau et al., Proc. Nat'l Acad. Sci. vol. 98, pp. 4716-4721 (2001).
Yudt et al., Mol. Endocrinol. vol. 16, pp. 1719-1726 (2002).

* cited by examiner

11β-HYDROXYSTEROID DEHYDROGENASE TYPE 1 ACTIVE COMPOUNDS

CROSS-REFERENCE TO RELATED APPLICATIONS

This application is the United States national stage application, pursuant to 35 U.S.C. 371, of PCT/EP2007/052929, filed Mar. 27, 2007, which claims benefit of priority to European Patent Application No. 06112359.2, filed Apr. 7, 2006.

FIELD OF INVENTION

The present invention relates to novel substituted cyclic amides, to their use in therapy, to pharmaceutical compositions comprising the compounds, to the use of said compounds in the manufacture of medicaments, and to therapeutic methods comprising the ad-ministration of said compounds. The present compounds modulate the activity of 11β-hydroxysteroid dehydrogenase type 1 (11βHSD1) and are accordingly useful in the treatment of diseases in which such a modulation is beneficial, such as the metabolic syndrome.

BACKGROUND OF THE INVENTION

The metabolic syndrome is a major global health problem. In the US, the prevalence in the adult population is currently estimated to be approximately 25%, and it continues to increase both in the US and worldwide. The metabolic syndrome is characterized by a combination of insulin resistance, dyslipidemia, obesity and hypertension leading to increased morbidity and mortality of cardiovascular diseases. People with the metabolic syndrome are at increased risk of developing frank type 2 diabetes, the prevalence of which is equally escalating.

In type 2 diabetes, obesity and dyslipidemia are also highly prevalent and around 70% of people with type 2 diabetes additionally have hypertension once again leading to increased mortality of cardiovascular diseases.

In the clinical setting, it has long been known that glucocorticoids are able to induce all of the cardinal features of the metabolic syndrome and type 2 diabetes.

11β-hydroxysteroid dehydrogenase type 1 (11βHSD1) catalyses the local generation of active glucocorticoid in several tissues and organs including predominantly the liver and adipose tissue, but also e.g. skeletal muscle, bone, pancreas, endothelium, ocular tissue and certain parts of the central nervous system. Thus, 11βHSD1 serves as a local regulator of glucocorticoid actions in the tissues and organs where it is expressed (Tannin et al., *J. Biol. Chem.,* 266, 16653 (1991); Bujalska et al., *Endocrinology,* 140, 3188 (1999); Whorwood et al., *J. Clin. Endocrinol. Metab.,* 86, 2296 (2001); Cooper et al., *Bone,* 27, 375 (2000); Davani et al., *J. Biol. Chem.,* 275, 34841 (2000); Brem et al., *Hypertension,* 31, 459 (1998); Rauz et al., *Invest. Opthalmol. Vis. Sci.,* 42, 2037 (2001); Moisan et al., *Endocrinology,* 127, 1450 (1990)).

The role of 11βHSD1 in the metabolic syndrome and type 2 diabetes is supported by several lines of evidence. In humans, treatment with the non-specific 11βHSD1 inhibitor carbenoxolone improves insulin sensitivity in lean healthy volunteers and people with type 2 diabetes. Likewise, 11βHSD1 knock-out mice are resistant to insulin resistance induced by obesity and stress. Additionally, the knock-out mice present with an anti-atherogenic lipid profile of decreased VLDL triglycerides and increased HDL-cholesterol. Conversely, mice that overexpress 11βHSD1 in adipocytes develop insulin resistance, hyperlipidemia and visceral obesity, a phenotype that resembles the human metabolic syndrome (Andrews et al., *J. Clin. Endocrinol. Metab.,* 88, 285 (2003); Walker et al., *J. Clin. Endocrinol. Metab.,* 80, 3155 (1995); Morton et al., *J. Biol. Chem.* 276, 41293 (2001); Kotelevtsev et al., *Proc. Natl. Acad. Sci. USA,* 94, 14924 (1997); Masuzaki et al., *Science,* 294, 2166 (2001)).

The more mechanistic aspects of 11βHSD1 modulation and thereby modulation of intracellular levels of active glucocorticoid have been investigated in several rodent models and different cellular systems. 11βHSD1 promotes the features of the metabolic syndrome by increasing hepatic expression of the rate-limiting enzymes in gluconeogenesis, namely phosphoenolpyuvate carboxykinase and glucose-6-phosphatase, promoting the differentiation of preadipocytes into adipocytes thus facilitating obesity, directly and indirectly stimulating hepatic VLDL secretion, decreasing hepatic LDL uptake and increasing vessel contractility (Kotelevtsev et al., *Proc. Natl. Acad. Sci. USA,* 94, 14924 (1997); Morton et al., *J. Biol. Chem.* 276, 41293 (2001); Bujalska et al., *Endocrinology,* 140, 3188 (1999); Souness et al., Steroids, 67, 195 (2002); Brindley & Salter, *Prog. Lipid Res.,* 30, 349 (1991)).

WO 01/90090, WO 01/90091, WO 01/90092, WO 01/90093 and WO 01/90094 discloses various thiazol-sulfonamides as inhibitors of the human 11β-hydroxysteroid dehydrogenase type 1 enzyme, and further states that said compounds may be useful in treating diabetes, obesity, glaucoma, osteoporosis, cognitive disorders, immune disorders and depression. WO 04/089470 discloses various substituted amides as modulators of the human 11β-hydroxysteroid dehydrogenase type 1 enzyme, and further states that said compounds may be useful in treating medical disorders where a decreased intracellular concentration of active glucocorticoid is desirable. WO 2004/089415 and WO 2004/089416 discloses various combination therapies using an 11β-hydroxysteroid dehydrogenase type 1 inhibitor and respectively a glucocorticoid receptor agonist or an antihypertensive agent.

We have now found novel substituted cyclic amides that modulate the activity of 11βHSD1 leading to altered intracellular concentrations of active glucocorticoid. More specifically, the present compounds inhibit the activity of 11βHSD1 leading to decreased intracellular concentrations of active glucocorticoid. Thus, the present compounds can be used to treat disorders where a decreased level of active intracellular glucocorticoid is desirable, such as e.g. the metabolic syndrome, type 2 diabetes, impaired glucose tolerance (IGT), impaired fasting glucose (IFG), dyslipidemia, obesity, hypertension, diabetic late complications, cardiovascular diseases, arteriosclerosis, atherosclerosis, myopathy, muscle wasting, osteoporosis, neurodegenerative and psychiatric disorders, and adverse effects of treatment or therapy with glucocorticoid receptor agonists.

Objects of the present invention are to provide compounds, pharmaceutical compositions and use of said compounds that modulate the activity of 11βHSD1.

DEFINITIONS

In the following structural formulas and throughout the present specification, the following terms have the indicated meaning:

The term “halogen” or “halo” means fluorine, chlorine, bromine or iodine.

The term “hydroxy” shall mean the radical —OH.

The term “sulfanyl” shall mean the radical —S—.

The term "sulfo" shall mean the radical $HO_3S$—.

The term "sulfonyl" shall mean the radical —S(=O)$_2$—.

The term "oxo" shall mean the radical =O.

The term "amino" shall mean the radical —$NH_2$.

The term "nitro" shall mean the radical —$NO_2$.

The term "cyano" shall mean the radical —CN.

The term "carboxy" shall mean the radical —(C=O)OH.

The term "perhalomethyl" includes but are not limited to trifluoromethyl, difluoromethyl, monofluoromethyl, trichloromethyl and the like.

The term "trihalomethyl" includes trifluoromethyl, trichloromethyl, tribromomethyl, and triiodomethyl.

The term "trihalomethoxy" includes trifluorometoxy, trichlorometoxy, tribromometoxy, and triiodometoxy.

The term "alkyl" as used herein represents a saturated, branched or straight hydro-carbon group having the indicated number of carbon atoms, e.g. $C_{1-2}$-alkyl, $C_{1-3}$-alkyl, $C_{1-4}$-alkyl, $C_{1-6}$-alkyl, $C_{2-6}$-alkyl, $C_{3-6}$-alkyl, $C_{1-10}$-alkyl, and the like. Representative examples are methyl, ethyl, propyl (e.g. prop-1-yl, prop-2-yl (or iso-propyl)), butyl (e.g. 2-methylprop-2-yl (or tert-butyl), but-1-yl, but-2-yl), pentyl (e.g. pent-1-yl, pent-2-yl, pent-3-yl), 2-methylbut-1-yl, 3-methylbut-1-yl, hexyl (e.g. hex-1-yl), heptyl (e.g. hept-1-yl), octyl (e.g. oct-1-yl), nonyl (e.g. non-1-yl), and the like. The term "$C_{1-6}$-alkyl" as used herein represents a saturated, branched or straight hydrocarbon group having from 1 to 6 carbon atoms, e.g. $C_{1-2}$-alkyl, $C_{1-3}$-alkyl, $C_{1-4}$-alkyl, $C_{1-6}$-alkyl, $C_{2-6}$-alkyl, $C_{3-6}$-alkyl, and the like. Representative examples are methyl, ethyl, propyl (e.g. prop-1-yl, prop-2-yl (or iso-propyl)), butyl (e.g. 2-methylprop-2-yl (or tert-butyl), but-1-yl, but-2-yl), pentyl (e.g. pent-1-yl, pent-2-yl, pent-3-yl), 2-methylbut-1-yl, 3-methylbut-1-yl, hexyl (e.g. hex-1-yl), and the like. The term "$C_{1-4}$-alkyl" as used herein represents a saturated, branched or straight hydrocarbon group having from 1 to 4 carbon atoms, e.g. $C_{1-2}$-alkyl, $C_{1-3}$-alkyl, $C_{1-4}$-alkyl and the like. Representative examples are methyl, ethyl, propyl (e.g. prop-1-yl, prop-2-yl (or iso-propyl)), butyl (e.g. 2-methylprop-2-yl (or tert-butyl), but-1-yl, but-2-yl), and the like.

The term "alkenyl" includes $C_2$-$C_6$ straight chain unsaturated aliphatic hydrocarbon groups and branched $C_3$-$C_6$ unsaturated aliphatic hydrocarbon groups having the specified number of carbon atoms. For example, this definition shall include but is not limited to ethenyl, propenyl, butenyl, pentenyl, hexenyl, methylpropenyl, methylbutenyl and the like.

The term "alkynyl" includes $C_2$-$C_6$ straight chain unsaturated aliphatic hydrocarbon groups and $C_4$-$C_6$ branched unsaturated aliphatic hydrocarbon groups having the specified number of carbon atoms. For example, this definition shall include but is not limited to ethynyl, propynyl, butynyl, pentynyl, hexynyl, methylbutynyl, and the like.

The term "saturated or partially saturated cyclic, bicyclic or tricyclic ring system" represents but are not limited to azepanyl, azocanyl, 1,2,3,4-tetrahydro-quinolinyl, 1,2,3,4-tetrahydro-isoquinolinyl, 1,2,3,4-tetrahydro-quinoxalinyl, indolinyl, 6-aza-bicyclo[3.2.1]octane, 2-aza-bicyclo[4.1.1]octane, 2-aza-bicyclo[3.2.1]octanyl, 7-aza-bicyclo[4.1.1]octanyl, 9-aza-bicyclo[3.3.2]decanyl, 4-aza-tricyclo[4.3.1.1$^{3,8}$]undecanyl, 9-aza-tricyclo[3.3.2.0$^{3,7}$]decanyl, 8-aza-spiro[4.5]decane.

The term "cycloalkyl" as used herein represents a saturated monocyclic carbocyclic ring having the specified number of carbon atoms, e.g. $C_{3-6}$-alkyl, $C_{3-8}$-alkyl, $C_{3-10}$-alkyl, and the like. Representative examples are cyclopropyl, cyclobutyl, cyclopentyl, cyclohexyl, cyclo-heptyl, cyclooctyl, and the like. Cycloalkyl is also intended to represent a saturated bicyclic carbocyclic ring having from 4 to 10 carbon atoms. Representative examples are decahydronaphthalenyl, bicyclo[3.3.0]octanyl, and the like. Cycloalkyl is also intended to represent a saturated carbocyclic ring having from 3 to 10 carbon atoms and containing one or two car-bon bridges. Representative examples are adamantyl, norbornanyl, nortricyclyl, bicycle-[3.2.1]octanyl, bicyclo[2.2.2]octanyl, tricyclo[5.2.1.0/2,6]decanyl, bicyclo[2.2.1]heptyl, and the like. Cycloalkyl is also intended to represent a saturated carbocyclic ring having from 3 to 10 carbon atoms and containing one or more spiro atoms. Representative examples are spiro[2.5]octanyl, spiro[4.5]decanyl, and the like.

The term "cycloalkylalkyl" (e.g. cyclopropylmethyl, cyclobutylethyl, adamantylmethyl and the like) represents a cycloalkyl group as defined above attached through an alkyl group having the indicated number of carbon atoms or substituted alkyl group as defined above.

The term "cycloalkenyl" (e.g. cyclobutenyl, cyclopentenyl, cyclohexenyl, cycloheptenyl, cyclooctenyl, cyclononenyl, cyclodecenyl and the like) represents a partially saturated, mono-, bi-, tri- or spirocarbocyclic group having the specified number of carbon atoms.

The term "cycloalkylcarbonyl" (e.g. cyclopropylcarbonyl, cyclohexylcarbonyl) represents an cycloalkyl group as defined above having the indicated number of carbon atoms attached through a carbonyl group.

The term "hetcycloalkylcarbonyl" (e.g. 1-piperidin-4-yl-carbonyl, 1-(1,2,3,4-tetrahydro-isoquinolin-6-yl)carbonyl) represents an hetcycloalkyl group as defined above having the indicated number of carbon atoms attached through a carbonyl group.

The term "hetcycloalkyl" (e.g. tetrahydrofuranyl, tetrahydropyranyl, tetahydrothiopyranyl, piperidine, pyridazine and the like) represents a saturated mono-, bi-, tri- or spiro-carbocyclic group having the specified number of carbon atoms and one or two additional heteroatoms or groups selected from nitrogen, oxygen, sulphur, SO or $SO_2$.

The term "hetcycloalkylalkyl" (e.g. tetrahydrofuranylmethyl, tetrahydropyranylethyl, tertahydrothiopyranylmethyl, and the like) represents a hetcycloalkyl group as defined above attached through an alkyl group having the indicated number of carbon atoms or substituted alkyl group as defined above.

The term "alkyloxy" (e.g. methoxy, ethoxy, propyloxy, allyloxy, cyclohexyloxy) represents an alkyl group as defined above having the indicated number of carbon atoms attached through an oxygen bridge.

The term "alkyloxyalkyl" (e.g. methyloxymethyl and the like) represents an alkyloxy group as defined above attached through an "alkyl" group.

The term "aryloxy" (e.g. phenoxy, naphthyloxy and the like) represents an aryl group as defined below attached through an oxygen bridge.

The term "hetaryloxy" (e.g. 2-pyridyloxy and the like) represents a hetaryl group as defined below attached through an oxygen bridge.

The term "aryloxyalkyl" (e.g. phenoxymethyl, naphthyloxyethyl and the like) represents an aryloxy group as defined above attached through an "alkyl" group having the indicated number of carbon atoms.

The term "arylalkyloxy" (e.g. phenethyloxy, naphthylmethyloxy and the like) represents an arylalkyl group as defined below attached through an oxygen bridge.

The term "hetarylalkyloxy" (e.g. 2-pyridylmethyloxy and the like) represents a hetarylalkyl group as defined below attached through an oxygen bridge.

The term "hetaryloxyalkyl" (e.g. 2-pyridyloxymethyl, 2-quinolyloxyethyl and the like) represents a hetaryloxy group as defined above attached through an "alkyl" group having the indicated number of carbon atoms.

The term "hetarylalkyloxyalkyl" (e.g. 4-methoxymethyl-pyrimidine, 2-methoxymethyl-quinoline and the like) represents a hetarylalkyloxy group as defined above attached through an "alkyl" group having the indicated number of carbon atoms.

The term "arylalkyloxyalkyl" (e.g. ethoxymethyl-benzene, 2-methoxymethyl-naphthalene and the like) represents an arylalkyloxy group as defined above attached through an "alkyl" group having the indicated number of carbon atoms.

The term "alkylthio" (e.g. methylthio, ethylthio and the like) represents an alkyl group as defined above attached through a sulphur bridge.

The term "alkyloxycarbonyl" (e.g. methylformiat, ethylformiat and the like) represents an alkyloxy group as defined above attached through a carbonyl group.

The term "aryloxycarbonyl" (e.g. phenylformiat, 2-thiazolylformiat and the like) represents an aryloxy group as defined above attached through a carbonyl group.

The term "arylalkyloxycarbonyl" (e.g. benzylformiat, phenyletylformiat and the like) represents an "arylalkyloxy" group as defined above attached through a carbonyl group.

The term "arylalkyl" (e.g. benzyl, phenylethyl, 3-phenylpropyl, 1-naphtylmethyl, 2-(1-naphtyl)ethyl and the like) represents an aryl group as defined below attached through an alkyl having the indicated number of carbon atoms or substituted alkyl group as defined above.

The term "hetarylalkyl" (e.g. (2-furyl)methyl, (3-furyl) methyl, (2-thienyl)methyl, (3-thienyl)methyl, (2-pyridyl)methyl, 1-methyl-1-(2-pyrimidyl)ethyl and the like) represents a hetaryl group as defined below attached through an alkyl having the indicated number of carbon atoms or substituted alkyl group as defined above.

The term "alkylcarbonyl" as used herein refers to the alkyl group as defined above having the indicated number of carbon atoms attached through a carbonyl group. Representative examples are acetyl (methylcarbonyl), propionyl (ethylcarbonyl), butanoyl (prop-1-ylcarbonyl, prop-2-ylcarbonyl), pentylcarbonyl, 3-hexenylcarbonyl, octylcarbonyl, and the like.

The term "arylcarbonyl" (e.g. benzoyl) represents an aryl group as defined below attached through a carbonyl group.

The term "hetarylcarbonyl" (e.g. 2-thiophenylcarbonyl, 3-methoxy-anthrylcarbonyl, oxazolylcarbonyl and the like) represents a hetaryl group as defined below attached through a carbonyl group.

The term "alkylcarbonylalkyl" (e.g. propan-2-one, 4,4-dimethyl-pentan-2-one and the like) represents an alkylcarbonyl group as defined above attached through an alkyl group as defined above having the indicated number of carbon atoms.

The term "hetarylcarbonylalkyl" (e.g. 1-pyridin-2-yl-propan-1-one, 1-(1-H-imidazol-2-yl)-propan-1-one and the like) represents a hetarylcarbonyl group as defined above attached through an alkyl group as defined above having the indicated number of carbon atoms.

The term "arylalkylcarbonyl" (e.g. phenylpropylcarbonyl, phenylethylcarbonyl and the like) represents an arylalkyl group as defined above having the indicated number of carbon atoms attached through a carbonyl group.

The term "hetarylalkylcarbonyl" (e.g. imidazolylpentylcarbonyl and the like) represents a hetarylalkyl group as defined above wherein the alkyl group is in turn attached through a carbonyl.

The term "alkylcarboxy" (e.g. heptylcarboxy, cyclopropylcarboxy, 3-pentenylcarboxy) represents an alkylcarbonyl group as defined above wherein the carbonyl is in turn attached through an oxygen bridge.

The term "arylcarboxy" (e.g. benzoic acid and the like) represents an arylcarbonyl group as defined above wherein the carbonyl is in turn attached through an oxygen bridge.

The term "alkylcarboxyalkyl" (e.g. heptylcarboxymethyl, propylcarboxy tert-butyl, 3-pentylcarboxyethyl) represents an alkylcarboxy group as defined above wherein the carboxy group is in turn attached through an alkyl group as defined above having the indicated number of carbon atoms.

The term "arylalkylcarboxy" (e.g. benzylcarboxy, phenylpropylcarboxy and the like) represents an arylalkylcarbonyl group as defined above wherein the carbonyl is in turn attached through an oxygen bridge.

The term "hetarylalkylcarboxy" (e.g. (1-H-imidazol-2-yl)-acetic acid, 3-pyrimidin-2-yl-propionic acid and the like) represents a hetarylalkylcarbonyl group as defined above wherein the carbonyl is in turn attached through an oxygen bridge.

The term "alkylS(O)$_n$" (e.g. ethylsulfonyl, ethylsulfinyl and the like) represents an alkyl group as defined above, wherein the alkyl group is in turn attached through a sulphur bridge wherein the sulphur is substituted with n oxygen atoms.

The term "arylS(O)$_n$" (e.g. phenylsulfinyl, naphthyl-2-sulfonyl and the like) represents an aryl group as defined above, wherein the aryl group is in turn attached through a sulphur bridge wherein the sulphur is substituted with n oxygen atoms.

The term "arylalkylS(O)$_n$" (e.g. benzylsulfinyl, phenetyl-2-sulfonyl and the like) represents an arylalkyl group as defined above, wherein the arylalkyl group is in turn attached through a sulphur bridge wherein the sulphur is substituted with n oxygen atoms.

The term "bridge" as used herein represents a connection in a saturated or partly saturated ring between two atoms of such ring that are not neighbors through a chain of 1 to 3 atoms selected from carbon, nitrogen, oxygen and sulfur. Representative examples of such connecting chains are $-CH_2-$, $-CH_2CH_2-$, $-CH_2NHCH_2-$, $-CH_2CH_2CH_2-$, $-CH_2OCH_2-$, and the like. In one embodiment according to the invention, the connecting chain is selected from the group consisting of $-CH_2-$, $-CH_2CH_2-$, or $-CH_2OCH_2-$.

The term "spiro atom" as used herein represents a carbon atom in a saturated or partly saturated ring that connects both ends of a chain of 3 to 7 atoms selected from carbon, nitrogen, oxygen and sulfur. Representative examples are $-(CH_2)_5-$, $-(CH_2)_3-$, $-(CH_2)_4-$, $-CH_2NHCH_2CH_2-$, $-CH_2CH_2NHCH_2CH_2-$, $-CH_2NHCH_2CH_2CH_2-$, $-CH_2CH_2OCH_2-$, $-OCH_2CH_2O-$, and the like.

The term "aryl" as used herein is intended to include monocyclic, bicyclic or poly-cyclic carbocyclic aromatic rings. Representative examples are phenyl, naphthyl (e.g. naphth-1-yl, naphth-2-yl), anthryl (e.g. anthr-1-yl, anthr-9-yl), phenanthryl (e.g. phenanthr-1-yl, phenanthr-9-yl), and the like. Aryl is also intended to include monocyclic, bicyclic or poly-cyclic carbocyclic aromatic rings substituted with carbocyclic aromatic rings. Representative examples are biphenyl (e.g. biphenyl-2-yl, biphenyl-3-yl, biphenyl-4-yl), phenylnaphthyl (e.g. 1-phenylnaphth-2-yl, 2-phenylnaphth-1-yl), and the like. Aryl is also intended to include partially saturated bicyclic or polycyclic carbocyclic rings with at least one unsaturated moiety (e.g. a benzo moiety). Representative examples are, indanyl (e.g. indan-1-yl, indan-5-yl), indenyl (e.g. inden-1-yl, inden-5-yl), 1,2,3,4-tetrahydronaphthyl (e.g. 1,2,3,4-tetrahydronaphth-1-yl, 1,2,3,4-tetrahydronaphth-2- yl, 1,2,3,4-tetrahydronaphth-6-yl), 1,2-dihydronaphthyl (e.g. 1,2-dihydronaphth-1-yl, 1,2-dihydronaphth-4-yl, 1,2-dihydronaphth-6-yl), fluorenyl (e.g. fluoren-1-yl, fluoren-4-yl, fluoren-9-yl), and the like. Aryl is also intended to include partially saturated bicyclic or polycyclic carbocyclic aromatic rings containing one or two bridges. Representative examples are, benzonorbornyl (e.g. benzonorborn-3-yl, benzonorborn-6-yl), 1,4-ethano-1,2,3,4-tetrahydronapthyl (e.g. 1,4-ethano-1,2,3,4-tetrahydronapth-2-yl, 1,4-ethano-1,2,3,4-tetrahydronapth-10-yl), and the like. Aryl is also intended to include partially saturated bicyclic or polycyclic carbocyclic aromatic rings containing one or more spiro atoms. Representative examples are spiro[cyclopentane-1,1'-indane]-4-yl, spiro[cyclopentane-1,1'-indene]-4-yl, spiro[piperidine-4,1'-indane]-1-yl, spiro[piperidine-3,2'-indane]-1-yl, spiro[piperidine-4,2'-indane]-1-yl, spiro[piperidine-4,1'-indane]-3'-yl, spiro[pyrrolidine-3,2'-indane]-1-yl, spiro[pyrrolidine-3,1'-(3',4'-dihydronaphthalene)]-1-yl, spiro[piperidine-3,1'-(3',4'-dihydronaphthalene)]-1-yl, spiro[piperidine-4,1'-(3',4'-dihydronaphthalene)]-1-yl, spiro[imidazolidine-4,7-indane]-1-yl, spiro[piperidine-4,1'-indene]-1-yl, and the like.

The term “hetaryl” or “heteroaryl” as used herein is intended to include monocyclic heterocyclic aromatic rings containing one or more heteroatoms selected from nitrogen, oxygen, sulfur, SO and S(=O)$_2$. Representative examples are pyrrolyl (e.g. pyrrol-1-yl, pyrrol-2-yl, pyrrol-3-yl), furanyl (e.g. furan-2-yl, furan-3-yl), thienyl (e.g. thien-2-yl, thien-3-yl), oxazolyl (e.g. oxazol-2-yl, oxazol-4-yl, oxazol-5-yl), thiazolyl (e.g. thiazol-2-yl, thiazol-4-yl, thiazol-5-yl), imidazolyl (e.g. imidazol-2-yl, imidazol-4-yl, imidazol-5-yl), pyrazolyl (e.g. pyrazol-1-yl, pyrazol-3-yl, pyrazol-5-yl), isoxazolyl (e.g. isoxazol-3-yl, isoxazol-4-yl, isoxazol-5-yl), isothiazolyl (e.g. isothiazol-3-yl, isothiazol-4-yl, isothiazol-5-yl), 1,2,3-triazolyl (e.g. 1,2,3-triazol-1-yl, 1,2,3-triazol-4-yl, 1,2,3-triazol-5-yl), 1,2,4-triazolyl(e.g. 1,2,4-triazol-1-yl, 1,2,4-triazol-3-yl, 1,2,4-triazol-5-yl), 1,2,3-oxadiazolyl(e.g. 1,2,3-oxadiazol-4-yl, 1,2,3-oxadiazol-5-yl), 1,2,4-oxadiazolyl (e.g. 1,2,4-oxadiazol-3-yl, 1,2,4-oxadiazol-5-yl), 1,2,5-oxadiazolyl(e.g. 1,2,5-oxa-diazol-3-yl, 1,2,5-oxadiazol-4-yl), 1,3,4-oxadiazolyl(e.g. 1,3,4-oxadiazol-2-yl, 1,3,4-oxadiazol-5-yl), 1,2,3-thiadiazolyl (e.g. 1,2,3-thiadiazol-4-yl, 1,2,3-thiadiazol-5-yl), 1,2,4-thiadiazolyl (e.g. 1,2,4-thiadiazol-3-yl, 1,2,4-thiadiazol-5-yl), 1,2,5-thiadiazolyl (e.g. 1,2,5-thiadiazol-3-yl, 1,2,5-thiadiazol-4-yl), 1,3,4-thiadiazolyl(e.g. 1,3,4-thiadiazol-2-yl, 1,3,4-thiadiazol-5-yl), tetrazolyl (e.g. tetrazol-1-yl, tetrazol-5-yl), pyranyl (e.g. pyran-2-yl), pyridinyl (e.g. pyridine-2-yl, pyridine-3-yl, pyridine-4-yl), pyridazinyl (e.g. pyridazin-2-yl, pyridazin-3-yl), pyrimidinyl (e.g. pyrimidin-2-yl, pyrimidin-4-yl, pyrimidin-5-yl), pyrazinyl, 1,2,3-triazinyl, 1,2,4-triazinyl, 1,3,5-triazinyl, thiadiazinyl, azepinyl, azecinyl, and the like. Hetaryl or heteroaryl is also intended to include bicyclic heterocyclic aromatic rings containing one or more heteroatoms selected from nitrogen, oxygen, sulfur, S(=O) and S(=O)$_2$. Representative examples are indolyl (e.g. indol-1-yl, indol-2-yl, indol-3-yl, indol-5-yl), isoindolyl, benzofuranyl (e.g. benzo[b]furan-2-yl, benzo[b]furan-3-yl, benzo[b]furan-5-yl, benzo[c]furan-2-yl, benzo[c]furan-3-yl, benzo[c]furan-5-yl), benzothienyl (e.g. benzo[b]thien-2-yl, benzo[b]thien-3-yl, benzo[b]thien-5-yl, benzo[c]thien-2-yl, benzo[c]thien-3-yl, benzo[c]thien-5-yl), indazolyl (e.g. indazol-1-yl, indazol-3-yl, indazol-5-yl), indolizinyl (e.g. indolizin-1-yl, indolizin-3-yl), benzopyranyl (e.g. benzo[b]pyran-3-yl, benzo[b]pyran-6-yl, benzo[c]pyran-1-yl, benzo[c]pyran-7-yl), benzimidazolyl (e.g. benzimidazol-1-yl, benzimidazol-2-yl, benzimidazol-5-yl), benzothiazolyl (e.g. benzothiazol-2-yl, benzothiazol-5-yl), benzisothiazolyl, benzoxazolyl, benzisoxazolyl, benzoxazinyl, benzotriazolyl, naphthyridinyl (e.g. 1,8-naphthyridin-2-yl, 1,7-naphthyridin-2-yl, 1,6-naphthyridin-2-yl), phthalazinyl (e.g. phthalazin-1-yl, phthalazin-5-yl), pteridinyl, purinyl (e.g. purin-2-yl, purin-6-yl, purin-7-yl, purin-8-yl, purin-9-yl), quinazolinyl (e.g. quinazolin-2-yl, quinazolin-4-yl, quinazolin-6-yl), cinnolinyl, quinoliny (e.g. quinolin-2-yl, quinolin-3-yl, quinolin-4-yl, quinolin-6-yl), iso-quinolinyl (e.g. isoquinolin-1-yl, isoquinolin-3-yl, isoquinolin-4-yl), quinoxalinyl (e.g. quinoxalin-2-yl, quinoxalin-5-yl), pyrrolopyridinyl (e.g. pyrrolo[2,3-b]pyridinyl, pyrrolo[2,3-c]pyridinyl, pyrrolo[3,2-c]pyridinyl), furopyridinyl (e.g. furo[2,3-b]pyridinyl, furo[2,3-c]pyridinyl, furo[3,2-c]pyridinyl), thienopyridinyl (e.g. thieno[2,3-b]pyridinyl, thieno[2,3-c]pyridinyl, thieno[3,2-c]pyridinyl), imidazopyridinyl (e.g. imidazo[4,5-b]pyridinyl, imidazo[4,5-c]pyridinyl, imidazo[1,5-a]pyridinyl, imidazo[1,2-a]pyridinyl), imidazopyrimidinyl (e.g. imidazo[1,2-a]pyrimidinyl, imidazo[3,4-a]pyrimidinyl), pyrazolopyridinyl (e.g. pyrazolo[3,4-b]pyridinyl, pyrazolo[3,4-c]pyridinyl, pyrazolo[1,5-a]pyridinyl), pyrazolopyrimidinyl (e.g. pyrazolo[1,5-a]pyrimidinyl, pyrazolo[3,4-d]pyrimidinyl), thiazolopyridinyl (e.g. thiazolo[3,2-d]pyridinyl), thiazolopyrimidinyl (e.g. thiazolo[5,4-d]pyrimidinyl), imdazothiazolyl (e.g. imidazo[2,1-b]thiazolyl), triazolopyridinyl (e.g. triazolo[4,5-b]pyridinyl), triazolopyrimidinyl (e.g. 8-azapurinyl), and the like. Hetaryl or heteroaryl is also intended to include polycyclic heterocyclic aromatic rings containing one or more heteroatoms selected from nitrogen, oxygen, sulfur, S(=O) and S(=O)$_2$. Representative examples are carbazolyl (e.g. carbazol-2-yl, carbazol-3-yl, carbazol-9-yl), phenoxazinyl (e.g. phenoxazin-10-yl), phenazinyl (e.g. phenazin-5-yl), acridinyl (e.g. acridin-9-yl, acridin-10-yl), phenothiazinyl (e.g. phenothiazin-10-yl), carbolinyl (e.g. pyrido-[3,4-b]indol-1-yl, pyrido[3,4-b]indol-3-yl), phenanthrolinyl (e.g. phenanthrolin-5-yl), and the like. Hetaryl or heteroaryl is also intended to include partially saturated monocyclic, bicyclic or polycyclic heterocyclic rings containing one or more heteroatoms selected from nitrogen, oxygen, sulfur, S(=O) and S(=O)$_2$. Representative examples are pyrrolinyl, pyrazolinyl, imidazolinyl (e.g. 4,5-dihydroimidazol-2-yl, 4,5-dihydroimidazol-1-yl), indolinyl (e.g. 2,3-dihydro-indol-1-yl, 2,3-dihydroindol-5-yl), dihydrobenzofuranyl (e.g. 2,3-dihydrobenzo[b]furan-2-yl, 2,3-dihydrobenzo[b]furan-4-yl), dihydrobenzothienyl (e.g. 2,3-dihydrobenzo[b]thien-2-yl, 2,3-dihydrobenzo[b]thien-5-yl), 4,5,6,7-tetrahydrobenzo[b]furan-5-yl), dihydrobenzopyranyl (e.g. 3,4-dihydrobenzo[b]pyran-3-yl, 3,4-dihydrobenzo[b]pyran-6-yl, 3,4-dihydrobenzo[c]pyran-1-yl, dihydrobenzo[c]pyran-7-yl), oxazolinyl (e.g. 4,5-dihydrooxazol-2-yl, 4,5-dihydrooxazol-4-yl, 4,5-dihydrooxazol-5-yl), isoxazolinyl, oxazepinyl, tetrahydroindazolyl (e.g. 4,5,6,7-tetrahydro-indazol-1-yl, 4,5,6,7-tetrahydroindazol-3-yl, 4,5,6,7-tetrahydroindazol-4-yl, 4,5,6,7-tetra-hydroindazol-6-yl), tetrahydrobenzimidazolyl (e.g. 4,5,6,7-tetrahydrobenzimidazol-1-yl, 4,5,6,7-tetrahydrobenzimidazol-5-yl), tetrahydroimidazo[4,5-c]pyridyl (e.g. 4,5,6,7-tetrahydroimidazo[4,5-c]pyrid-1-yl, 4,5,6,7-tetrahydroimidazo[4,5-c]pyrid-5-yl, 4,5,6,7-tetrahydroimidazo[4,5-c]pyrid-6-yl), tetrahydroquinolinyl (e.g. 1,2,3,4-tetrahydroquinolinyl, 5,6,7,8-tetrahydroquinolinyl), tetrahydroisoquinolinyl (e.g. 1,2,3,4-tetrahydroisoquinolinyl, 5,6,7,8-tetrahydroisoquinolinyl), tetrahydroquinoxalinyl (e.g. 1,2,3,4-tetrahydroquinoxalinyl, 5,6,7,8-tetrahydroquinoxalinyl), and the like. Hetaryl or heteroaryl is also intended to include partially saturated bicyclic or polycyclic heterocyclic rings containing one or more spiro atoms. Representative examples are spiro[isoquinoline-3,1'-cyclohexan]-1-yl, spiro[piperidine-4,1'-benzo-[c]thiophen]-1-yl, spiro[piperidine-4, 1'-benzo[c]furan]-1-yl, spiro[piperidine-4,3'-benzo[b]furan]-1-yl, spiro[piperidine-4,3'-coumarin]-1-yl, and the like.

The term "monocyclic hetaryl" or "monocyclic heteroaryl" as used herein is intended to include monocyclic heterocyclic aromatic rings as defined above.

The term "bicyclic hetaryl" or "bicyclic heteroaryl" as used herein is intended to include bicyclic heterocyclic aromatic rings as defined above.

The term "optionally substituted" as used herein means that the groups in question are either unsubstituted or substituted with one or more of the substituents specified. When the groups in question are substituted with more than one substituent the substituents may be the same or different.

Certain of the above defined terms may occur more than once in the structural formulae, and upon such occurrence each term shall be defined independently of the other.

Certain of the defined terms may occur in combinations, and it is to be understood that the first mentioned radical is a substituent on the subsequently mentioned radical, where the point of substitution, i.e. the point of attachment to another part of the molecule, is on the last mentioned of the radicals.

The term "treatment" is defined as the management and care of a patient for the purpose of combating or alleviating the disease, condition or disorder, and the term includes the administration of the active compound to prevent the onset of the symptoms or complications, or alleviating the symptoms or complications, or eliminating the disease, condition, or disorder.

The term "pharmaceutically acceptable" is defined as being suitable for administration to humans without adverse events.

The term "prodrug" is defined as a chemically modified form of the active drug, said prodrug being administered to the patient and subsequently being converted to the active drug. Techniques for development of prodrugs are well known in the art.

DETAILED DESCRIPTION OF THE INVENTION

The present invention is based on the observation that the compounds of the general formulas (I) disclosed below are able to modulate or inhibit the activity of 11βHSD1.

Accordingly, the present invention is concerned with compounds or prodrugs thereof of the general formula (I)

(I)

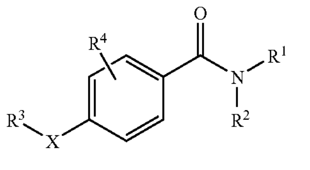

wherein $R^1$ and $R^2$ together with the nitrogen to which they are attached, are forming a 8-11 membered saturated or partially saturated bicyclic or tricyclic ring consisting of the shown nitrogen, 5-10 carbon atoms and from 0 to 1 additional heteroatom selected from nitrogen, oxygen, and $S(O)_m$, where m is 0, 1 or 2, and said ring being substituted with 0 to 3 groups independently selected from $C_1$-$C_4$alkyl, halogen, hydroxy, oxo, COOH, —$NHR^7$, $NR^7R^8$, —$S(O)_2C_1$-$C_4$alkyl, —$S(O)_2NR^7R^8$, $C_1$-$C_4$alkyloxy, $C_1$-$C_4$alkyloxy, $C_1$-$C_4$alkyl and $C_1$-$C_4$alkylcarbonyl, wherein each alkyl group is substituted with 0 to 1 $R^{18}$, or $R^1$ is hydrogen, $C_1$-$C_4$alkyl or cyclopropyl and $R^2$ is adamantyl optionally substituted with 0 to 1 $R^{18}$;

$R^3$ is selected from -1,2-cyclopentyl-$R^9$, -1,3-cyclopentyl-$R^9$, -1,4-cyclohexyl-$R^9$, —$CH_2$-1,4-cyclohexyl-$R^9$, -1,3-cyclohexyl-$R^9$, —$CH_2$-1,3-cyclohexyl-$R^9$, -3-pyrrolidin-1-yl-$R^{10}$, —$CH_2$-3-pyrrolidin-1-$R^{10}$, 4-tetrahydro-pyran, 4-tetrahydro-pyran-2-yl-$R^9$, 4-tetrahydro-pyran-3-yl-$R^9$, -4-piperidin-1-yl-$R^{11}$, —$CH_2$-4-piperidin-1-yl-$R^{11}$, -3-piperidin-1-yl-$R^{11}$, —$CH_2$-3-piperidin-1-yl-$R^{11}$, -4-bicyclo[2.2.2]octan-1-yl-$R^{12}$ and —$CH_2$-4-bicyclo[2.2.2]octan-1-yl-$R^{12}$;

X is selected from —O—, —$S(O)_n$—, —$CR^5R^6$—, and —$NR^7$—; or $R^3$ and $R^7$ are connected by a covalent bond so as to form a bicyclic or tricyclic hetcycloalkyl ring comprising the N to which $R^3$ and $R^7$ are connected; the hetcycloalkyl ring may further be substituted with one or more $R^{19}$;

$R^4$ is selected from hydrogen, $C_1$-$C_4$alkyl, trifluoromethyl, halogen, $C_1$-$C_4$alkyloxy, $C_1$-$C_4$alkyl-oxy$C_1$-$C_4$alkyl and $C_1$-$C_4$alkylcarbonyl, wherein each alkyl group is substituted with 0 to 1 $R^{18}$;

$R^5$ and $R^6$ independently are selected from hydrogen, fluorine, methyl, ethyl, iso-propyl or cyclopropyl;

$R^7$ is selected from hydrogen or selected from $C_1$-$C_6$alkyl, $C_1$-$C_6$alkenyl, $C_1$-$C_6$alkynyl, cycloalkyl, aryl or hetaryl, each of which may be substituted with 0 to 2 $R^{19}$;

$R^8$ is selected from $C_1$-$C_6$alkyl, $C_1$-$C_6$alkenyl, $C_1$-$C_6$alkynyl, cycloalkyl, hetcycloalkyl, aryl or hetaryl, each of which may be substituted with 0 to 2 $R^{19}$; or $R^7$ and $R^8$ optionally are connected by a covalent bond so as to form a ring comprising the N to which $R^7$ and $R^8$ are connected; the ring may further be substituted with one or more $R^{19}$;

$R^9$ and $R^{12}$ independently are selected from hydroxy, cyano, $C(O)R^{13}$, —$(CR^{14}R^{15})_nC(O)NR^7R^8$, —$(CR^{14}R^{15})_nNHC(O)R^{16}$, —$(CR^{14}R^{15})_nOR^{16}$, —$(CR^{14}R^{15})_nS(O)_mR^{16}$, —$(CR^{14}R^{15})_nS(O)_2NR^7R^8$, —$(CR^{14}R^{15})_nNR^7R^8$, —$(CR^{14}R^{15})_nNR^{17}C(O)NR^7R^8$, —$(CR^{14}R^{15})_nNR^{17}S(O)_2R^{16}$, —$(CR^{14}R^{15})_nC{=}C$—$R^{16}$, —$(CR^{14}R^{15})_nC{\equiv}C$—$R^{16}$, —$(CR^{14}R^{15})_n$aryl substituted with 0 to 2 $R^{20}$, and —$(CR^{14}R^{15})_n$hetaryl optionally substituted with 0 to 2 $R^{19}$;

$R^{10}$ and $R^{11}$ independently are selected from —$C(O)NR^7R^8$, —$CH_2C(O)NR^7R^8$, —$C(O)R^{17}$, —$S(O)_2R^{16}$ or —$S(O)_2NR^7R^8$, wherein the alkyl, aryl and hetaryl groups are optionally substituted with 0 to 2 $R^{19}$;

m and n independently are 0, 1 or 2;

$R^{13}$ is selected from hydroxy, $C_1$-$C_6$alkyl, $C_1$-$C_6$alkenyl, $C_1$-$C_6$alkynyl, cycloalkyl, $C_1$-$C_6$alkyloxy, aryl, aryloxy, aryl$C_1$-$C_6$alkyloxy, hetaryl, hetaryloxy or hetaryl$C_1$-$C_6$alkyloxy wherein the $C_1$-$C_6$alkyl, cycloalkyl, aryl or hetaryl groups are optionally substituted with one or more $R^{19}$;

$R^{14}$ and $R^{15}$ independently are selected from hydrogen, halogen, $C_1$-$C_6$alkyl and cycloalkyl, each of which $C_1$-$C_6$alkyl and cycloalkyl may be substituted with 0 to 2 halogen, hydroxy or oxo and the carbon in $CR^{14}R^{15}$ can together with the $R^{14}$ and/or $R^{15}$ groups be part of a cycloalkyl ring;

$R^{16}$ is selected from hydrogen, $C_1$-$C_6$alkyl, $C_1$-$C_6$alkenyl, $C_1$-$C_6$alkynyl, cycloalkyl, hetcycloalkyl, aryl or hetaryl wherein the $C_1$-$C_6$alkyl, cycloalkyl, aryl or hetaryl groups are optionally substituted with one or more $R^{19}$;

$R^{17}$ is selected from hydrogen, $C_1$-$C_6$alkyl, $C_1$-$C_6$alkylC(O)$R^{20}$, —$(CR^{14}R^{15})_nNR^{17}S(O)_2R^{16}$, cycloalkyl, hetcycloalkyl, aryl or hetaryl, wherein the alkyl, cycloalkyl, hetcycloalkyl, aryl and hetaryl groups optionally are substituted with one or more $R^{21}$;

$R^{18}$ is halogen, hydroxy, oxo, —$S(O)_2C_1$-$C_4$alkyl, —$S(O)_2NR^7R^9$ or —$C(O)R^{13}$;

$R^{19}$ is selected from halogen, hydroxy, oxo, —C(O)$R^{20}$, $C_1$-$C_6$alkylC(O)$R^{20}$, —$S(O)_n R^{16}$, —$S(O)_n NR^7R^8$, cyclopropyl, —$OR^{16}$, $C_1$-$C_6$alkyl, aryl, hetaryl, —$NR^{22}C(O)NR^7R^8$, —$NR^{22}S(O)_2NR^7R^8$ or —NC(O)NHS$(O)_2R^{16}$;

$R^{20}$ is selected from hydroxy, $C_1$-$C_6$alkyl, $C_1$-$C_6$alkenyl, $C_1$-$C_6$alkynyl, cycloalkyl, $C_1$-$C_6$alkyloxy, aryl, aryloxy, aryl$C_1$-$C_6$alkyloxy, hetaryl, hetaryloxy or hetaryl$C_1$-$C_6$alkyloxy;

$R^{21}$ is halogen, cyano or hydroxy; or a salt thereof with a pharmaceutically acceptable acid or base, or any optical isomer or mixture of optical isomers, including a racemic mixture, or any tautomeric forms.

In one embodiment of the present invention, in formula (I), n is 0.

In another embodiment of the present invention, in formula (I), $R^{14}$ and $R^{15}$ are both hydrogen.

In another embodiment of the present invention, in formula (I), n is 1.

In another embodiment of the present invention, in formula (I), $R^7$ and $R^8$ are connected by a covalent bond so as to form a pyrrolidine, a piperidine, a piperazine, a substituted pyrrolidine, a substituted piperidine or a substituted piperazine.

In another embodiment of the present invention, in formula (I), $R^7$ and $R^8$ are connected by a covalent bond so as to form a piperidine, a piperazine, a substituted piperidine or a substituted piperazine.

In another embodiment of the present invention, in formula (I), $R^4$ is hydrogen.

In another embodiment of the present invention, in formula (I), $R^1$ and $R^2$ together with the nitrogen to which they are attached, are forming a 8-11 membered saturated or partially saturated bicyclic or tricyclic ring, said ring being selected from the group consisting of

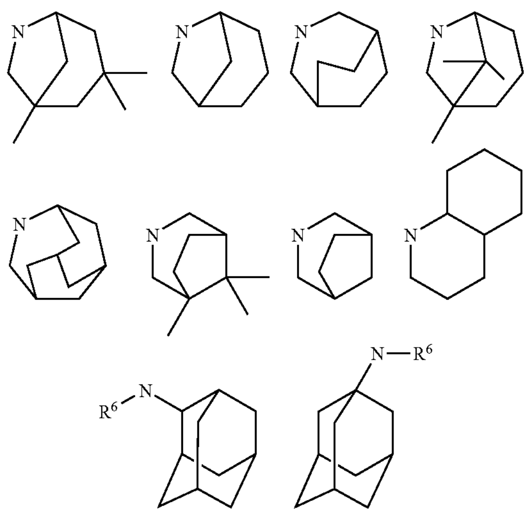

where each carbon is substituted with 0 to 2 $R^{22}$, and $R^{22}$ is independently selected from $C_1$-$C_8$alkyl, halogen, hydroxy, oxo, C(O)$R^{13}$, —$S(O)_2NR^7R^8$, —$S(O)_n C_1$-$C_4$alkyl and $C_1$-$C_6$alkyloxy.

In another embodiment of the present invention, in formula (I), X is —O—.

In another embodiment of the present invention, in formula (I), X is —$NR^7$—.

In another embodiment of the present invention, in formula (I) $R^3$ and $R^7$ are connected by a covalent bond so as to form a bicyclic or tricyclic hetcycloalkyl ring comprising the N to which $R^3$ and $R^7$ are connected wherein the hetcycloalkyl ring may further be substituted with one or more $R^{19}$.

In another embodiment of the present invention, in formula (I) $R^3$ and $R^7$ together with the N to which they are connected comprises 2-Oxa-5-aza-bicyclo[2.2.1]hept-5-yl, 2,5-diaza-bicyclo[2.2.1]heptane-2-carboxylic acid tert-butyl ester or (1S,5R)-3-(pyridin-2-yloxy)-8-aza-bicyclo[3.2.1]oct-8-yl.

In another embodiment of the present invention, in formula (I), $R^3$ is -1,4-cyclohexyl-$R^9$ or —$CH_2$-1,4-cyclohexyl-$R^9$.

In another embodiment of the present invention, in formula (I), $R^9$ is C(O)$R^{13}$.

In another embodiment of the present invention, in formula (I), $R^{13}$ is hydroxy.

In another embodiment of the present invention, in formula (I), $R^9$ is selected from —$CH_2$—O-aryl, —$CH_2$—O-hetaryl, —O-aryl, —O-hetaryl, —$CH_2$—O—$C_{1-6}$alkyl, —NHC(O)$R^{16}$, where the aryl, hetaryl and $C_{1-6}$alkyl groups are optionally substituted.

In another embodiment of the present invention, in formula (I), $R^9$ is selected from —NH—$S(O)_2$-aryl, —NH—$S(O)_2$-hetaryl, —NH-aryl, —NH-hetaryl, —$S(O)_2$-aryl and —$S(O)_2$-hetaryl, where the aryl and hetaryl groups are optionally substituted.

In another embodiment of the present invention, in formula (I), $R^3$ is -1,3-cyclohexyl-$R^9$ or —$CH_2$-1,3-cyclohexyl-$R^9$.

In another embodiment of the present invention, in formula (I), $R^3$ comprises a cyclohexyl ring and $R^9$ or $R^{12}$ is attached in the cis-configuration.

In another embodiment of the present invention, in formula (I), $R^3$ comprises a cyclohexyl ring and $R^9$ or $R^{12}$ is attached in the trans-configuration.

In another embodiment of the present invention, in formula (I), $R^3$ is -4-piperidin-1-yl-$R^{11}$ or —$CH_2$-4-piperidin-1-yl-$R^{11}$.

In another embodiment of the present invention, in formula (I), $R^{11}$ is selected from aryl, hetaryl, —$S(O)_2$-aryl and —$S(O)_2$-hetaryl, where each aryl and hetaryl groups are optionally substituted.

In another embodiment of the present invention, in formula (I), $R^3$ is -3-piperidin-1-yl-$R^{11}$ or —$CH_2$-3-piperidin-1-yl-$R^{11}$.

In another embodiment of the present invention, in formula (I), $R^1$ is hydrogen, $C_1$-$C_4$alkyl or cyclopropyl.

In another embodiment of the present invention, in formula (I), $R^2$ is an adamantyl substituted with one, two or more substituents independently selected from halogen, hydroxy, oxo, C(O)$R^{13}$, $C_1$-$C_6$alkyl, $C_1$-$C_6$alkyloxy, —$S(O)_2NR^7R^8$, and —$S(O)_n C_1$-$C_4$alkyl.

In another embodiment of the present invention, in formula (I), $R^1$ and $R^2$ together with the nitrogen to which they are attached, are forming a substituted 8-aza-bicyclo[3.2.1]-octane.

In another embodiment of the present invention, in formula (I), $R^1$ and $R^2$ together with the nitrogen to which they are attached, is 8-aza-bicyclo[3.2.1]octan-3-yl.

In another embodiment of the present invention, in formula (I), $R^1$ and $R^2$ together with the nitrogen to which they are attached, are forming 8-aza-bicyclo[3.2.1]octane substituted with one, two or more substituents independently selected from halogen, hydroxy, oxo, C(O)R13, $C_1$-$C_6$alkyl, $C_1$-$C_6$alkyloxy, —$S(O)_2NR^7R^8$ and —$S(O)_n C_1$-$C_4$alkyl.

In another embodiment of the present invention, the compound of formula (I) is (I)

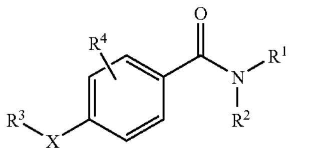

wherein $R^1$ and $R^2$ together with the nitrogen to which they are attached, are forming a 8-11 membered saturated or partially saturated bicyclic or tricyclic ring consisting of the shown nitrogen, 5-10 carbon atoms and from 0 to 1 additional heteroatoms selected from nitrogen, oxygen, and $S(O)_m$, where m is 0, 1 or 2, and said ring being substituted with 0 to 3 groups independently selected from $C_1$-$C_4$alkyl, halogen, hydroxy, oxo, COOH, —$NHR^{17}$, $NR^{17}R^{17}$, $C_1$-$C_4$alkyloxy, $C_1$-$C_4$alkyloxy$C_1$-$C_4$alkyl and $C_1$-$C_4$alkylcarbonyl, wherein each alkyl group is substituted with 0 to 1 $R^{21}$, or $R^1$ is hydrogen, $C_1$-$C_4$alkyl or cyclopropyl and $R^2$ is a substituted or unsubstituted adamantyl;

$R^{21}$ is halogen, hydroxy, oxo or COOH;

$R^4$ is selected from hydrogen, $C_1$-$C_4$alkyl, trifluoromethyl, halogen, $C_1$-$C_4$alkyloxy, $C_1$-$C_4$alkyloxy$C_1$-$C_4$alkyl and $C_1$-$C_4$alkylcarbonyl, wherein each alkyl group is substituted with 0 to 1 $R^{21}$;

X is selected from —O—, —S—, —$CR^5R^6$—, —NH—, and —$NR^6$—;

$R^5$ is hydrogen or fluorine;

$R^6$ is hydrogen, methyl, ethyl, iso-propyl or cyclo-propyl;

$R^3$ is selected from -1,4-cyclohexyl-$R^7$, —$CH_2$-1,4-cyclohexyl-$R^8$, -1,3-cyclohexyl-$R^9$, —$CH_2$-1,3-cyclohexyl-$R^{10}$, -4-piperidin-1-yl-$R^{11}$, —$CH_2$-4-piperidin-1-yl-$R^{12}$, -3-piperidin-1-yl-$R^{13}$, —$CH_2$-3-piperidin-1-yl-$R^{14}$, -4-bicyclo[2.2.2]octan-1-yl-$R^{16}$ and —$CH_2$-4-bicyclo[2.2.2]octan-1-yl-$R^{16}$;

$R^7$, $R^8$, $R^9$, $R^{10}$, $R^{15}$ and $R^{16}$ are independently selected from $CO_2NR^{22}R^{23})_n$—C(O)—$NR^{17}R^{18}$, —$(CR^{22}R^{23})_n$—NHC(O)$R^{18}$, —$(CR^{22}R^{23})_n$—$OR^{18}$, —$(CR^{22}R^{23})_n$—$SR^{18}$, C(O)$R^{19}$, OH, —(C, —$(CR^{22}$—$R^{23})_n$—$S(O)_2R^{18}$, —$(CR^{22}R^{23})_n$—$S(O)_2NR^{17}R^{18}$, —$(CR^{22}R^{23})_n$—$NR^{17}R^{18}$, —$(CR^{22}R^{23})_n$—$NR^{17}C(O)$—$NR^{17}R^{18}$, —$(CR^{22}R^{23})_n$—C═C—$R^{18}$, —$(CR^{22}R^{23})_n$—C≡C—$R^{18}$, —$(CR^{22}R^{23})_n$-aryl substituted with 0 to 2 $R^{20}$, and —$(CR^{22}R^{23})_n$-hetaryl substituted with 0 to 2 $R^{20}$;

n is 0, 1 or 2;

each $R^{22}$ and $R^{23}$ are independently selected from hydrogen, halogen, $C_1$-$C_6$alkyl and cycloalkyl, each of which $C_1$-$C_6$alkyl and cycloalkyl may be substituted with 0 to 2 halogen, hydroxy or oxo and the carbon in $CR^{22}R^{23}$ can together with the $R^{22}$ and/or $R^{23}$ groups be part of a cycloalkyl ring;

$R^{20}$ is selected from halogen, hydroxy, oxo, —COOH, —$S(O)_{0-2}R^{19}$, —$S(O)_{0-2}NR^{19}R^{19}$, cyclopropyl, —O—$R^{19}$, $C_1$-$C_6$alkyl, aryl, hetaryl, $NR^{19}CONR^{19}R^{19}$; $NR^{19}SO_2NR^{19}R^{19}$ or $NCONHSO_2R^{19}$;

$R^{17}$ is selected from hydrogen or selected from $C_1$-$C_6$alkyl, $C_1$-$C_6$alkenyl, $C_1$-$C_6$alkynyl, cycloalkyl, aryl or hetaryl, each of which may be substituted with 0 to 2 $R^{20}$;

$R^{18}$ is selected from $C_1$-$C_6$alkyl, $C_1$-$C_6$alkenyl, $C_1$-$C_6$alkynyl, cycloalkyl, aryl or hetaryl, each of which may be substituted with 0 to 2 $R^{20}$;

where $R^{17}$ and $R^{18}$ are optionally connected by a covalent bond so as to form a ring comprising the N to which $R^{17}$ and $R^{18}$ are connected;

$R^{19}$ is selected from hydrogen, hydroxy, $C_1$-$C_6$alkyl, $C_1$-$C_6$alkenyl, $C_1$-$C_6$alkynyl, cycloalkyl, $C_1$-$C_6$alkyloxy, aryl or hetaryl wherein hydroxy, $C_1$-$C_6$alkyl, cycloalkyl, $C_1$-$C_6$alkyloxy, aryl or hetaryl are optional substituted with $R^{20}$;

$R^{11}$, $R^{12}$, $R^{13}$ and $R^{14}$ are independently selected from —C(O)—$NR^{17}R^{18}$, —$CH_2C(O)$—$NR^{17}R^{18}$, —C(O)$R^{19}$, —$S(O)_2R^{18}$, —$S(O)_2NR^{17}R^{18}$, $C_1$-$C_6$alkyl substituted with 0 to 2 $R^{20}$, aryl substituted with 0 to 2 $R^{20}$, and hetaryl substituted with 0 to 2 $R^{20}$; or a salt thereof with a pharmaceutically acceptable acid or base, or any optical isomer or mixture of optical isomers, including a racemic mixture, or any tautomeric forms.

In formula (I) $R^3$ is understood to be selected from the group

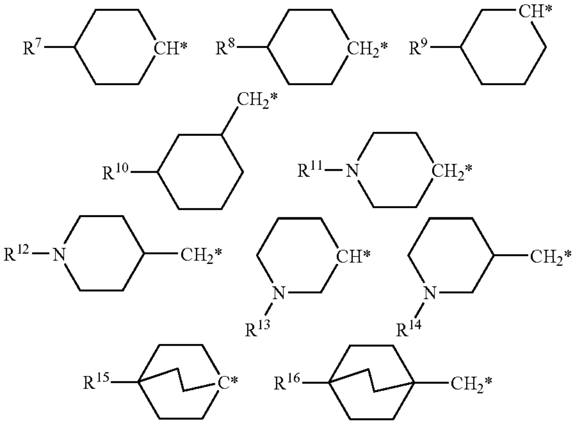

where * indicates the carbon whereto X is bound.

In one embodiment of the present invention, in formula (I) n is 0.

In another embodiment of the present invention, in formula (I) $R^{22}$ and $R^{23}$ are both hydrogen.

In another embodiment of the present invention, in formula (I) n is 1.

In another embodiment of the present invention, in formula (I) n is 1 and both $R^{22}$ and $R^{23}$ are hydrogen.

In another embodiment of the present invention, in formula (I) $R^{17}$ and $R^{18}$ are connected by a covalent bond so as to form a piperidine, a piperazine, a substituted piperidine or a substituted piperazine.

In another embodiment of the present invention, in formula (I) $R^{17}$ and $R^{18}$ are connected by a covalent bond so as to form a piperidine or a substituted piperidine.

In another embodiment of the present invention, in formula (I) $R^4$ is hydrogen.

In another embodiment of the present invention, in formula (I) $R^1$ and $R^2$ together with the nitrogen to which they are attached, are forming a 8-11 membered saturated or partially saturated bicyclic or tricyclic ring consisting of the shown nitrogen, 5-10 carbon atoms and from 0 to 1 additional heteroatoms selected from nitrogen, oxygen, and $S(O)_m$, where m is 0, 1 or 2.

In another embodiment of the present invention, in formula (I) $R^1$ and $R^2$ together with the nitrogen to which they are attached, are forming a 8-11 membered saturated or partially saturated bicyclic or tricyclic ring, said ring being selected from the group consisting of

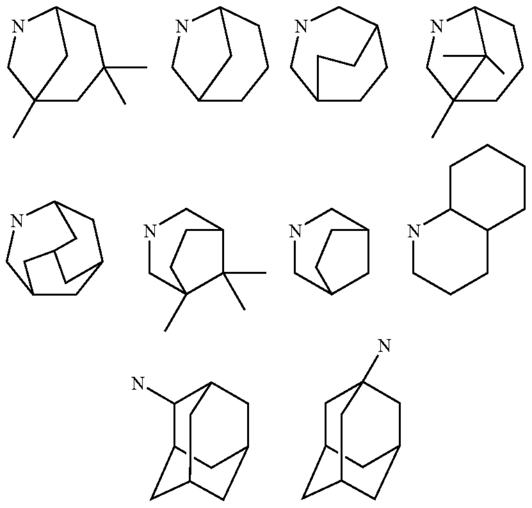

where each is substituted with 0 to 2 $R^{25}$, and $R^{25}$ is independently selected from $C_1$-$C_8$alkyl, halogen, hydroxy, oxo, COOH, and $C_1$-$C_6$alkyloxy.

In another embodiment of the present invention, in formula (I) $R^1$ and $R^2$ together with the nitrogen to which they are attached, are forming a 8-11 membered saturated or partially saturated bicyclic or tricyclic ring, said ring being selected from the group consisting of

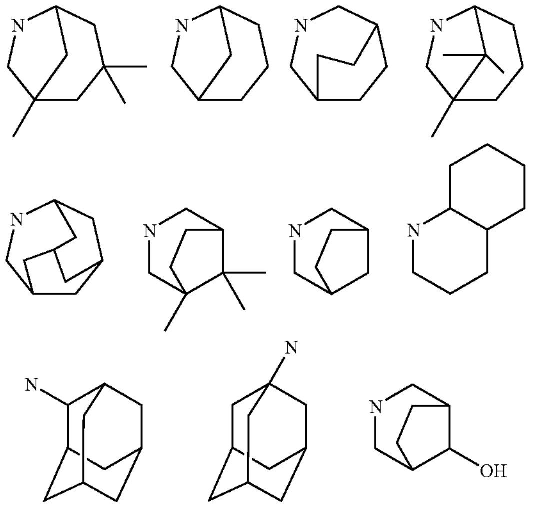

In another embodiment of the present invention, in formula (I) X is —O—.

In another embodiment of the present invention, in formula (I) X is —S—.

In another embodiment of the present invention, in formula (I) X is —$CR^5R^6$—.

In another embodiment of the present invention, in formula (I) X is —NH—.

In another embodiment of the present invention, in formula (I) X is —$NR^6$—.

In another embodiment of the present invention, in formula (I) $R^5$ is hydrogen.

In another embodiment of the present invention, in formula (I) $R^6$ is hydrogen.

In another embodiment of the present invention, in formula (I) X is —$CH_2$—.

In another embodiment of the present invention, in formula (I) $R^3$ is -1,4-cyclohexyl-$R^7$ or —$CH_2$-1,4-cyclohexyl-$R^8$.

In another embodiment of the present invention, in formula (I) $R^7$ and $R^8$ are $C(O)R^{19}$.

In another embodiment of the present invention, in formula (I) $R^{19}$ is hydroxy.

In another embodiment of the present invention, in formula (I) $R^7$ and $R^8$ are selected from —$CH_2$—O-aryl, —$CH_2$—O-hetaryl, —O-aryl, —O-hetaryl, —$NHC(O)R^{18}$, where the aryl, hetaryl and $C_{1-6}$alkyl groups are optionally substituted.

In another embodiment of the present invention, in formula (I) $R^7$ and $R^8$ are selected from —NH—$S(O)_2$-aryl, —NH—$S(O)_2$-hetaryl, —NH-aryl, —NH-hetaryl, —$S(O)_2$-aryl and —$S(O)_2$-hetaryl, where the aryl and hetaryl groups are optionally substituted.

In another embodiment of the present invention, in formula (I) $R^3$ is -1,3-cyclohexyl-$R^9$ or —$CH_2$-1,3-cyclohexyl-$R^{10}$.

In another embodiment of the present invention, in formula (I) $R^3$ comprises a cyclohexyl ring and $R^7$, $R^8$, $R^9$ or $R^{10}$ is attached in the cis-configuration.

In another embodiment of the present invention, in formula (I) $R^3$ comprises a cyclohexyl ring and $R^7$, $R^8$, $R^9$ or $R^{10}$ is attached in the trans-configuration.

In another embodiment of the present invention, in formula (I) $R^3$ is -4-piperidin-1-yl-$R^{11}$ or —$CH_2$-4-piperidin-1-yl-$R^{12}$.

In another embodiment of the present invention, in formula (I) $R^{11}$ and $R^{12}$ are selected from aryl, hetaryl, —$S(O)_2$-aryl and —$S(O)_2$-hetaryl, where each aryl and hetaryl groups are optionally substituted.

In another embodiment of the present invention, in formula (I) $R^3$ is -3-piperidin-1-yl-$R^{13}$ or —$CH_2$-3-piperidin-1-yl-$R^{14}$.

In another embodiment of the present invention, in formula (I) $R^{20}$ is halogen, hydroxy, oxo, —COOH or cyclopropyl.

In another embodiment of the present invention, in formula (I) $R^1$ is hydrogen, $C_1$-$C_4$alkyl or cyclopropyl.

In another embodiment of the present invention, in formula (I) $R^2$ is an unsubstituted adamantyl selected from 1-adamantyl and 2-adamantyl.

In another embodiment of the present invention, in formula (I) $R^2$ is a substituted adamantyl.

In another embodiment of the present invention, in formula (I) $R^2$ is a substituted 1-adamantyl or a substituted 2-adamantyl.

In another embodiment of the present invention, in formula (I) $R^2$ is an adamantyl substituted with one, two or more substituent independently selected from halogen, hydroxy, oxo, COOH, $C_1$-$C_6$alkyl and $C_1$-$C_6$alkyloxy.

In another embodiment of the present invention, the compound of formula (I) is (I)

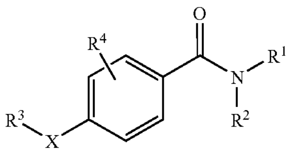

wherein $R^1$ and $R^2$ together with the nitrogen to which they are attached, are forming a 8-11 membered saturated or partially saturated bicyclic or tricyclic ring consisting of the shown nitrogen, 5-10 carbon atoms and from 0 to 1 additional heteroatoms selected from nitrogen, oxygen, and $S(O)_m$, where m is 0, 1 or 2, and said ring being substituted with 0 to 3 groups independently selected from $C_1$-$C_4$alkyl, halogen, hydroxy, oxo, COOH, —$NHR^{17}$, $NR^{17}R^{17}$, $C_1$-$C_4$alkyloxy, $C_1$-$C_4$alkyloxy$C_1$-$C_4$alkyl and $C_1$-$C_4$alkylcarbonyl, wherein each alkyl group is substituted with 0 to 1 $R^{21}$, or $R^1$ is hydrogen, $C_1$-$C_4$alkyl or cyclopropyl and $R^2$ is a substituted or unsubstituted adamantyl;

$R^{21}$ is halogen, hydroxy, oxo or COOH;

$R^4$ is selected from hydrogen, $C_1$-$C_4$alkyl, trifluoromethyl, halogen, $C_1$-$C_4$alkyloxy, $C_1$-$C_4$alkyloxy$C_1$-$C_4$alkyl and $C_1$-$C_4$alkylcarbonyl, wherein each alkyl group is substituted with 0 to 1 $R^{21}$;

X is selected from —O—, —S—, —$CR^5R^6$—, —NH—, and —$NR^6$—;

$R^5$ is hydrogen or fluorine;

$R^6$ is hydrogen, methyl, ethyl, iso-propyl or cyclo-propyl;

$R^3$ is selected from -1,4-cyclohexyl-$R^7$, —$CH_2$-1,4-cyclohexyl-$R^8$, -1,3-cyclohexyl-$R^9$, —$CH_2$-1,3-cyclohexyl-$R^{10}$, -4-piperidin-1-yl-$R^{11}$, —$CH_2$-4-piperidin-1-yl-$R^{12}$, -3-piperidin-1-yl-$R^{13}$, —$CH_2$-3-piperidin-1-yl-$R^{14}$, -4-bicyclo[2.2.2]octan-1-yl-$R^{16}$ and —$CH_2$-4-bicyclo[2.2.2]octan-1-yl-$R^{16}$;

$R^7$, $R^8$, $R^9$, $R^{10}$, $R^{15}$ and $R^{16}$ are independently selected from $CO_2H$, $C(O)R^{19}$, OH, —($CR^{22}$—$R^{23}$), —C(O)—$NR^{17}R^{18}$, —($CR^{22}R^{23}$), —$NHC(O)R^{18}$, —$(CR^{22}R^{23})_n$—$OR^{18}$, —$(CR^{22}R^{23})_n$—$SR^{18}$, —($CR^{22}$—$R^{23}$), —$S(O)_2R^{18}$, —$(CR^{22}R^{23})_n$—$S(O)_2NR^{17}R^{18}$, —$(CR^{22}R^{23})_n$—$NR^{17}R^{18}$, —$(CR^{22}R^{23})_n$—$NR^{17}C(O)$—$NR^{17}R^{18}$, —$(CR^{22}R^{23})_n$—C≡C—$R_{18}$, —$(CR^{22}R^{23})_n$—C≡C—$R_{18}$, —$(CR^{22}R^{23})_n$-aryl substituted with 0 to 2 $R^{20}$, and —$(CR^{22}R^{23})_n$-hetaryl substituted with 0 to 2 $R^{20}$;

n is 0, 1 or 2;

each $R^{22}$ and $R^{23}$ are independently selected from hydrogen, halogen, $C_1$-$C_6$alkyl and cycloalkyl, each of which $C_1$-$C_6$alkyl and cycloalkyl may be substituted with 0 to 2 halogen, hydroxy or oxo and the carbon in $CR^{22}R^{23}$ can together with the $R^{22}$ and/or $R^{23}$ groups be part of a cycloalkyl ring;

$R^{20}$ is halogen, hydroxy, oxo, —COOH, —$S(O)_{0-2}R^{19}$, —$S(O)_{0-2}NR^{19}R^{19}$, cyclopropyl, —O—$R^{19}$ or $C_1$-$C_6$alkyl;

$R^{17}$ is hydrogen or selected from $C_1$-$C_6$alkyl, cycloalkyl, aryl or hetaryl, each of which may be substituted with 0 to 2 $R^{20}$;

$R^{18}$ is $C_1$-$C_6$alkyl, cycloalkyl, aryl or hetaryl, each of which may be substituted with 0 to 2 $R^{20}$; where $R^{17}$ and $R^{18}$ are optionally connected by a covalent bond so as to form a ring comprising the N to which $R^{17}$ and $R^{18}$ are connected;

$R^{19}$ is selected from hydroxy, $C_1$-$C_6$alkyl, cycloalkyl, $C_1$-$C_6$alkyloxy, aryl or hetaryl wherein hydroxy, $C_1$-$C_6$alkyl, cycloalkyl, $C_1$-$C_6$alkyloxy, aryl or hetaryl are optional substituted with $R^{20}$.

$R^{11}$, $R^{12}$, $R^{13}$ and $R^{14}$ are independently selected from —C(O)—$NR^{17}R^{18}$, —$CH_2C(O)$—$NR^{17}R^{18}$, —$C(O)R^{19}$, —$S(O)_2R^{18}$, —$S(O)_2NR^{17}R^{18}$, $C_1$-$C_6$alkyl substituted with 0 to 2 $R^{20}$, aryl substituted with 0 to 2 $R^{20}$, and hetaryl substituted with 0 to 2 $R^{20}$; or a salt thereof with a pharmaceutically acceptable acid or base, or any optical isomer or mixture of optical isomers, including a racemic mixture, or any tautomeric forms.

In another embodiment of the present invention, the compound of formula (I) is

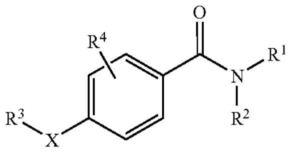

(I)

wherein $R^1$ and $R^2$ together with the nitrogen to which they are attached, are forming a 8-11 membered saturated or partially saturated bicyclic or tricyclic ring consisting of the shown nitrogen, 5-10 carbon atoms and from 0 to 1 additional heteroatoms selected from nitrogen, oxygen, and $S(O)_m$, where m is 0, 1 or 2, and said ring being substituted with 0 to 3 groups independently selected from $C_1$-$C_4$alkyl, halogen, hydroxy, oxo, $C_1$-$C_4$alkyloxy, $C_1$-$C_4$alkyloxy-$C_1$-$C_4$alkyl and $C_1$-$C_4$alkylcarbonyl, wherein each alkyl group is substituted with 0 to 1 $R^{21}$, or $R^1$ is hydrogen, $C_1$-$C_4$alkyl or cyclopropyl and $R^2$ is a substituted or unsubstituted adamantyl;

$R^{21}$ is halogen, hydroxy, oxo or COOH;

$R^4$ is selected from hydrogen, $C_1$-$C_4$alkyl, trifluoromethyl, halogen, $C_1$-$C_4$alkyloxy, $C_1$-$C_4$alkyloxy$C_1$-$C_4$alkyl and $C_1$-$C_4$alkylcarbonyl, wherein each alkyl group is substituted with 0 to 1 $R^{21}$;

X is selected from —O—, —S—, —$CR^5R^6$—, —NH—, and —$NR^6$—;

$R^5$ is hydrogen or fluorine;

$R^6$ is hydrogen, methyl, ethyl, iso-propyl or cyclo-propyl;

$R^3$ is selected from -1,4-cyclohexyl-$R^7$, —$CH_2$-1,4-cyclohexyl-$R^8$, -1,3-cyclohexyl-$R^9$, —$CH_2$-1,3-cyclohexyl-$R^{10}$, -4-piperidin-1-yl-$R^{11}$, —$CH_2$-4-piperidin-1-yl-$R^{12}$, -3-piperidin-1-yl-$R^{13}$, —$CH_2$-3-piperidin-1-yl-$R^{14}$, -4-bicyclo[2.2.2]octan-1-yl-$R^{15}$ and —$CH_2$-4-bicyclo[2.2.2]octan-1-yl-$R^{16}$;

$R^7$, $R^8$, $R^9$, $R^{10}$, $R^{15}$ and $R^{16}$ are independently selected from $CO_2H$, $C(O)R^{19}$, OH, —C(O)—$NR^{17}R^{18}$, —$NHC(O)R^{18}$, —$CH_2NHC(O)R^{18}$, —$OR^{18}$, —$SR^{18}$, —$S(O)_2R^{18}$, —$NR^{17}R^{18}$, —$CH_2OR^{18}$, —$CH_2SR^{18}$, —$CH_2NHR^{18}$, —$C(O)R^{19}$, —$CH_2$—O—$R^{19}$, —$CH_2C(O)$—$NR^{17}R^{18}$, aryl substituted with 0 to 2 $R^{20}$, and hetaryl substituted with 0 to 2 $R^{20}$;

$R^{20}$ is halogen, hydroxy, oxo, COOH or $C_1$-$C_6$alkyl;

$R^{17}$ is hydrogen or selected from $C_1$-$C_6$alkyl, cycloalkyl, aryl or hetaryl, each of which may be substituted with 0 to 2 $R^{20}$;

$R^{18}$ is $C_1$-$C_6$alkyl, cycloalkyl, aryl or hetaryl, each of which may be substituted with 0 to 2 $R^{20}$; where $R^{17}$ and $R^{18}$ are optionally connected by a covalent bond so as to form a ring comprising the N to which $R^{17}$ and $R^{18}$ are connected;

$R^{19}$ is selected from hydroxy, $C_1$-$C_6$alkyl, cycloalkyl, $C_1$-$C_6$alkyloxy, aryl or hetaryl;

$R^{11}$, $R^{12}$, $R^{13}$ and $R^{14}$ are independently selected from —C(O)—$NR^{17}R^{18}$, —$CH_2C(O)$—$NR^{17}R^{18}$, —$C(O)R^{19}$, —$S(O)_2R^{18}$, $C_1$-$C_6$alkyl substituted with 0 to 2 $R^{20}$, aryl substituted with 0 to 2 $R^{20}$, and hetaryl substituted with 0 to 2 $R^{20}$; or a salt thereof with a pharmaceutically acceptable acid or base, or any optical isomer or mixture of optical isomers, including a racemic mixture, or any tautomeric forms

.

In another embodiment of the present invention, the compounds of general formula (I) is selected from the group consisting of

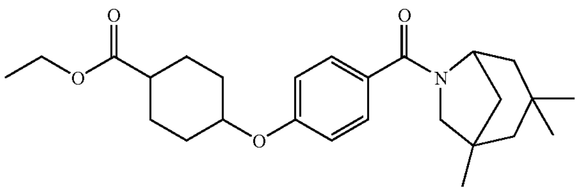

4-[4-(1,3,3-Trimethyl-6-aza-bicyclo[3.2.1]octane-6-carbonyl)-phenoxy]-cyclohexane carboxylic acid ethyl ester,

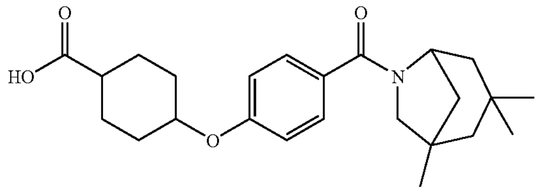

4-[4-(1,3,3-Trimethyl-6-aza-bicyclo[3.2.1]octane-6-carbonyl)-phenoxy]-cyclohexane carboxylic acid,

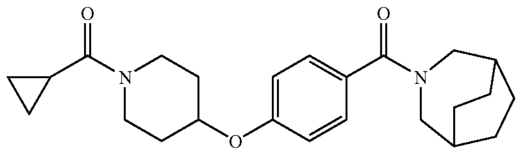

(3-Aza-bicyclo[3.2.2]non-3-yl)-[4-(1-cyclopropanecarbonyl-piperidin-4-yloxy)-phenyl]-methanone,

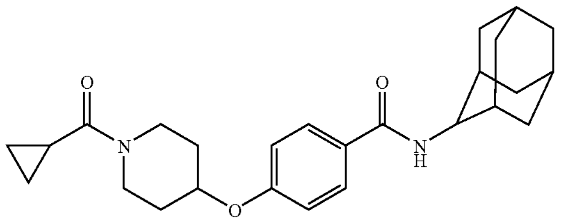

4-(1-Cyclopropanecarbonyl-piperidin-4-yloxy)-N-adamantan-2-yl-benzamide,

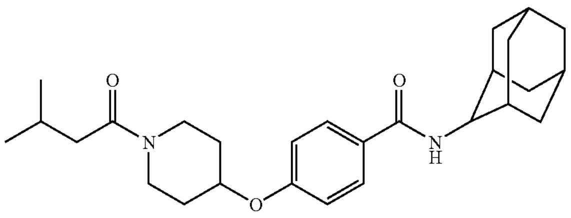

4-[1-(3-Methyl-butyryl)-piperidin-4-yloxy]-N-adamantan-2-yl-benzamide,

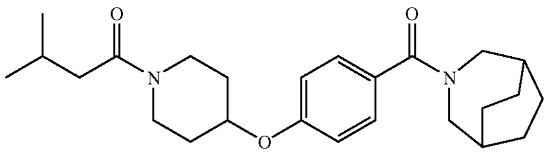

1-{4-[4-(3-Aza-bicyclo[3.2.2]nonane-3-carbonyl)-phenoxy]-piperidin-1-yl}-3-methyl-butan-1-one,

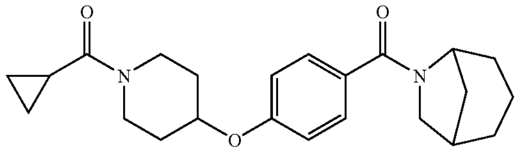

(6-Aza-bicyclo[3.2.1]oct-6-yl)-[4-(1-cyclopropanecarbonyl-piperidin-4-yloxy)-phenyl]-methanone,

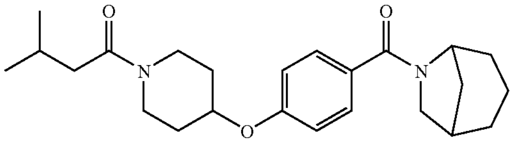

1-{4-[4-(6-Aza-bicyclo[3.2.1]octane-6-carbonyl)-phenoxy]-piperidin-1-yl}-3-methyl-butan-1-one,

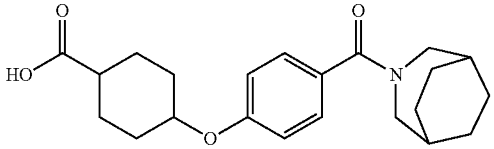

4-[4-(3-Aza-bicyclo[3.2.2]nonane-3-carbonyl)-phenoxy]-cyclohexanecarboxylic acid,

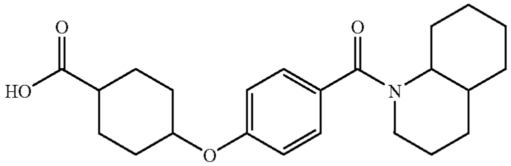

4-[4-(Octahydro-quinoline-1-carbonyl)-phenoxy]-cyclohexanecarboxylic acid,

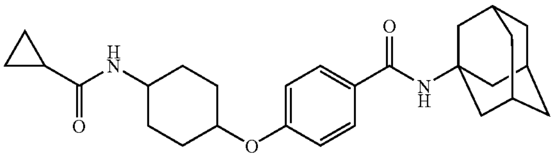

cis/trans-4-[4-(Cyclopropanecarbonyl-amino)-cyclohexyloxy]-N-adamantan-1-yl-benzamide,

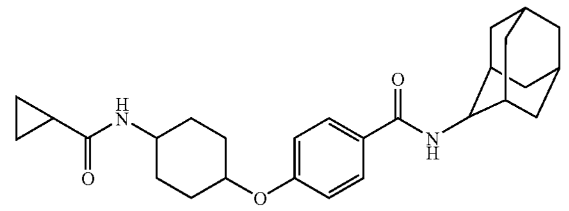

cis/trans-4-[4-(Cyclopropane-carbonyl-amino)-cyclohexyloxy]-N-adamantan-2-yl-benzamide,

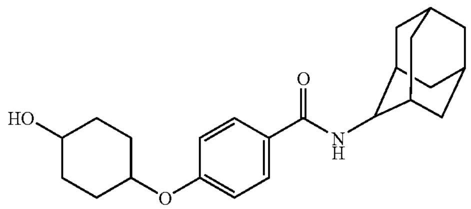

N-Adamantan-2-yl-4-(4-hydroxy-cyclohexyloxy)-benzamide,

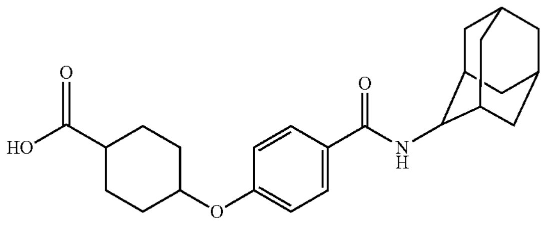

Cis/trans 4-[4-adamantan-2-ylcarbamoyl)-phenoxy]-cyclohexanecarboxylic acid,

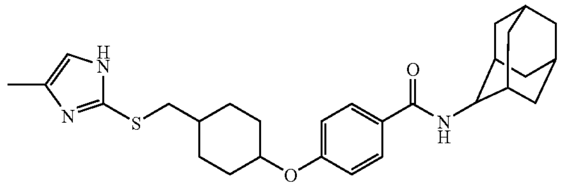

N-Adamantan-2-yl-4-[4-(4-methyl-1H-imidazol-2-ylsulfanylmethyl)-cyclohexyloxy]-benzamide,

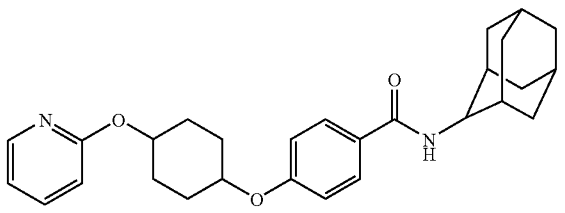

4-[4-(Pyridin-2-yloxy)-cyclohexyloxy]-N-adamantan-2-yl-benzamide,

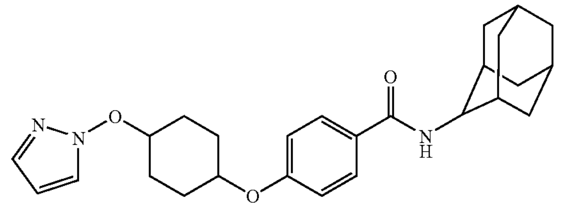

4-[4-(Pyrazol-1-yloxy)-cyclohexyloxy]-N-adamantan-2-yl-benzamide,

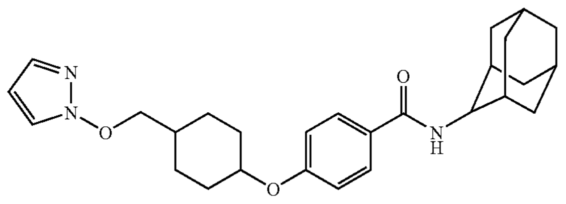

4-[4-(Pyrazol-1-yl-oxymethyl)-cyclohexyloxy]-N-adamantan-2-yl-benzamide,

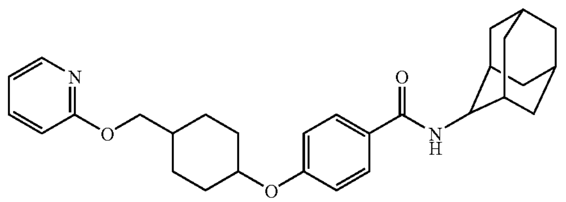

4-[4-(Pyridin-2-yloxymethyl)-cyclohexyloxy]-N-adamantan-2-yl-benzamide,

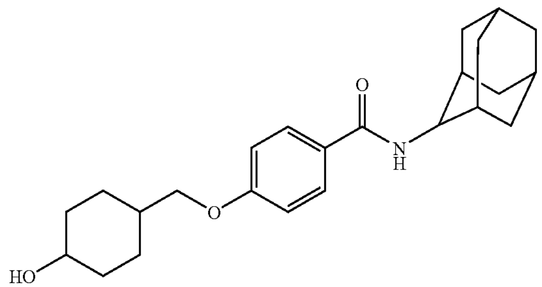

4-(4-Hydroxy-cyclohexyl-methoxy)-N-adamantan-2-yl-benzamide,

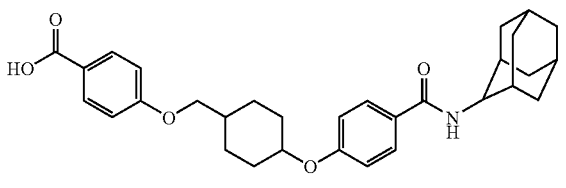

4-{4-[4-(Adamantan-2-yl-carbamoyl)-phenoxy]-cyclohexylmethoxy}-benzoic acid,

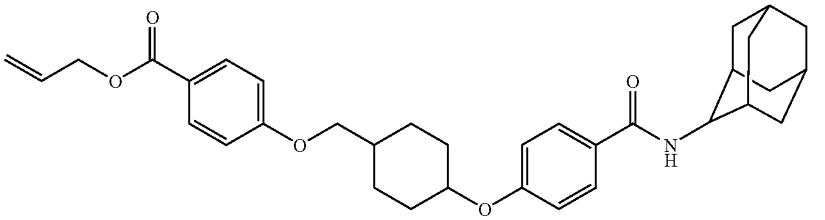

4-{4-[4-(Adamantan-2-yl-carbamoyl)-phenoxy]-cyclohexylmethoxy}-benzoic acid allyl ester,

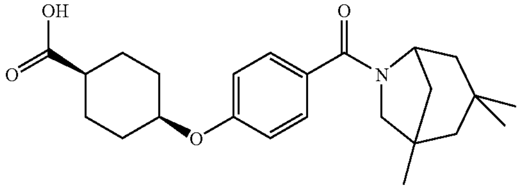

Cis-4-[4-(1,3,3-trimethyl-6-aza-bicyclo[3.2.1]octane-6-carbonyl)-phenoxy]-cyclohexane carboxylic acid,

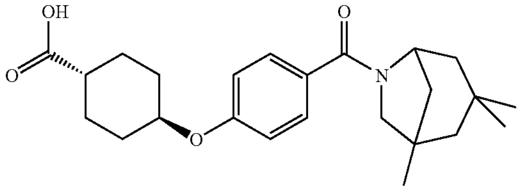

Trans-4-[4-(1,3,3-trimethyl-6-aza-bicyclo[3.2.1]octane-6-carbonyl)-phenoxy]-cyclohexane carboxylic acid,

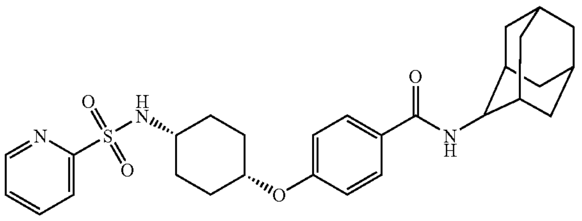

Cis-N-Adamantan-2-yl-4-[4-(pyridine-2-sulfonylamino)-cyclohexyloxy]-benzamide,

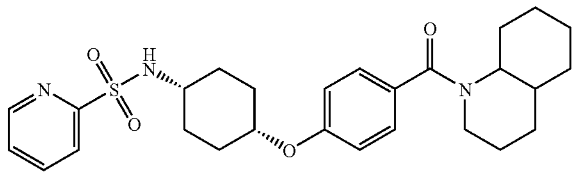

Cis-Pyridine-2-sulfonic acid {4-[4-(octahydro-quinoline-1-carbonyl)-phenoxy]-cyclohexyl}-amide,

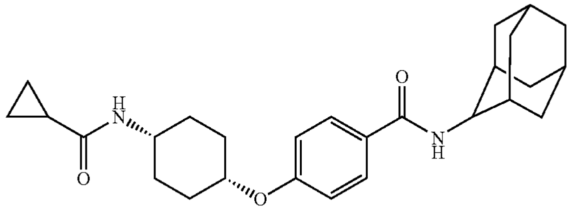

Cis-N-Adamantan-2-yl-4-[4-(cyclopropanecarbonyl-amino)-cyclohexyloxy]-benzamide,

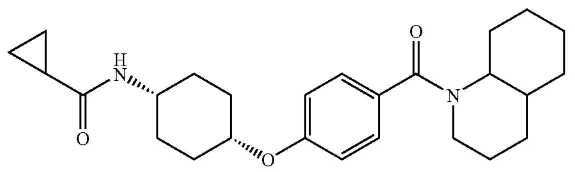

Cis-Cyclopropanecarboxylic acid {4-[4-(octahydro-quinoline-1-carbonyl)-phenoxy]-cyclohexyl}amide,

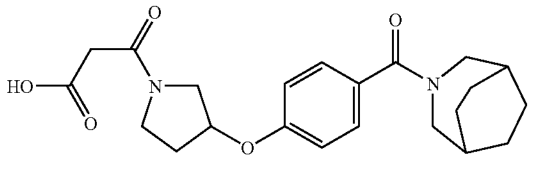

3-{3-[4-(3-Aza-bicyclo[3.2.2]nonane-3-carbonyl)-phenoxy]-pyrrolidin-1-yl}-3-oxo-propionic acid,

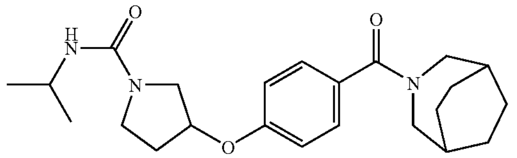

3-[4-(3-Aza-bicyclo[3.2.2]nonane-3-carbonyl)-phenoxy]-pyrrolidine-1-carboxylic acid isopropylamide,

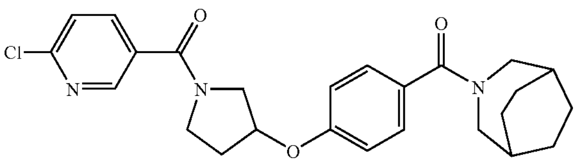

{3-[4-(3-Aza-bicyclo[3.2.2]nonane-3-carbonyl)-phenoxy]-pyrrolidin-1-yl}-(6-chloro-pyridin-3-yl)-methanone,

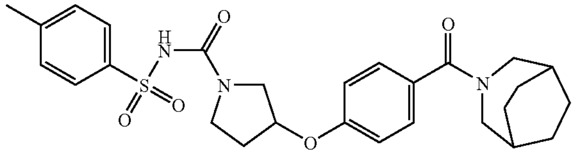

N-{3-[4-(3-Aza-bicyclo[3.2.2]nonane-3-carbonyl)-phenoxy]pyrrolidine-1-carbonyl}-4-methyl-benzenesulfonamide,

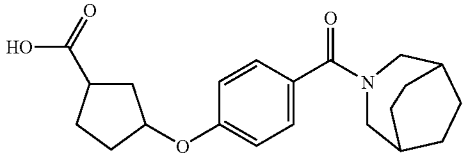

3-[4-(3-Aza-bicyclo[3.2.2]nonane-3-carbonyl)-phenoxy]-cyclopentanecarboxylic acid,

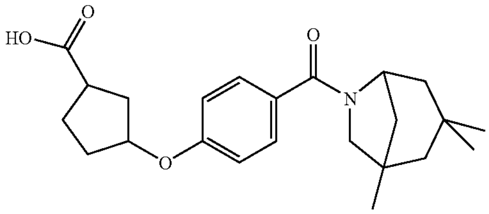

3-[4-(1,3,3-Trimethyl-6-aza-bicyclo[3.2.1]octane-6-carbonyl)-phenoxy]-cyclopentane carboxylic acid,

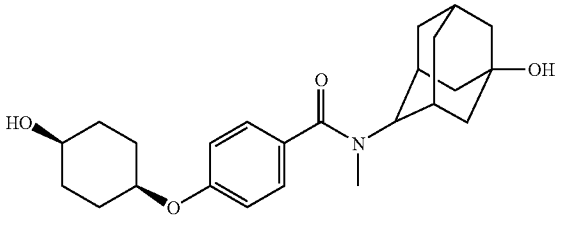

N-(5-Hydroxy-adamantan-2-yl)-4-(4-hydroxy-cyclohexyloxy)-N-methyl-benzamide,

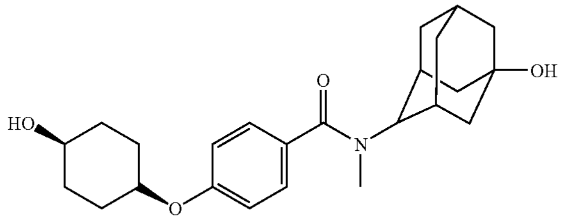

N-(5-Hydroxy-adamantan-2-yl)-4-(4-hydroxy-cyclohexyloxy)-N-methyl-benzamide,

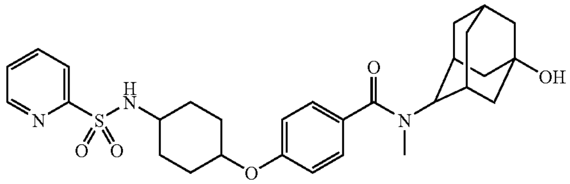

N-(5-Hydroxy-adamantan-2-yl)-N-methyl-4-[4-(pyridine-2-sulfonylamino)-cyclohexyloxy]-benzamide,

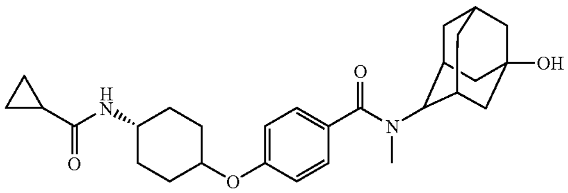

4-[4-(Cyclopropanecarbonyl-amino)-cyclohexyloxy]-N-(5-hydroxy-adamantan-2-yl)-N-methyl-benzamide,

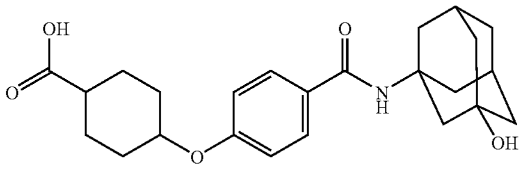

4-[4-(3-Hydroxy-adamantan-1-ylcarbamoyl)-phenoxy]-cyclohexanecarboxylic acid,

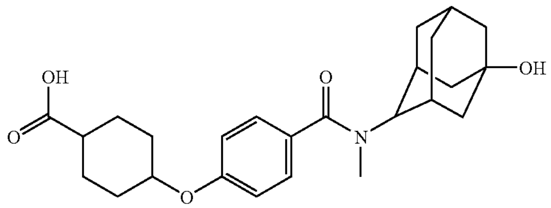

4-{4-[(5-Hydroxy-adamantan-2-yl)-methyl-carbamoyl]-phen-oxy}-cyclohexanecarboxylic acid,

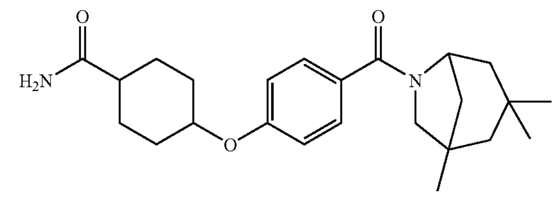

4-[4-(1,3,3-Trimethyl-6-aza-bicyclo[3.2.1]octane-6-carbonyl)-phenoxy]-cyclohexane carboxylic acid amide,

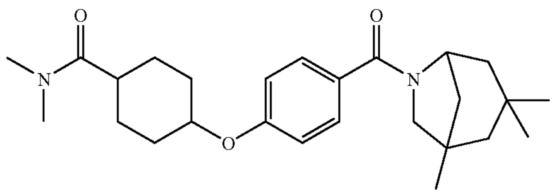

4-[4-(1,3,3-Trimethyl-6-aza-bicyclo[3.2.1]octane-6-carbonyl)-phenoxy]-cyclo-hexane carboxylic acid dimethylamide,

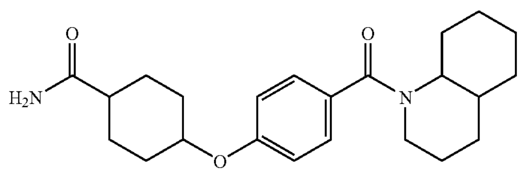

4-[4-(Octahydro-quinoline-1-carbonyl)-phenoxy]-cyclohexanecarboxylic acid amide,

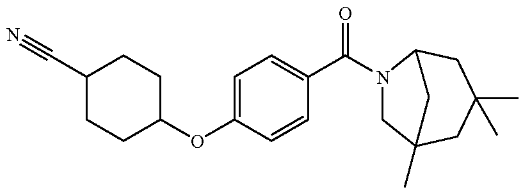

4-[4-(1,3,3-Trimethyl-6-aza-bicyclo[3.2.1]octane-6-carbonyl)-phenoxy]-cyclohexane carbonitrile,

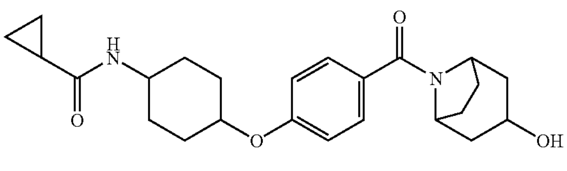

Cyclopropanecarboxylic acid {4-[4-(3-hydroxy-8-aza-bicyclo[3.2.1]octane-8-carbonyl)-phenoxy]-cyclohexyl}-amide,

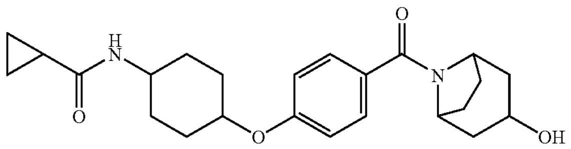

Cyclopropanecarboxylic acid {4-[4-(3-hydroxy-8-aza-bicyclo[3.2.1]octane-8-carbonyl)-phenoxy]-cyclohexyl}-amide,

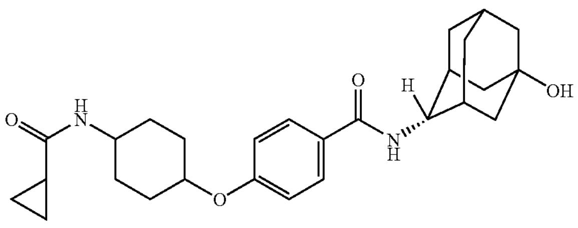

4-[4-(Cyclopropanecarbonyl-amino)-cyclohexyloxy]-N-(Z)-(5-hydroxy-adamantan-2-yl)-benzamide,

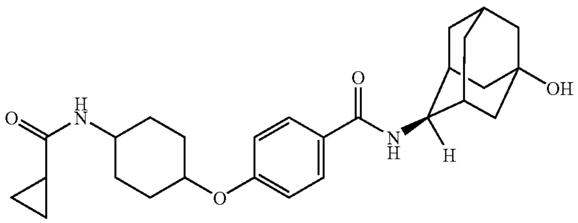

4-[4-(Cyclopropanecarbonyl-amino)-cyclohexyloxy]-N-(E)-(5-hydroxy-adamantan-2-yl)-benzamide,

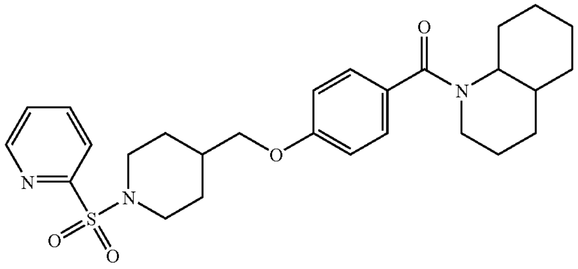

(Octahydro-quinolin-1-yl)-{-4-[1-(pyridine-2-sulfonyl)-piperidin-4-ylmethoxy]-phenyl}-methanone,

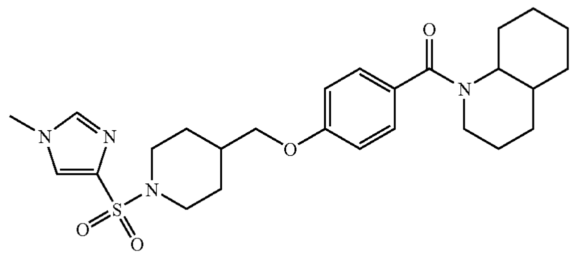

{4-[1-(1-Methyl-1H-imidazole-4-sulfonyl)-piperidin-4-yl-methoxy]-phenyl}-(octahydro-quinolin-1-yl)-methanone,

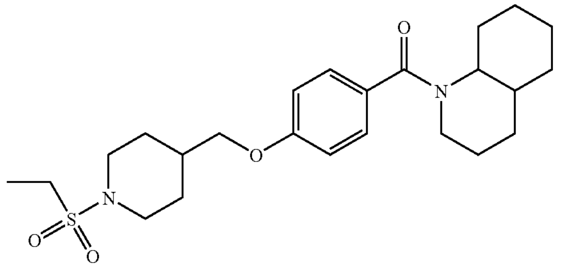

[4-(1-Ethanesulfonyl-piperidin-4-yl-methoxy)-phenyl]-(octahydro-quinolin-1-yl)-methanone,

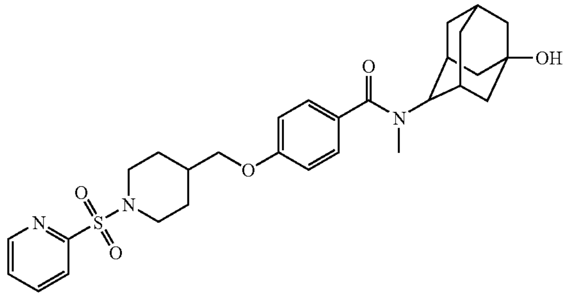

N-(5-Hydroxy-adamantan-2-yl)-N-methyl-4-[1-(pyridine-2-sulfonyl)-piperidin-4-yl-methoxy]-benzamide,

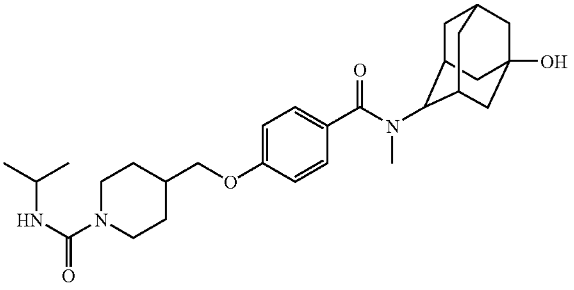

4-{4-[(5-Hydroxy-adamantan-2-yl)-methyl-carbamoyl]-phenoxy-methyl}-piperidine-1-carboxylic acid isopropylamide,

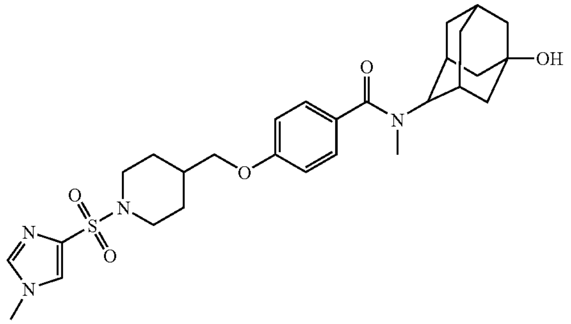

N-(5-Hydroxy-adamantan-2-yl)-N-methyl-4-[1-(1-methyl-1H-imidazole-4-sulfonyl)-piperidin-4-ylmethoxy]-benzamide,

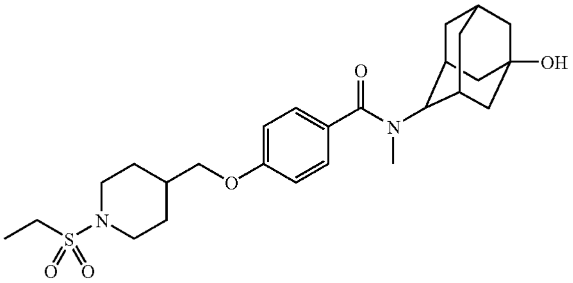

4-(1-Ethanesulfonyl-piperidin-4-ylmethoxy)-N-(5-hydroxy-adamantan-2-yl)-N-methyl-benzamide,

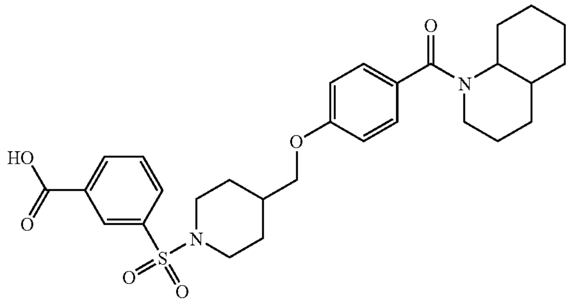

3-{4-[4-(Octahydro-quinoline-1-carbonyl)-phenoxymethyl]-piperidine-1-sulfonyl}-benzoic acid,

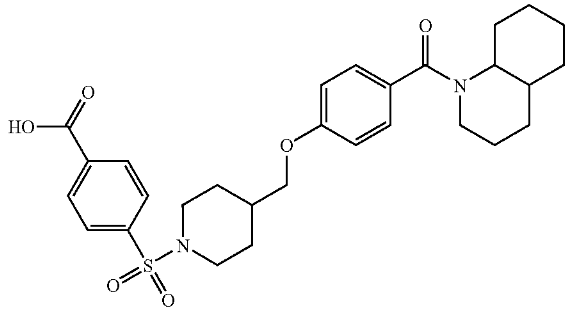

4-{4-[4-(Octahydro-quinoline-1-carbonyl)-phenoxymethyl]-piperidine-1-sulfonyl}-benzoic acid,

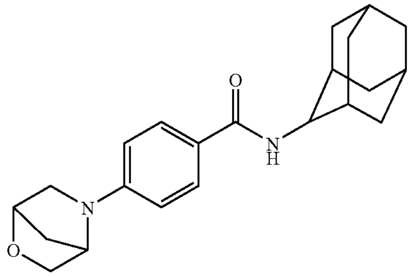

4-(2-Oxa-5-aza-bicyclo[2.2.1]hept-5-yl)-N-adamantan-2-yl-benzamide,

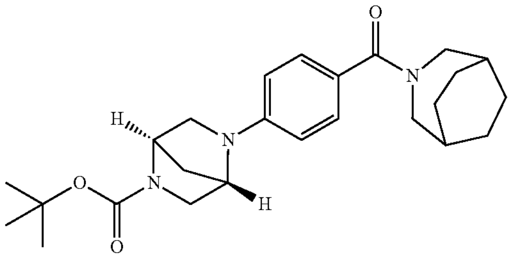

(1S,4S)-5-[4-(3-Aza-bicyclo[3.2.2]nonane-3-carbonyl)-phenyl]-2,5-diaza-bicyclo[2.2.1]-heptane-2-carboxylic acid tert-butyl ester,

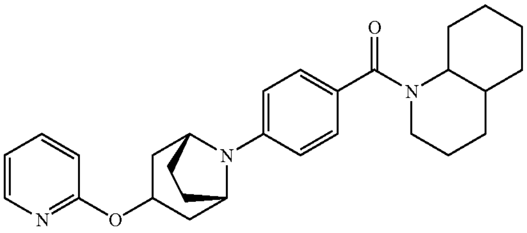

(Octahydro-quinolin-1-yl)-{4-[(1S,5R)-3-(pyridin-2-yloxy)-8-aza-bicyclo[3.2.1]oct-8-yl]-phenyl}-methanone,

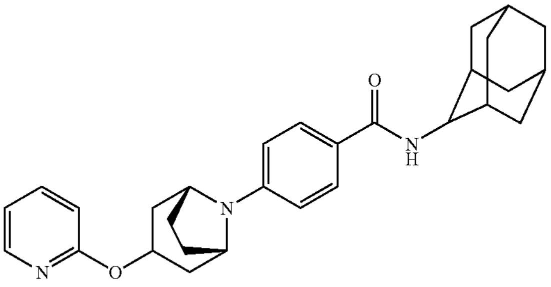

4-[(1S,5R)-3-(Pyridin-2-yloxy)-8-aza-bicyclo[3.2.1]oct-8-yl]-N-adamantan-2-yl-benzamide; or a salt thereof with a pharmaceutically acceptable acid or base, or any optical isomer or mixture of optical isomers, including a racemic mixture, or any tautomeric forms.

In another embodiment of the present invention, in formula (I) the polar surface area (PSA) of said compound is in the range from 40 Å$^2$ to 130 Å$^2$, preferably from 50 Å$^2$ to 130 Å$^2$, more preferably from 60 Å$^2$ to 120 Å$^2$, more preferably from 70 Å$^2$ to 120 Å$^2$, most preferable from 70 Å$^2$ to 110 Å$^2$.

In another embodiment of the present invention, in formula (I) the molar weight of said compound is in the range from 350 D to 650 D, preferably from 400 D to 600 D.

The compounds of the present invention have asymmetric centers and may occur as racemates, racemic mixtures, and as individual enantiomers or diastereoisomers, with all isomeric forms being included in the present invention as well as mixtures thereof.

The present invention also encompasses pharmaceutically acceptable salts of the present compounds. Such salts include pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Further examples of pharmaceutically acceptable inorganic or organic acid addition salts include the pharmaceutically accept-able salts listed in J. Pharm. Sci., 66, 2 (1977), which is incorporated herein by reference. Examples of metal salts include lithium, sodium, potassium, barium, calcium, magnesium, zinc, calcium salts and the like. Examples of amines and organic amines include ammonium, methylamine, dimethylamine, trimethylamine, ethylamine, diethylamine, propylamine, butylamine, tetramethylamine, ethanolamine, diethanolamine, triethanolamine, meglumine, ethylenediamine, choline, N,N'-dibenzylethylenediamine, N-benzylphenylethylamine, N-methyl-D-glucamine, guanidine and the like. Examples of cationic amino acids include lysine, arginine, histidine and the like.

Further, some of the compounds of the present invention may form solvates with water or common organic solvents. Such solvates are encompassed within the scope of the invention.

The pharmaceutically acceptable salts are prepared by reacting a compound of the present invention with 1 to 4 equivalents of a base such as sodium hydroxide, sodium meth-oxide, sodium hydride, potassium tert-butoxide, calcium hydroxide, magnesium hydroxide and the like, in solvents like ether, THF, methanol, tert-butanol, dioxane, isopropanol, ethanol etc. Mixtures of solvents may be used. Organic bases like lysine, arginine, diethanolamine, choline, guandine and their derivatives etc. may also be used. Alternatively, acid addition salts wherever applicable are prepared by treatment with acids such as hydrochloric acid, hydrobromic acid, nitric acid, sulfuric acid, phosphoric acid, p-toluenesulphonic acid, methanesulfonic acid, acetic acid, citric acid, maleic acid salicylic acid, hydroxynaphthoic acid, ascorbic acid, palmitic acid, succinic acid, benzoic acid, benzenesulfonic acid, tartaric acid and the like in solvents like ethyl acetate, ether, alcohols, acetone, THF, dioxane etc. Mixture of solvents may also be used.

The stereoisomers of the compounds forming part of this invention may be prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, enzymatic resolution, resolving the diastereomeric salts formed with chiral acids such as mandelic acid, camphorsulfonic acid, tartaric acid, lactic acid, and the like wherever applicable or chiral bases such as brucine, (R)- or (S)-phenylethylamine, cinchona alkaloids and their derivatives and the like. Commonly used methods are compiled by Jaques et al. in "Enantiomers, Racemates and Resolution" (Wiley Interscience, 1981). More specifically the compound of the present invention may be converted to a 1:1 mixture of diastereomeric amides by treating with chiral amines, aminoacids, aminoalcohols derived from aminoacids; conventional reaction conditions may be employed to convert acid into an amide; the diastereomers may be separated either by fractional crystallization or chromatography and the stereoisomers of compound of formula I may be prepared by hydrolysing the pure diastereomeric amide.

Various polymorphs of the compounds forming part of this invention may be pre-pared by crystallization of said compounds under different conditions; for example, using different solvents commonly used or their mixtures for recrystallization; crystallizations at differ-ent temperatures; or various modes of cooling, ranging from very fast to very slow cooling during crystallizations. Polymorphs may also be obtained by heating or melting the compound followed by gradual or fast cooling. The presence of polymorphs may be determined by solid probe nmr spectroscopy, it spectroscopy, differential scanning calorimetry, powder X-ray diffraction or such other techniques.

The invention also encompasses prodrugs of the present compounds, which on ad-ministration undergo chemical conversion by metabolic processes before becoming active pharmacological substances. In general, such prodrugs will be functional derivatives of the present compounds, which are readily convertible in vivo into the required compound of the present invention. Conventional procedures for the selection and preparation of suitable prodrug derivatives are described, for example, in "Design of Prodrugs", ed. H. Bundgaard, Elsevier, 1985.

It is a well known problem in drug discovery that compounds, such as enzyme inhibitors, may be very potent and selective in biochemical assays, yet be inactive in vivo. This lack of so-called bioavailability may be ascribed to a number of different factors such as lack of or poor absorption in the gut, first pass metabolism in the liver and/or poor uptake in cells. Although the factors determining bioavailability are not completely understood, there are many examples in the scientific literature—well known to those skilled in the art—of how to modify compounds, which are potent and selective in biochemical assays but show low or no activity in vivo, into drugs that are biologically active.

It is within the scope of the invention to modify the compounds of the present invention, termed the 'original compound', by attaching chemical groups that will improve the bioavailability of said compounds in such a way that the uptake in cells or mammals is facilitated.

Examples of said modifications, which are not intended in any way to limit the scope of the invention, include changing of one or more carboxy groups to esters (for instance methyl esters, ethyl esters, tert-butyl, acetoxymethyl, pivaloyloxymethyl esters or other acyloxymethyl esters). Compounds of the invention, original compounds, such modified by attaching chemical groups are termed 'modified compounds'.

The invention also encompasses active metabolites of the present compounds.

The compounds according to the invention alter, and more specifically, reduce the level of active intracellular glucocorticoid and are accordingly useful for the treatment, prevention and/or prophylaxis of disorders and diseases in which such a modulation or reduction is beneficial.

Accordingly, the present compounds may be applicable for the treatment, prevention and/or prophylaxis of the metabolic syndrome, insulin resistance, dyslipidemia, hypertension, obesity, type 2 diabetes, impaired glucose tolerance (IGT), impaired fasting glucose (IFG), Latent Autoimmune Diabetes in the Adult (LADA), type 1 diabetes, diabetic late complications including cardiovascular diseases, cardiovascular disorders, disorders of lipid metabolism, neurodegenerative and psychiatric disorders, dysregulation of intraocular pressure including glaucoma, immune disorders, inappropriate immune responses, musculo-skeletal disorders, gastrointestinal disorders, polycystic ovarie syndrome (PCOS), reduced hair growth or other diseases, disorders or conditions that are influenced by intracellular glucocorticoid levels, adverse effects of increased blood levels of active endogenous or exogenous glucocorticoid, and any combination thereof, adverse effects of increased plasma levels of endogenous active glucocorticoid, Cushing's disease, Cushing's syndrome, adverse effects of glucocorticoid receptor agonist treatment of autoimmune diseases, adverse effects of glucocorticoid receptor agonist treatment of inflammatory diseases, adverse effects of glucocorticoid receptor agonist treatment of diseases with an inflammatory component, adverse effects of glucocorticoid receptor agonist treatment as a part of cancer chemotherapy, adverse effects of glucocorticoid receptor agonist treatment for surgical/post-surgical or other trauma, adverse effects of glucocorticoid receptor agonist therapy in the context of organ or tissue transplantation or adverse effects of glucocorticoid receptor agonist treatment in other diseases, disorders or conditions where glucocorticoid receptor agonists provide clinically beneficial effects. Also the present compounds may be applicable for the treatment of visceral fat accumulation and insulin resistance in HAART (highly active antiretroviral treatment)-treated patients.

More specifically the present compounds may be applicable for the treatment, prevention and/or prophylaxis of the metabolic syndrome, type 2 diabetes, diabetes as a consequence of obesity, insulin resistance, hyperglycemia, prandial hyperglycemia, hyperinsulinemia, inappropriately low insulin secretion, impaired glucose tolerance (IGT), impaired fasting glucose (IFG), increased hepatic glucose production, type 1 diabetes, LADA, pediatric diabetes, dyslipidemia, diabetic dyslipidemia, hyperlipidemia, hypertriglyceridemia, hyperlipoproteinemia, hypercholesterolemia, decreased HDL cholesterol, impaired LDL/HDL ratio, other disorders of lipid metabolism, obesity, visceral obesity, obesity as a consequence of diabetes, increased food intake, hypertension, diabetic late complications, micro-/macroalbuminuria, nephropathy, retinopathy, neuropathy, diabetic ulcers, cardiovascular diseases, arteriosclerosis, atherosclerosis, coronary artery disease, cardiac hypertrophy, myocardial ischemia, heart insufficiency, congestional heart failure, stroke, myocardial infarction, arrythmia, decreased blood flow, erectile dysfunction (male or female), myopathy, loss of muscle tissue, muscle wasting, muscle catabolism, osteoporosis, decreased linear growth, neurodegenerative and psychiatric disorders, Alzheimers disease, neuronal death, impaired cognitive function, depression, anxiety, eating disorders, appetite regulation, migraine, epilepsia, addiction to chemical substances, disorders of intraocular pressure, glaucoma, polycystic ovary syndrome (PCOS), inappropriate immune responses, inappropriate T helper-1/T helper-2 polarisation, bacterial infections, mycobacterial infections, fungal infections, viral infections, parasitic infestations, suboptimal responses to immunizations, immune dysfunction, partial or complete baldness, or diseases, disorders or conditions that are influenced by intracellular glucocorticoid levels and any combination thereof, adverse effects of glucocorticoid receptor agonist treatment of allergic-inflammatory diseases such as asthma and atopic dermatitis, adverse effects of glucocorticoid receptor agonist treatment of disorders of the respiratory system e.g. asthma, cystic fibrosis, emphysema, bronchitis, hypersensitivity, pneumonitis, eosinophilic pneumonias, pulmonary fibrosis, adverse effects of glucocorticoid receptor agonist treatment of inflammatory bowel disease such as Crohn's disease and ulcerative colitis; adverse effects of glucocorticoid receptor agonist treatment of disorders of the immune sys-tem, connective tissue and joints e.g. reactive arthritis, rheumatoid arthritis, Sjögren's syndrome, systemic lupus erythematosus, lupus nephritis, Henoch-Schönlein purpura, Wegener's granulomatosis, temporal arteritis, systemic sclerosis, vasculitis, sarcoidosis, dermatomyositis-polymyositis, pemphigus vulgaris; adverse effects of glucocorticoid receptor agonist treatment of endocrinological diseases such as hyperthyroidism, hypoaldosteronism, hypopituitarism; adverse effects of glucocorticoid receptor agonist treatment of hematological diseases e.g. hemolytic anemia, thrombocytopenia, paroxysmal nocturnal hemoglobinuria; adverse effects of glucocorticoid receptor agonist treatment of cancer such as spinal cord diseases, neoplastic compression of the spinal cord, brain tumours, acute lymphoblastic leukemia, Hodgkin's disease, chemotherapy-induced nausea, adverse effects of glucocorticoid receptor agonist treatment of diseases of muscle and at the neuro-muscular joint e.g. myasthenia gravis and heriditary myopathies (e.g. Duchenne muscular dystrophy), adverse effects of glucocorticoid receptor agonist treatment in the context of surgery & transplantation e.g. trauma, post-surgical stress, surgical stress, renal transplantation, liver transplantation, lung transplantation, pancreatic islet transplantation, blood stem cell transplantation, bone marrow transplantation, heart transplantation, adrenal gland transplantation, tracheal transplantation, intestinal transplantation, corneal transplantation, skin grafting, keratoplasty, lens implantation and other procedures where immunosuppression with glucocorticoid receptor agonists is beneficial; adverse effects of glucocorticoid receptor agonist treatment of brain abscess, nausea/vomiting, infections, hypercalcemia, adrenal hyperplasia, autoimmune hepatitis, spinal cord diseases, saccular aneurysms or adverse effects to glucocorticoid receptor agonist treatment in other diseases, disorders and conditions where glucocorticoid receptor agonists provide clinically beneficial effects.

Accordingly, in a further aspect the invention relates to a compound according to the invention for use as a pharmaceutical composition.

The invention also relates to pharmaceutical compositions comprising, as an active ingredient, at least one compound according to the invention together with one or more pharmaceutically acceptable carriers or diluents.

The pharmaceutical composition is preferably in unit dosage form, comprising from about 0.05 mg/day to about 2000 mg/day, preferably from about 1 mg/day to about 500 mg/day of a compound according to the invention.

In another embodiment, the patient is treated with a compound according to the invention for at least about 1 week, for at least about 2 weeks, for at least about 4 weeks, for at least about 2 months or for at least about 4 months.

In yet another embodiment, the pharmaceutical composition is for oral, nasal, transdermal, pulmonal or parenteral administration.

Furthermore, the invention relates to the use of a compound according to the invention for the preparation of a pharmaceutical composition for the treatment, prevention and/or prophylaxis of disorders and diseases wherein a modulation or an inhibition of the activity of 11βHSD1 is beneficial.

The invention also relates to a method for the treatment, prevention and/or prophylaxis of disorders and diseases wherein a modulation or an inhibition of the activity of 11βHSD1 is beneficial, the method comprising administering to a subject in need thereof an effective amount of a compound according to the invention.

In a preferred embodiment of the invention the present compounds are used for the preparation of a medicament for the treatment, prevention and/or prophylaxis of any diseases and conditions that are influenced by intracellular glucocorticoid levels as mentioned above.

Thus, in a preferred embodiment of the invention the present compounds are used for the preparation of a medicament for the treatment, prevention and/or prophylaxis of conditions and disorders where a decreased level of active intracellular glucocorticoid is desirable, such as the conditions and diseases mentioned above.

In yet a preferred embodiment of the invention the present compounds are used for the preparation of a medicament for the treatment, prevention and/or prophylaxis of the metabolic syndrome including insulin resistance, dyslipidemia, hypertension and obesity.

In yet another preferred embodiment of the invention the present compounds are used for the preparation of a medicament for the treatment, prevention and/or prophylaxis of type 2 diabetes, impaired glucose tolerance (IGT), impaired fasting glucose (IFG).

In yet another preferred embodiment of the invention the present compounds are used for the preparation of a pharmaceutical composition for the delaying or prevention of the progression from IGT to type 2 diabetes.

In yet another preferred embodiment of the invention the present compounds are used for the preparation of a pharmaceutical composition for the delaying or prevention of the progression of the metabolic syndrome into type 2 diabetes.

In still another preferred embodiment of the invention the present compounds are used for the preparation of a pharmaceutical composition for the treatment, prevention and/or prophylaxis of diabetic late complications including cardiovascular diseases; arteriosclerosis; atherosclerosis.

In a further preferred embodiment of the invention the present compounds are used for the preparation of a pharmaceutical composition for the treatment, prevention and/or prophylaxis of neurodegenerative and psychiatric disorders.

In yet a further preferred embodiment of the invention the present compounds are used for the preparation of a pharmaceutical composition for the treatment, prevention and/or prophylaxis of adverse effects of glucocorticoid receptor agonist treatment or therapy.

In another embodiment of the present invention, the route of administration may be any route which effectively transports a compound according to the invention to the appropriate or desired site of action, such as oral, nasal, buccal, transdermal, pulmonal, or parenteral.

In still a further aspect of the invention the present compounds are administered in combination with one or more further active substances in any suitable ratios. Such further active substances may e.g. be selected from antiobesity agents, antidiabetics, agents modifying the lipid metabolism, antihypertensive agents, glucocorticoid receptor agonists, agents for the treatment and/or prevention of complications resulting from or associated with diabetes and agents for the treatment and/or prevention of complications and disorders resulting from or associated with obesity.

Thus, in a further aspect of the invention the present compounds may be administered in combination with one or more antiobesity agents or appetite regulating agents.

Such agents may be selected from the group consisting of CART (cocaine amphetamine regulated transcript) agonists, NPY (neuropeptide Y) antagonists, MC4 (melanocortin 4)

agonists, orexin antagonists, TNF (tumor necrosis factor) agonists, CRF (corticotropin re-leasing factor) agonists, CRF BP (corticotropin releasing factor binding protein) antagonists, urocortin agonists, β3 agonists, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, PPAR (peroxisome proliferator-activated receptor) modulators, RXR (retinoid X receptor) modulators, TR β agonists, AGRP (Agouti related protein) inhibitors, H3 histamine antagonists, opioid antagonists (such as naltrexone), exendin-4, GLP-1 and ciliary neurotrophic factor.

In one embodiment of the invention the antiobesity agent is leptin; dexamphetamine or amphetamine; fenfluramine or dexfenfluramine; sibutramine; orlistat; mazindol or phentermine.

Suitable antidiabetic agents include insulin, insulin analogues and derivatives such as those disclosed in EP 792 290 (Novo Nordisk A/S), e.g. $N\epsilon^{B29}$-tetradecanoyl des (B30) human insulin, EP 214 826 and EP 705 275 (Novo Nordisk A/S), e.g. $Asp^{B28}$ human insulin, U.S. Pat. No. 5,504,188 (Eli Lilly), e.g. $Lys^{B28}$ $Pro^{B29}$ human insulin, EP 368 187 (Aventis), e.g. Lantus, which are all incorporated herein by reference, GLP-1 (glucagon like peptide-1) and GLP-1 derivatives such as those disclosed in WO 98/08871 to Novo Nordisk A/S, which is incorporated herein by reference as well as orally active hypoglycaemic agents.

The orally active hypoglycaemic agents preferably comprise sulphonylureas, biguanides, meglitinides, glucosidase inhibitors, glucagon antagonists such as those disclosed in WO 99/01423 to Novo Nordisk A/S and Agouron Pharmaceuticals, Inc., GLP-1 agonists, potassium channel openers such as those disclosed in WO 97/26265 and WO 99/03861 to Novo Nordisk A/S which are incorporated herein by reference, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents and antilipidemic agents as PPARα modulators, PPARδ modulators, cholesterol absorption inhibitors, HSL (hormone-sensitive lipase) inhibitors and HMG CoA inhibitors (statins), nicotinic acid, fibrates, anion exchangers, compounds lowering food intake, bile acid resins, RXR agonists and agents acting on the ATP-dependent potassium channel of the β-cells.

In one embodiment, the present compounds are administered in combination with insulin or an insulin analogue or derivative, such as $N^{\epsilon B29}$-tetradecanoyl des (B30) human insulin, $Asp^{B28}$ human insulin, $Lys^{B28}$ $Pro^{B29}$ human insulin, Lantus®, or a mix-preparation comprising one or more of these.

In a further embodiment the present compounds are administered in combination with a sulphonylurea e.g. tolbutamide, glibenclamide, glipizide or glicazide.

In another embodiment the present compounds are administered in combination with a biguanide e.g. metformin.

In yet another embodiment the present compounds are administered in combination with a meglitinide e.g. repaglinide or senaglinide.

In still another embodiment the present compounds are administered in combination with a thiazolidinedione e.g. troglitazone, ciglitazone, pioglitazone, rosiglitazone or compounds disclosed in WO 97/41097 such as 5-[[4-[3-Methyl-4-oxo-3,4-dihydro-2-quinazolinyl]methoxy]phenyl-methyl]thiazolidine-2,4-dione or a pharmaceutically acceptable salt thereof, preferably the potassium salt.

In yet another embodiment the present compounds may be administered in combination with the insulin sensitizers disclosed in WO 99/19313 such as (−) 3-[4-[2-Phenoxazin-10-yl)ethoxy]phenyl]-2-ethoxypropanoic acid or a pharmaceutically acceptable salts thereof, preferably the arginine salt.

In a further embodiment the present compounds are administered in combination with an α-glucosidase inhibitor e.g. miglitol or acarbose.

In another embodiment the present compounds are administered in combination with an agent acting on the ATP-dependent potassium channel of the β-cells e.g. tolbutamide, glibenclamide, glipizide, glicazide or repaglinide.

Furthermore, the present compounds may be administered in combination with nateglinide.

In still another embodiment the present compounds are administered in combination with an antihyperlipidemic agent or antilipidemic agent e.g. cholestyramine, colestipol, clofibrate, gemfibrozil, fenofibrate, bezafibrate, tesaglitazar, EML-4156, LY-818, MK-767, atorvastatin, fluvastatin, lovastatin, pravastatin, simvastatin, acipimox, probucol, ezetimibe or dextrothyroxine.

In a further embodiment the present compounds are administered in combination with more than one of the above-mentioned compounds e.g. in combination with a sulphonylurea and metformin, a sulphonylurea and acarbose, repaglinide and metformin, insulin and a sulphonylurea, insulin and metformin, insulin, insulin and lovastatin, etc.

Further, the present compounds may be administered in combination with one or more antihypertensive agents. Examples of antihypertensive agents are β-blockers such as alprenolol, atenolol, timolol, pindolol, propranolol, metoprolol, bisoprololfumerate, esmolol, acebutelol, metoprolol, acebutolol, betaxolol, celiprolol, nebivolol, tertatolol, oxprenolol, amusolalul, carvedilol, labetalol, β2-receptor blockers e.g. S-atenolol, OPC-1085, ACE (angiotensin converting enzyme) inhibitors such as quinapril, lisinopril, enalapril, captopril, benazepril, perindopril, trandolapril, fosinopril, ramipril, cilazapril, delapril, imidapril, moexipril, spirapril, temocapril, zofenopril, S-5590, fasidotril, Hoechst-Marion Roussel: 100240 (EP 00481522), omapatrilat, gemopatrilat and GW-660511, calcium channel blockers such as nifedipine, felodipine, nicardipine, isradipine, nimodipine, diltiazem, amlodipine, nitrendipine, verapamil, lacidipine, lercanidipine, aranidipine, cilnidipine, clevidipine, azelnidipine, barnidipine, efonodipine, iasidipine, iemildipine, iercanidipine, manidipine, nilvadipine, pranidipine, furnidipine, α-blockers such as doxazosin, urapidil, prazosin, terazosin, bunazosin and OPC-28326, diuretics such as thiazides/sulphonamides (e.g. bendroflumetazide, chlorothalidone, hydrochlorothiazide and clopamide), loop-diuretics (e.g. bumetanide, furosemide and torasemide) and potassium sparing diuretics (e.g. amiloride, spironolactone), endothelin ET-A antagonists such as ABT-546, ambrisetan, atrasentan, SB-234551, CI-1034, S-0139 and YM-598, endothelin antagonists e.g. bosentan and J-104133, renin inhibitors such as aliskiren, vasopressin V1 antagonists e.g. OPC-21268, vasopressin V2 antagonists such as tolvaptan, SR-121463 and OPC-31260, B-type natriuretic peptide agonists e.g. Nesiritide, angiotensin II antagonists such as irbesartan, candesartancilexetil, losartan, valsartan, telmisartan, eprosartan, candesartan, CL-329167, eprosartan, iosartan, olmesartan, pratosartan, TA-606, and YM-358, 5-HT2 agonists e.g. fenoldopam and ketanserin, adenosine A1 antagonists such as naftopidil, N-0861 and FK-352, thromboxane A2 antagonists such as KT2-962, endopeptidase inhibitors e.g. ecadotril, nitric oxide agonists such as LP-805, dopamine D1 antagonists e.g. MYD-37, dopamine D2 agonists such as nolomirole, n-3 fatty acids e.g. omacor, prostacyclin agonists such as treprostinil, beraprost, PGE1 agonists e.g. ecraprost, Na+/K+ ATPase modulators e.g. PST-2238, Potassium channel activators e.g. KR-30450, vaccines such as PMD-3117, Indapamides, CGRP-unigene, guanylate cyclase stimulators, hydralazines, methyldopa, docarpamine, moxonidine, CoAprovel, Mondo-Biotech-811.

Further reference can be made to Remington: The Science and Practice of Pharmacy, 19$^{th}$ Edition, Gennaro, Ed., Mack Publishing Co., Easton, Pa., 1995.

Furthermore, the present compounds may be administered in combination with one or more glucocorticoid receptor agonists. Examples of such glucocorticoid receptor agonists are betametasone, dexamethasone, hydrocortisone, methylprednisolone, prednisolone, prednisone, beclomethasone, butixicort, clobetasol, flunisolide, flucatisone (and analogues), momethasone, triamcinolonacetonide, triamcinolonhexacetonide GW-685698, NXC-1015, NXC-1020, NXC-1021, NS-126, P-4112, P-4114, RU-24858 and T-25 series.

It should be understood that any suitable combination of the compounds according to the invention with one or more of the above-mentioned compounds and optionally one or more further pharmacologically active substances are considered to be within the scope of the present invention.

Pharmaceutical Compositions

The compounds of the present invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19$^{th}$ Edition, Gennaro, Ed., Mack Publishing Co., Easton, Pa., 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as hard or soft capsules, tablets, troches, dragees, pills, lozenges, powders and granules. Where appropriate, they can be prepared with coatings such as enteric coatings or they can be formulated so as to provide controlled release of the active ingredient such as sustained or prolonged release according to methods well-known in the art.

Liquid dosage forms for oral administration include solutions, emulsions, suspensions, syrups and elixirs.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use. De-pot injectable formulations are also contemplated as being within the scope of the present invention.

Other suitable administration forms include suppositories, sprays, ointments, crèmes, gels, inhalants, dermal patches, implants etc.

A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain from 0.05 to about 2000 mg, e.g. from about 0.1 to about 1000 mg, from about 0.5 mg to about 500 mg, from about 1 mg to about 200 mg, e.g. about 100 mg.

For parenteral routes, such as intravenous, intrathecal, intramuscular and similar ad-ministration, typically doses are in the order of about half the dose employed for oral administration.

The compounds of this invention are generally utilized as the free substance or as a pharmaceutically acceptable salt thereof. Examples are an acid addition salt of a compound having the utility of a free base and a base addition salt of a compound having the utility of a free acid. The term "pharmaceutically acceptable salts" refers to non-toxic salts of the compounds for use according to the present invention which are generally prepared by reacting the free base with a suitable organic or inorganic acid or by reacting the acid with a suitable organic or inorganic base. When a compound for use according to the present invention, contains a free base such salts are prepared in a conventional manner by treating a solution or suspension of the compound with a chemical equivalent of a pharmaceutically acceptable acid. When a compounds for use according to the present invention, contains a free acid such salts are prepared in a conventional manner by treating a solution or suspension of the compound with a chemical equivalent of a pharmaceutically acceptable base. Physiologically acceptable salts of a compound with a hydroxy group include the anion of said compound in combination with a suitable cation such as sodium or ammonium ion. Other salts which are not pharmaceutically acceptable may be useful in the preparation of compounds for use according to the present invention and these form a further aspect of the present invention.

For parenteral administration, solutions of the present compounds in sterile aqueous solution, aqueous propylene glycol or sesame or peanut oil may be employed. Such aqueous solutions should be suitable buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of suitable carriers are water, salt solutions, alcohols, polyethylene glycols, polyhydroxyethoxylated castor oil, peanut oil, olive oil, syrup, phospholipids, gelatine, lactose, terra alba, sucrose, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent may include any sustained release material known in the art, such as glyceryl monostearate or glyceryl distearate, alone or mixed with a wax. The formulations may also include wetting agents, emulsifying and suspending agents, preserving agents, sweetening agents or flavouring agents.

The pharmaceutical compositions formed by combining the compounds of the invention and the pharmaceutically acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and which may include a suitable excipient. These formulations may be in the form of powder or granules, as a solution or suspension in an aqueous or non-aqueous liquid, or as an oil-in-water or water-in-oil liquid emulsion.

Compositions intended for oral use may be prepared according to any known method, and such compositions may contain one or more agents selected from the group consisting of sweetening agents, flavouring agents, colouring agents, and preserving agents in order to pro-vide pharmaceutically elegant and palatable preparations. Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatine or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,356,108; 4,166,452; and 4,265,874, incorporated herein by reference, to form osmotic therapeutic tablets for controlled release.

Formulations for oral use may also be presented as hard gelatine capsules where the active ingredient is mixed with an inert solid diluent, for example, calcium carbonate, calcium phosphate or kaolin, or a soft gelatine capsule wherein the active ingredient is mixed with water or an oil medium, for example peanut oil, liquid paraffin, or olive oil.

Aqueous suspensions may contain the active compounds in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyl-eneoxycetanol, or condensation products of ethylene oxide with partial esters derived from fatty acids and a hexitol such as polyoxyethylene sorbitol monooleate, or condensation products of ethyl-ene oxide with partial esters derived from fatty acids and hexitol anhydrides, for example poly-ethylene sorbitan monooleate. The aqueous suspensions may also contain one or more colouring agents, one or more flavouring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavouring, and colouring agents may also be present.

The pharmaceutical compositions comprising a compound for use according to the present invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, preservative and flavouring and colouring agent. The pharmaceutical compositions may be in the form of a sterile injectable aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

The compositions may also be in the form of suppositories for rectal administration of the compounds of the present invention. These compositions can be prepared by mixing the drug with a suitable non-irritating excipient which is solid at ordinary temperatures but liquid at the rectal temperature and will thus melt in the rectum to release the drug. Such materials include cocoa butter and polyethylene glycols, for example.

For topical use, creams, ointments, jellies, solutions of suspensions, etc., containing the compounds of the present invention are contemplated. For the purpose of this application, topical applications shall include mouth washes and gargles.

The compounds for use according to the present invention may also be administered in the form of liposome delivery systems, such as small unilamellar vesicles, large unilamellar vesicles, and multilamellar vesicles. Liposomes may be formed from a variety of phospholipids, such as cholesterol, stearylamine, or phosphatidylcholines.

In addition, some of the compounds for use according to the present invention may form solvates with water or common organic solvents. Such solvates are also encompassed within the scope of the present invention.

Thus, in a further embodiment, there is provided a pharmaceutical composition comprising a compound for use according to the present invention, or a pharmaceutically acceptable salt, solvate, or prodrug thereof, and one or more pharmaceutically acceptable carriers, excipients, or diluents.

If a solid carrier is used for oral administration, the preparation may be tabletted, placed in a hard gelatine capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatine capsule or sterile injectable liquid such as an aqueous or non-aqueous liquid suspension or solution.

A typical tablet which may be prepared by conventional tabletting techniques may contain:

Core:

| | |
|---|---|
| Active compound (as free compound or salt thereof) | 5.0 mg |
| Lactosum Ph. Eur. | 67.8 mg |
| Cellulose, microcryst. (Avicel) | 31.4 mg |
| Amberlite ® IRP88* | 1.0 mg |
| Magnesii stearas Ph. Eur. | q.s. |

Coating:

| | |
|---|---|
| Hydroxypropyl methylcellulose | approx. 9 mg |
| Mywacett 9-40 T** | approx. 0.9 mg |

*Polacrillin potassium NF, tablet disintegrant, Rohm and Haas.

**Acylated monoglyceride used as plasticizer for film coating.

The compounds of the invention may be administered to a patient which is a mammal, especially a human in need thereof. Such mammals include also animals, both domestic animals, e.g. household pets, and non-domestic animals such as wildlife.

Any novel feature or combination of features described herein is considered essential to this invention.

The present invention also relate to the below methods of preparing the compounds of the invention.

The present invention is further illustrated in the following representative examples which are, however, not intended to limit the scope of the invention in any way.

EXAMPLES

The following general procedures refer to intermediate compounds and final products for general formula (I) identified in the specification and in the synthesis schemes. The preparation of the compounds of general formula (I) of the present invention is described in detail using the following. Occasionally, the reaction may not be applicable as described to each compound included within the disclosed scope of the invention. The compounds for which this occurs will be readily recognised by those skilled in the art. In these cases the re-actions can be successfully performed by conventional modifications known to those skilled in the art, which is, by appropriate protection of interfering groups, by changing to other conventional reagents, or by routine modification of reaction conditions. Alternatively, other reactions disclosed herein or otherwise conventional will be applicable to the preparation of the corresponding compounds of the invention. In all preparative methods, all starting materials are known or may easily be prepared from known starting materials. The structures of the compounds are confirmed by either elemental analysis or nuclear magnetic resonance (NMR), where peaks assigned to characteristic protons in the title compounds are presented where appropriate. 1H NMR shifts (δH) are given in parts per million (ppm) down field from tetramethylsilane as internal reference standard. M.p.: is melting point and is given in ° C. and is not corrected. Column chromatography was carried out using the technique described by W. C. Still et al., J. Org. Chem. 43: 2923 (1978) on Merck silica gel 60 (Art. 9385).

HPLC Systems:

HPLC-MS: The RP-analysis was performed on an Agilent HPLC system (1100 degasser, 1100 pump, 1100 injector and a 1100 DAD) fitted with an Agilent MS detector system Model VL (MW 0-1000) and a S.E.D.E.R.E Model Sedex 55 ELS detector system using a Waters X-terra MS C18 column (5 μm, 3.0 mm×50 mm) with gradient elution, 5% to 95% solvent B (0.05% TFA in acetonitrile) in solvent A (0.05% TFA in water) within 3 min, 2.7 mL/min.

The abbreviations as used in the present application have the following meaning:

TLC: Thin layer chromatography

CDCl3: Deuterio chloroform

DCM: Dichloromethane

DIIC: N,N'-Diisopropylcarbodiimide

DMAP: 4-Dimethylaminopyridine

DMSO-d6: Hexadeuterio dimethylsulfoxide

DMSO: Dimethylsulfoxide

DIPEA: Diisopropylethylamine

EDAC: 1-(3-Dimethylaminopropyl)-3-ethylcarbodiimide hydrochloride

EtOAc: Ethyl acetate

THF: Tetrahydrofuran

DMF: N,N-dimethylformamide

HOBT: 1-Hydroxy-benzotriazole

POL: Polystyrene

MeCN: Acetonitrile

NMP: N-Methylpyrrolidinone

TEA: Triethylamine

TFA: Trifluoroacetic acid

EDAC: 1-(3-Dimethylaminopropyl)-3-ethylcarbodiimide, hydrochloride min: minutes hrs: hours The following compounds are either prepared according to the synthesis scheme 1, scheme 2 or scheme 3 by the use of standard reactions readily recognized by those skilled in the art.

Synthesis scheme 1:

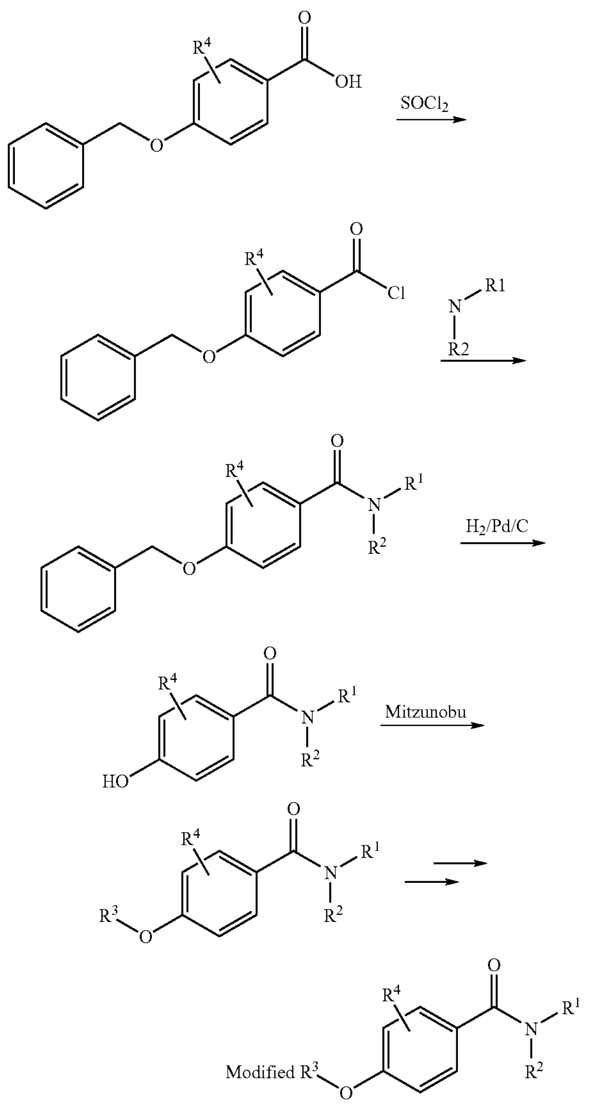

Synthesis scheme 2:

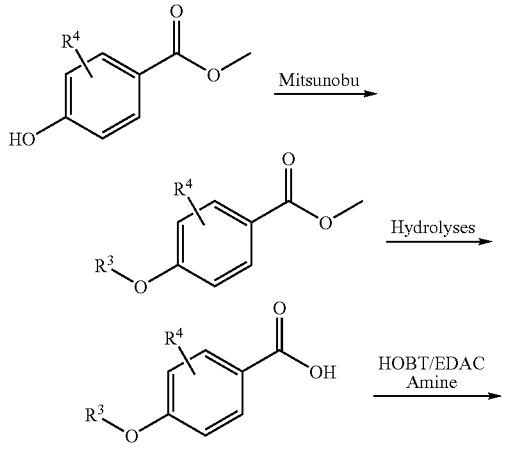

-continued

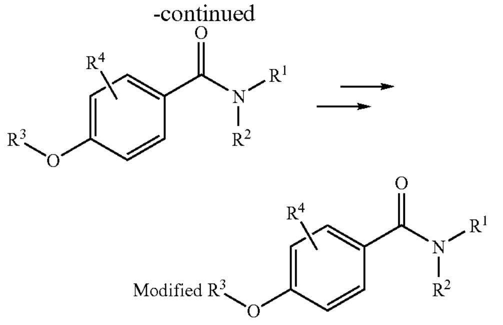

Synthesis scheme 3:

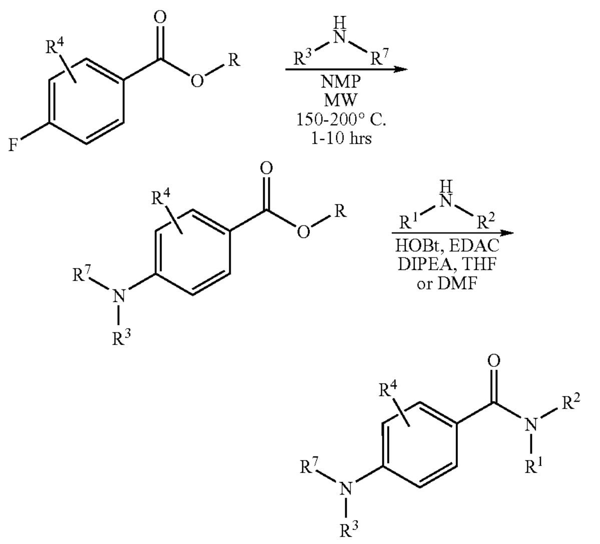

R is $C_1$-$C_6$alkyl or aryl$C_1$-$C_6$alkyl;

General Example A

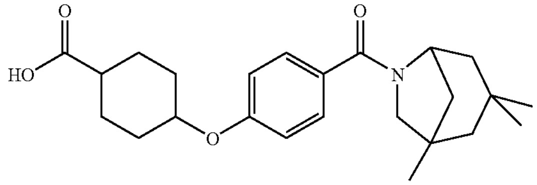

4-[4-(1,3,3-Trimethyl-6-aza-bicyclo[3.2.1]octane-6-carbonyl)-phenoxy]cyclohexanecarboxylic acid 4-(4-Ethoxycarbonyl-cyclohexyloxy)-benzoic acid benzyl ester To a solution of benzyl 4-hydroxybenzoate (50 g, 0.22 mol) and triphenylphosphine (63.2 g, 0.241 mol) dissolved in THF (800 mL) was added 4-hydroxy-cyclohexanecarboxylic acid ethyl ester (35.3 mL, 0.22 mol). The reaction mixture was cooled on an ice bath and DEAD (38 ml, 0.241 mol) was added dropwise maintaining the temperature at 0° C. The resulting mixture was allowed slowly to reach room temperature and stirred for 16 hrs. at this temperature. The volume was reduced to app. 250 mL by evaporation and to the resulting mixture was added water (500 mL) followed by extraction with DCM (3×400 mL). The combined organic phases were washed with brine (400 mL), dried ($Na_2SO_4$), filtered and the volatiles evaporated in vacuo. Crude product ~80 g was purified on column chromatography (Flash 75) using first heptane (7.5 L) followed by a mixture of EtOAc-heptane (1:10) (5 L) and finally a mixture of EtOAc-heptane (1:6) (8 L). Combined fractions were evaporated in vacuo affording 18.1 g (22%) of 4-(4-ethoxycarbonyl-cyclohexyloxy)-benzoic acid benzyl ester as an oil.

$^1$H-NMR (300 MHz, $CDCl_3$) δ 1.26 (t, 3H), 1.42-1.83 (m, 4H), 1.85-2.26 (m, 4H), 2.27-2.48 (m, 1H), 4.14 (q, 2H), 4.22-4.38 (m, 0.5H), 4.55 (br.s., 0.5H), 5.33 (s, 2H), 6.89 (dd, 2H), 7.27-7.49 (m, 5H), 8.01 (d, 2H).

4-(4-Ethoxy-carbonyl-cyclohexyloxy)-benzoic acid

To a solution of the above benzyl ester (36.4 g; 95.2 mmol) dissolved in ethanol (250 mL) was added Pd/C (3.5 g) and the resulting mixture was hydrogenated at 1.0 atm. The catalyst was filtered off and the filtrate evaporated in vacuo affording 26.6 g (96%) of 4-(4-ethoxy-carbonyl-cyclohexyloxy)-benzoic acid as an oil.

$^1$H-NMR (400 MHz, $CDCl_3$) δ 1.27 (t, 3H), 1.45-1.86 (m, 4H), 1.88-2.27 (m, 4H), 2.30-2.50 (m, 1H), 4.09-4.21 (m, 2H), 4.25-4.40 (m, 0.5H), 4.60 (br.s., 0.5H), 6.93 (t, 2H), 8.04 (d, 2H).

To a mixture of the above benzoic acid (22 g, 75.26 mmol) and HOBt (12.2 g, 90.31 mmol) in dry THF (250 mL) was added EDAC (17.3 g, 90.31 mmol) and the resulting mixture was stirred for 10 min. at room temperature at which time 1,3,3-trimethyl-6-aza-bicyclo[3.2.1]-octane, HCl (17.1 g, 75.26 mmol) and DIPEA (29 mL) was added. The mixture was stirred at room temperature for 48 hrs., the volatiles evaporated and to the residue was added water (150 mL) followed by extraction with EtOAc (2×100 mL). The combined organic phases were washed with water (100 mL) and evaporated in vacuo. The residue was re-dissolved in EtOH (100 mL) and to this mixture was added 1N NaOH (150 mL). Stirring was continued for 16 hrs. at room temperature at which time the volatiles were evaporated in vacuo followed by addition of water (100 mL) and diethyl ether (150 mL). The organic phase was separated and the aqueous phase acidified to pH ~1 with conc. HCl followed by extraction with diethyl ester (2×125 mL). The combined organic phases were dried ($Na_2SO_4$), filtered and left for 2 hrs. at room temperature. The precipitate was filtered off and dried in vacuo at 50° C. affording 10.6 g (35%) of the title compound as a solid. The filtrate was evaporated to ½ the volume and seeded. After 16 hrs a second crop was filtered off and dried affording an additional 13.8 g (46%) of the title compound as a solid. $^1$H-NMR (400 MHz, $CDCl_3$) δ 0.94 (d, 3H), 1.03 (d, 3H), 1.12 (d, 3H), 1.17-1.83 (m, 10H), 1.87-2.31 (m, 4H), 2.31-2.49 (m, 1H), 3.22 (d, 0.5H), 3.26-3.36 (m, 1H), 3.58 (d, 0.5H), 3.99-4.11 (m, 0.5H), 4.17-4.31 (m, 0.5H), 4.50 (br.s., 0.5H), 4.56-4.67 (m, 0.5H), 6.82-6.94 (m, 2H), 7.35-7.48 (m, 2H).

m/z: 400 (M+1)+;

In a similar way as described in general example A above the following compounds 9a-40a were made.

| Ex no | Molecule | IUPAC | LC-MS (electrospray) |
|---|---|---|---|
| 1a | 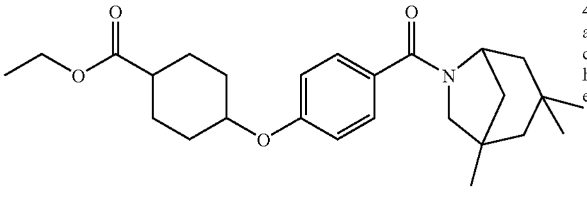 | 4-[4-(1,3,3-Trimethyl-6-aza-bicyclo[3.2.1]octane-6-carbonyl)-phenoxy]-cyclohexanecarboxylic acid ethyl ester | m/z: 428 (M + 1)+ |
| 2a | 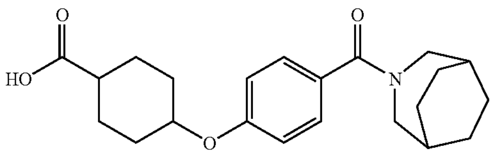 | 4-[4-(3-Aza-bicyclo[3.2.2]-nonane-3-carbonyl)-phenoxy]-cyclohexane carboxylic acid | m/z: 372 (M + 1)+; Rt = 2.6 min. |
| 3a | 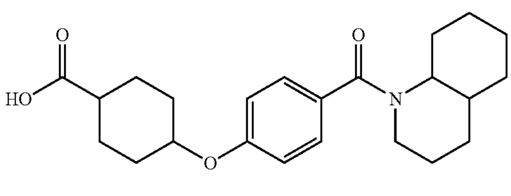 | 4-[4-(Octahydro-quinoline-1-carbonyl)-phenoxy]-cyclohexanecarboxylic acid | m/z: 386 (M + 1)+; Rt = 2.2 min |

-continued

| Ex no | Molecule | IUPAC | LC-MS (electrospray) |
|---|---|---|---|
| 4a | 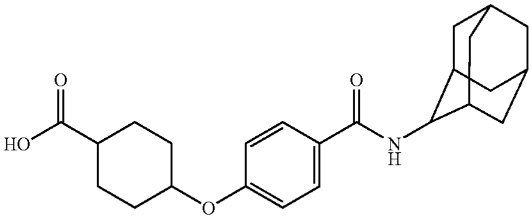 | Cis/trans 4-[4-adamantan-2-ylcarbamoyl)-phenoxy]-cyclohexanecarboxylic acid | m/z: 399 (M + 1)+; Rt = 2.19 min. |
| 5a | 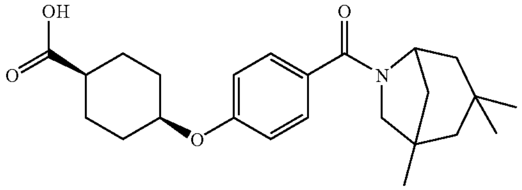 | Cis-4-[4-(1,3,3-trimethyl-6-aza-bicyclo [3.2.1]octane-6-carbonyl)-phenoxy]-cyclo-hexanecarboxylic acid | 1H-NMR (400 MHz, CDCl3) ) δ 0.94(d, 3H), 1.02(d, 3H), 1.12 (d, 3H), 1.17-1.53(m, 4H), 1.53-1.82(m, 5H), 1.89-2.06(m, 4H), 2.26(dd, 1H), 2.40-2.53(m, 1H), 3.22(d, 1H), 3.26-3.35(m, 0.5H), 3.58 (d, 0.5H), 4.01-4.09 (m, 0.5H), 4.46-4.55 (m, 1H), 4.56-4.64(m, 0.5H), 6.89(t, 2H), 7.41(dd, 1H) |
| 6a | 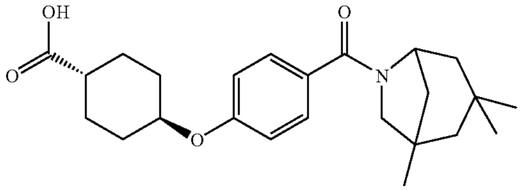 | Trans-4-{4-(1,3,3-trimethyl-6-aza-bicyclo [3.2.1]oct-ane6-carbonyl)-phenoxy]-cyclo-hexanecarboxylic acid | |
| 7a | 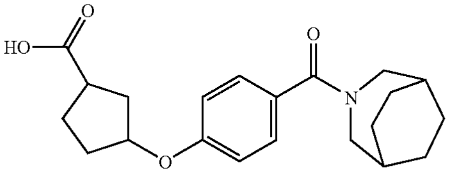 | 3-[4-(3-Aza-bicyclo[3.2.2]-nonane-3-carbonyl)-phenoxy]-cyclopentane-carboxylic acid | m/z: 358 (M + 1)+; Rt = 1.78 min. |
| 8a | 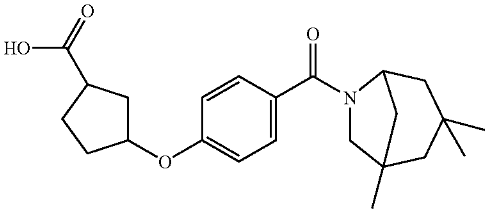 | 3-[4-(1,3,3-Trimethyl-6-aza-bicyclo[3.2.1]octane-6-carbonyl)-phenoxy]-cyclopentane carboxylic acid | m/z: 386 (M + 1)+; Rt = 1.92 min. |
| 9a | 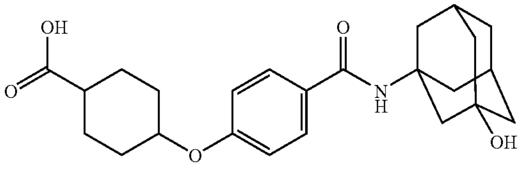 | 4-[4-(3-Hydroxy-ada-mantan-1-ylcarbamoyl)-phenoxy]-cyclohexane-carboxylic acid | m/z: 414 (M + 1)+; Rt = 1.47 min. |
| 10a | 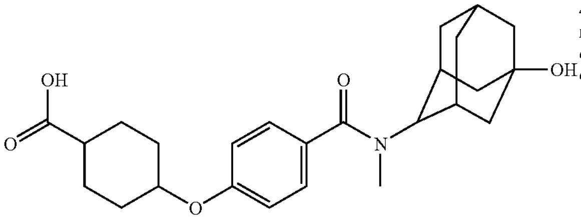 | 4-{4-[(5-Hydroxy-ada-mantan-2-yl)-methyl-carbamoyl]-phen-oxy}-cyclohexanecarboxylic acid | m/z: 429 (M + 1)+; Rt = 1.51 min. |

-continued

| Ex no | Molecule | IUPAC | LC-MS (electrospray) |
|---|---|---|---|
| 11a | 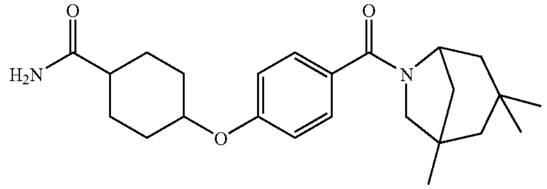 | 4-[4-(1,3,3-Trimethyl-6-aza-bicyclo[3.2.1]octane-6-carbonyl)-phenoxy]-cyclo-hexane carboxylic acid amide | m/z: 400 (M + 1)+; Rt = 1.39 min. |
| 12a | 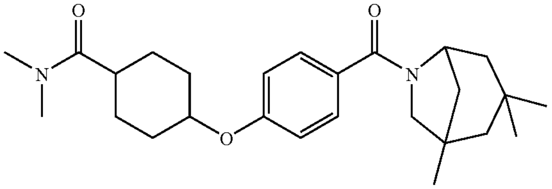 | 4-[4-(1,1,3,3-Trimethyl-6-aza-bicyclo[3.2.1]octane-6-carbonyl)-phenoxy]-cyclo-hexane carboxylic acid di-methylamide | m/z: 414 (M + 1)+; Rt = 1.47 min. |
| 13a | 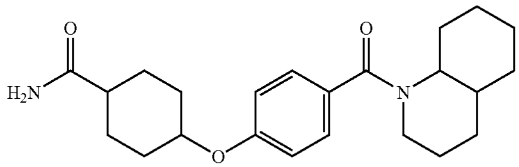 | 4-[4-(Octahydro-quinoline-1-carbonyl)-phenoxy]-cyclo-hexanecarboxylic acid amide | m/z: 385 (M + 1)+; Rt = 1.7 min. |
| 14a | 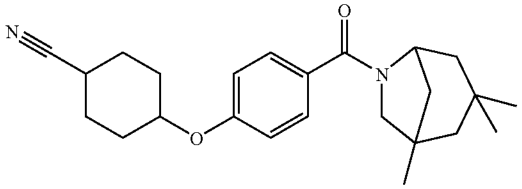 | 4-[4-(1,3,3-Trimethyl-6-aza-bicyclo[3.2.1]octane-6-carbonyl)-phenoxy}-cyclohexane carbonitrile | m/z: 382 (M + 1)+; Rt = 1.65 min. |

Example 11a

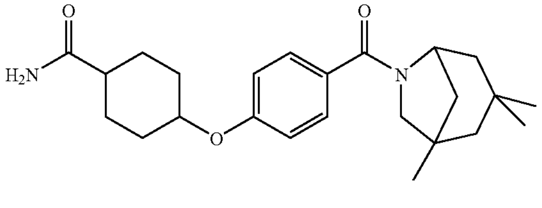

4-[4-(1,3,3-Trimethyl-6-aza-bicyclo[3.2.1]octane-6-carbonyl)-phenoxy]-cyclohexanecarboxylic acid amide To a solution of 4-[4-(1,3,3-trimethyl-6-aza-bicyclo[3.2.1]octane-6-carbonyl)-phenoxy]-cyclohexanecarboxylic acid (4 g, 10.01 mmol) in DCM (75 mL) was added thionylchloride (1.5 mL) and dry DMF (0.5 mL). The resulting mixture was stirred for 16 hrs at room temperature and the volatiles evaporated in vacuo. The residue was dissolved in DCM (50 mL), added dropwise to an ice cooled solution of conc. aqueous ammoniac (150 mL) and TEA (7 mL) and stirred for 1 hr. The phases were separated and the organic phase dried ($Na_2SO_4$), filtered and evaporated which afforded 3.5 g (88%) of the title compound as a solid.

m/z: 400 (M+1)+; Rt=1.39 min.

Example 14a

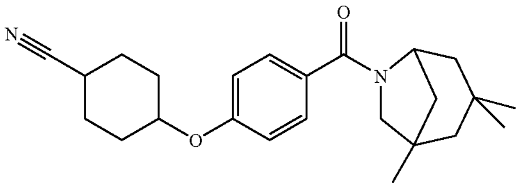

4-[4-(1,3,3-Trimethyl-6-aza-bicyclo[3.2.1]octane-6-carbonyl)-phenoxy]-cyclohexane carbo-nitrile To a solution of the above amide (2 g, 5.02 mmol) in a mixture of DMSO (570 µL) and DCM (150 mL) cooled in a dry ice acetone bath to −78° C. was added dropwise a solution of oxalylchloride (520 µL, 6.02 mmol) in DCM (50 mL). The mixture was stirred for 15 min. at −78° C. followed by dropwise addition of TEA (2.1 mL), stirring was continued for an additional 15 min. at which time the reaction mixture was quenched by addition of water (50 mL). The reaction was allowed to reach room temperature and the phases separated. The aqueous phase was extracted with EtOAc (2×50 mL) and all the combined organic phases were dried ($Na_2SO_4$), filtered and the solvent evaporated in vacuo affording 1.5 g (79%) of crude title compound.

Preparative LC/MS purification afforded after basic workup 400 mg (21%) of the title compound.

$^1$H-NMR (400 MHz, $CDCl_3$) δ 0.91 (br.s., 3H), 1.10 (br.s., 6H), 1.22-1.33 (m, 2H), 1.41 (d, 1H), 1.56 (br.s., 1H), 1.69-1.90 (m, 4H), 1.94-2.23 (m, 4H), 2.62-2.85 (m, 1H), 3.19 (br.s., 1H), 3.79 (br.s., 1H), 4.42 (br.s., 1H), 6.89 (t, 2H), 7.26 (t, 2H).

m/z: 382 (M+1)+; Rt=1.65 min.

Example 12a was made in a similar way as described for example 11a.

General Example B

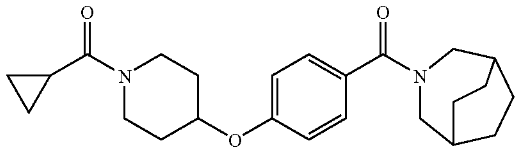

(3-Aza-bicyclo[3.2.2]non-3-yl)-[4-(1-cyclopropane-carbonyl-piperidin-4-yloxy)-phenyl]-methanone 4-(4-Methoxycarbonyl-phenoxy)-piperidine-1-carboxylic acid t-butyl ester To a stirred solution of 4-hydroxy benzoic acid methyl ester (5.0 g, 32.86 mmol) in dry THF (400 mL) was added triphenyl phosphine (12.93 g, 49.29 mmol) and 1-t-butoxy-carbonyl-4-hydroxypiperidine (6.61 g, 32.86 mmol). The reaction mixture was cooled to 0° C. and DEAD (7.76 mL, 49.29 mmol) was added dropwise over a period of 1 h. The reaction was gradually brought to room temperature and stirring continued for 16 hrs. The solvent was removed under vacuum and ether (100 mL) was added and cooled to 0° C. The solid formed was filtered off and the clear filtrate concentrated and purified by column chromatography (100% heptane to 35% AcOEt in heptane). Desired fractions were pooled and the solvent evaporated in vacuo affording 6.14 g (56%) of 4-(4-methoxycarbonyl-phenoxy)-piperidine-1-carboxylic acid t-butyl ester as an oil.

$^1$H-NMR (400 MHz, $CDCl_3$) δ 1.47 (s, 9H), 1.70-1.84 (m, 2H), 1.87-2.01 (m, 2H), 3.30-3.43 (m, 2H), 3.64-3.76 (m, 2H), 3.88 (s, 3H), 4.51-4.62 (m, 1H), 6.91 (d, 2H), 7.99 (d, 2H).

4-(Piperidin-4-yloxy)-benzoic acid methyl ester

To a solution of 4-(4-methoxycarbonyl-phenoxy)-piperidine-1-carboxylic acid t-butyl ester (6 g, 17.89 mmol) in DCM (50 mL) was added TFA (25 mL) and stirring was continued for 1.5 hrs at room temperature. The volatiles were removed in vacuo and the residues was crystallised from diethyl ether affording after filtration and drying 5.92 g (95%) of 4-(piperidin-4-yloxy)-benzoic acid methyl ester as a solid TFA salt.

$^1$H-NMR (400 MHz, $CDCl_3$) δ 2.06-2.36 (m, 4H), 3.15-3.29 (m, 2H), 3.29-3.43 (m, 2H), 3.89 (s, 3H), 4.76 (br.s., 1H), 6.93 (d, 2H), 8.01 (d, 2H), 9.43 (br.s., 1H), 9.70 (br.s., 1H). m/z: 236.2 (M+1)+;

4-(1-Cyclopropanecarbonyl-piperidin-4-yloxy)-benzoic acid methyl ester

To a solution of cyclopropanecarboxylic acid (246 mg, 2.86 mmol) in DMF (20 mL) was added HOBt (658 mg, 4.29 mmol) and EDAC (549 mg, 2.86 mmol). The mixture was stirred at room temperature for 1 hr at which time 4-(piperidin-4-yloxy)-benzoic acid methyl ester, TFA salt (1000 mg, 2.86 mmol) and DIPEA (549 μL, 3.15 mmol) were added. After stir-ring for 16 hrs at room temperature the volatiles were evaporated in vacuo and the residue dissolved in AcOEt (25 mL). The organic phase was washed with aqueous $NaHCO_3$, dried (MgSO4), filtered and evaporated in vacuo affording 770 mg (88%) of the 4-(1-cyclopropanecarbonyl-piperidin-4-yloxy)-benzoic acid methyl ester as a solid.

$^1$H-NMR (400 MHz, $CDCl_3$) δ 0.73-0.83 (m, 2H), 0.95-1.04 (m, 2H), 1.72-2.10 (m, 5H), 3.60-3.73 (m, 2H), 3.80 (br.s., 1H), 3.91 (s, 3H), 3.93 (br.s., 1H), 4.61-4.72 (m, 1H), 6.92 (d, 2H), 7.99 (d, 2H).

4-(1-Cyclopropanecarbonyl-piperidin-4-yloxy)-benzoic acid

A mixture of 4-(1-cyclopropanecarbonyl-piperidin-4-yloxy)-benzoic acid methyl ester (0.75 g, 2.472 mmol), methanol (25 mL) and 1 N NaOH (10 mL) was stirred at room temperature for 16 hrs. The volatiles were evaporated in vacuo and the residue was redissolved in water (10 mL) and washed with EtOAc (2×5 mL). The aqueous phase was acidified to pH ~1 with 1N HCl and extracted with EtOAc (2×10 mL), dried ($MgSO_4$), filtered and evaporated affording 0.6 g 84%) of 4-(1-cyclopropanecarbonyl-piperidin-4-yloxy)-benzoic acid as a solid. $^1$H-NMR (400 MHz, $CDCl_3$) δ 0.73-0.84 (m, 2H), 0.97-1.07 (m, 2H), 1.72-2.11 (m, 5H), 3.63-3.74 (m, 2H), 3.75-4.00 (m, 2H), 4.64-4.75 (m, 1H), 6.96 (d, 2H), 8.06 (d, 2H).

To a solution of 4-(1-cyclopropanecarbonyl-piperidin-4-yloxy)-benzoic acid (100 mg, 0.346 mmol) in DMF (6 mL) was added HOBt (80 mg, 0.518 mmol) and EDAC (67 mg, 0.346 mmol). The mixture was stirred at room temperature for 1 hr at which time 3-azabicyclo-[3.2.2]nonane (52 mg, 0.415 mmol) was added. After stirring for 16 hrs at room temperature the volatiles were evaporated in vacuo and the residue purified on prep-HPLC (Gilson). Pure fractions were collected and the volatiles evaporated affording 125 mg (91%) of the title compound as an oil.

$^1$H-NMR (400 MHz, $CDCl_3$) δ 0.71-0.84 (m, 2H), 0.94-1.05 (m, 2H), 1.59-2.32 (m, 16H), 3.49-3.73 (m, 3H), 3.74-3.99 (m, 4H), 4.54-4.66 (m, 1H), 6.92 (d, 2H), 7.35 (d, 2H).

In a similar way as described in general example B above the following compounds 1b-5b were made.

| Ex no | Molecule | IUPAC | LC-MS (electrospray) |
|---|---|---|---|
| 1b | 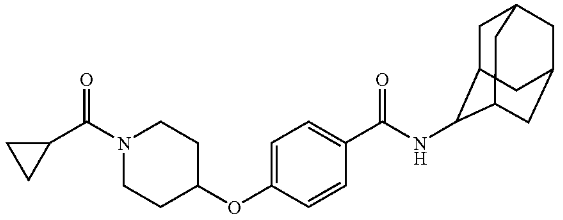 | 4-(1-Cyclopropanecarbonyl-piperidin-4-yloxy)-N-adamantan-2-yl-benzamide | m/z: 423 (M + 1)+; Rt = 2.06 min. |
| 2b | 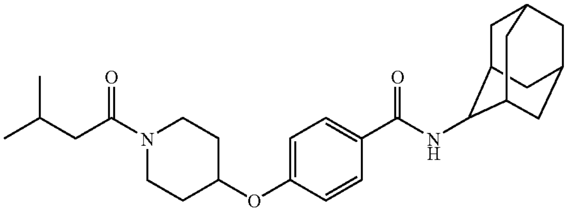 | 4-[1-(3-Methyl-butyryl)-piperidin-4-yloxy]-N-adamantan-2-yl-benzamide | m/z: 439 (M + 1)+; Rt = 2.21 min. |
| 3b | 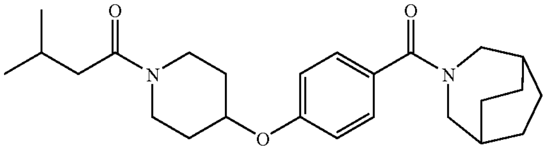 | 1-{4-[4-(3-Aza-bicyclo-[3.2.2]nonane-3-carbonyl)-phenoxy]-piperidin-1-yl}-3-methyl-butan-1-one | m/z: 413 (M + 1)+; Rt = 2.01 min. |
| 4b | 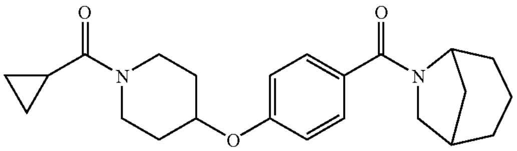 | (6-Aza-bicyclo[3.2.1]oct-6-yl)-[4-(1-cyclopropane-carbonyl-piperidin-4-yloxy)-phenyl]-methanone | m/z: 384 (M + 1)+; Rt = 1.67 min. |
| 5b | 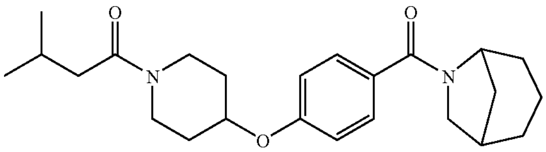 | 1-{4-[4-(6-Aza-bicyclo[3.2.1]-octane-6-carbonyl)-phenoxy]-piperidin-1-yl}-3-methyl-butan-1-one | m/z: 400 (M + 1)+; Rt = 1.84 min. |

General Example C

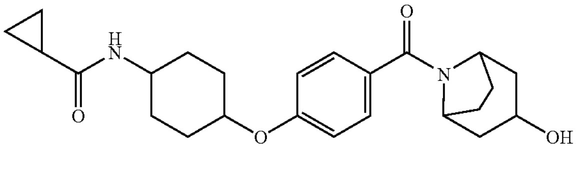

Cycloprobanecarboxylic acid {4-[4-(3-hydroxy-8-aza-bicyclo[3.2.1]octane-8-carbonyl)-phenoxy]-cyclohexyl}-amide 2-(4-Hydroxy-cyclohexyl)-isoindole-1,3-dione $K_2CO_3$ (19.4 g, 140.6 mmol) was added to a solution of trans-4-aminocyclohexanol hydrochloride (9.0 g, 59.35 mmol) in water (150 mL) followed by N-carbethoxy phthalimide (18.8 g, 85.96 mmol). A white precipitate was formed immediately. Stirring continued at RT for 1 h. The precipitate was filtered off, washed with water and dried to afford 12 g (84%) of 2-(4-hydroxy-cyclohexyl)-isoindole-1,3-dione.

$^1$H-NMR (300 MHz, DMSO-$d_6$) δ 1.18-1.40 (m, 3H), 1.60-1.76 (m, 2H), 1.80-2.00 (m, 2H), 2.04-2.23 (dq, 2H), 3.40-3.50 (m, 1H), 3.89-4.03 (tt, 1H), 4.6 (br.s, 1H,), 7.15-7.39 (m, 1H), 7.80 (m, 3H).

m/z: 246 (M+1)+

4-[4-(1,3-Dioxo-1,3-dihydro-isoindol-2-yl)-cyclohexyloxy]-benzoic acid ethyl ester To a stirred solution of 2-(4-hydroxycyclohexyl)isoindole-1,3-dione (8.0 g, 32.6 mmol) in dry THF (100 mL) was added triphenyl phosphine (12.8 g, 48.8 mmol) and 4-hydroxy benzoic acid ethyl ester (5.44 g, 32.7 mmol). The reaction mixture was cooled to 0° C. and DIAD (9.6 g, 47.4 mmol) was added dropwise from an addition funnel over a period of 3 h. The reaction was gradually brought to room temperature and stirring continued for 3 h. The solvent was removed under vacuum and ether (100 mL) was added and cooled to 0° C. The solid formed was filtered and the clear filtrate concentrated and purified by column chromatography over neutral alumina (8% AcOEt in hexane) to give 5.13 g (42%) of 4-[4-(1,3-dioxo-1,3-dihydro-isoindol-2-yl)-cyclohexyloxy]-benzoic acid ethyl ester.

$^1$H-NMR (300 MHz, $CDCl_3$); δ 1.24-1.36 (m, 2H), 1.40 (t, 3H), 1.63-1.77 (m, 3H), 2.19-2.29 (m, 2H), 2.62-2.79 (dq,

2H), 4.15-4.72 (m, 1H), 4.35 (q, 2H), 7.01 (d, 2H), 7.71 (m, 2H), 7.82 (m, 2H), 8.0 (d, 2H).

m/z: 394.1 (M+1)+

4-(4-Aminocyclohexyloxy)benzoic acid ethyl ester

To a solution of 4-[4-(1,3-dioxo-1,3-dihydro-isoindol-2-yl)-cyclohexyloxy]-benzoic acid ethyl ester (6.3 g, 16.0 mmol) in $CHCl_3$ (50 mL) and ethanol (60 mL) was added hydrazine hydrate (16.0 g, 320.2 mmol). Stirring was continued at ambient temperature for 2 days. The reaction mixture was then cooled to 5-10° C. and the white precipitate was filtered off. The filtrate was washed with water, dried and the solvent evaporated under vacuum to afford 4.15 g (98%) of 4-(4-amino-cyclohexyloxy)-benzoic acid ethyl ester.

$^1$H-NMR (300 MHz, DMSO-$d_6$); δ1.30 (t, 3H), 1.39-1.50 (m, 2H), 1.52-1.70 (m, 4H), 1.84-1.98 (m, 2H), 2.70-2.80 (m, 1H), 3.20-3.45 (br.s, 2H), 4.25 (2H, q), 4.58 (m, 1H), 7.0 (d, 2H), 7.9 (d, 2H).

4-[4-(Cyclopropanecarbonyl-amino)-cyclohexyloxy]-benzoic acid ethyl ester

To a solution of 4-(4-aminocyclohexyloxy)benzoic acid ethyl ester (4.15 g, 15.76 mmol) in DCM (40 mL) at 0° C. was added TEA (1.6 g, 15.7 mmol) followed by cyclopropane carbonyl chloride (1.98 g, 18.9 mmol) over a period of 1 hr. Stirring was continued at 0-5° C. for 2 h. Water (40 mL) was then added and extracted with EtOAc. The organic layer was washed with 2N HCl, satd.$NaHCO_3$ and brine solution. It was dried and concentrated under vacuum affording 4.75 g (91%) of 4-[4-(cyclopropanecarbonyl-amino)-cyclohexyloxy]-benzoic acid ethyl ester as an oil.

$^1$H-NMR (300 MHz, $CDCl_3$); δ0.7-0.8 (m, 2H), 0.94-1.02 (m, 2H), 1.26-1.35 (m, 1H), 1.38 (t, 3H), 1.58-1.64 (m, 2H), 1.68-1.86 (m, 4H), 2.00-2.10 (m, 2H), 3.95 (m, 1H), 4.38 (q, 2H), 4.60 (m, 1H), 6.90 (d, 2H), 8.00 (d, 2H).

m/z: 332 (M+1)+

4-[4-(Cyclopropanecarbonyl-amino)-cyclohexyloxy]-benzoic acid

To a solution of 4-[4-(cyclopropanecarbonylamino)cyclohexyloxy]benzoic acid ethyl ester (4.75 g, 14.3 mmol) in EtOH (30 mL) and THF (10 mL) was added NaOH (2.29 g, 57.3 mmol) in 10 ml of water. Stirring was continued at ambient for 17 hrs. The solvents were removed under vacuum, water (50 mL) was added and the whole extracted with EtOAc. The aqueous layer was acidified to pH ~2 with 2N HCl and the white precipitate obtained was filtered off and washed with hexane affording 4.0 g (92%) of 4-[4-(cyclopropanecarbonyl-amino)-cyclohexyloxy]-benzoic acid as a solid.

$^1$H-NMR (300 MHz, DMSO-$d_6$); δ0.82 (m, 4H), 1.50-1.78 (m, 7H), 1.83-2.00 (m, 2H), 3.64-3.80 (m, 1H), 4.58-4.65 (m, 1H), 7.0 (d, 2H), 7.86 (d, 2H), 8.02 (d, 1H), 12.6 (s, 1H).

m/z: 304 (M+1)+

Cyclopropanecarboxylic acid {4-[4-(3-hydroxy-8-aza-bicyclo[3.2.1]octane-8-carbonyl)-phenoxy]-cyclohexyl}-amide To a solution of 4-[4-(cyclopropanecarbonylamino)cyclohexyloxy]benzoic acid (150 mg, 0.494 mmol) in DMF (2 mL) was added HOBt (67 mg, 0.49 mmol) and DIEA (256 mg, 1.98 mmol). The reaction mixture was cooled to 0° C. and 8-azabicyclo[3.2.1]octan-3-ol (81 mg, 0.49 mmol) was added. Stirring was continued at 0° C. for 10 min after which EDCI (107 mg, 0.543 mmol) was added to the reaction mixture. The reaction was gradually brought to room temperature and stirred for 16 hrs. It was concentrated under vacuum, water (5 mL) was added and extracted with DCM (30 mL). The organic layer was washed with 2N HCl, sat. aq. $NaHCO_3$ solution and finally with brine and concentrated in vacuo to afford crude amide. It was recrystallized from EtOAc-pentane affording 170 mg (82%) of the title compound as a solid.

$^1$H-NMR (300 MHz, DMSO-$d_6$) δ 0.80 (m, 4H), 1.50-2.24 (m, 17H), 3.60-3.80 (m, 2H), 3.90-4.20 (m, 2H), 4.40-4.60 (m, 2H), 6.95 (d, 2H), 7.40 (d, 2H), 8.00 (d, 1H).

m/z: 413 (M+1)+

In a similar way as described in general example C above the following compounds 1c-11c were made.

| Ex no | Molecule | IUPAC | LC-MS (electrospray) |
|---|---|---|---|
| 1c | 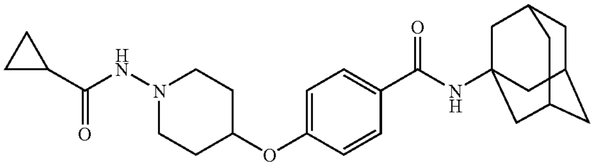 | cis/trans-4-[4-(Cyclopropane carbonyl-amino)-cyclohexyl-oxy]-N-adamantan-1-yl-benzamide | m/z: 438 (M + 1)+; Rt = 2.24 min. |
| 2c | 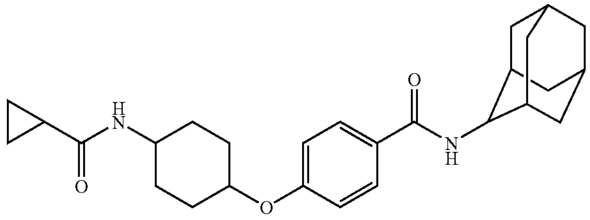 | cis/trans-4-[4-(Cyclopropane carbonyl-amino)-cyclohexyl-oxy]-N-adamantan-2-yl-benzamide | m/z: 437 (M + 1)+; Rt = 2.09 min. |

-continued

| Ex no | Molecule | IUPAC | LC-MS (electrospray) |
|---|---|---|---|
| 3c | 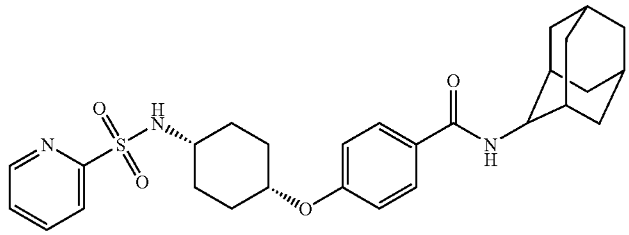 | Cis-N-Adamantan-2-yl-4-[4-(pyridine-2-sulfonylamino)-cyclohexyloxy]-benzamide | m/z: 510 (M + 1)+; Rt = 2.15 min. |
| 4c | 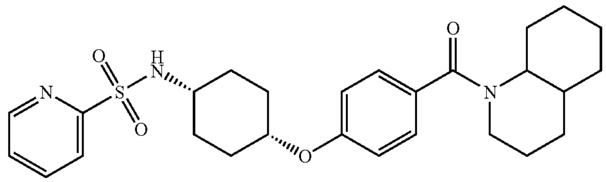 | Cis-Pyridine-2-sulfonic acid {4-[4-(octahydro-quinoline-1-carbonyl)-phenoxy]-cyclohexyl}-amide | m/z: 498 (M + 1)+; Rt = 2.07 min. |
| 5c | 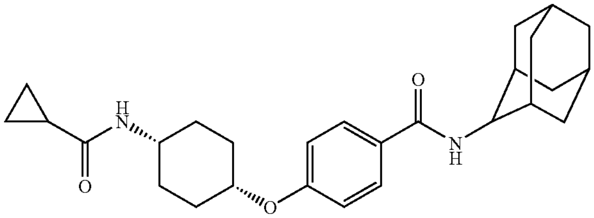 | Cis-N-Adamantan-2-yl-4-[4-(cyclopropanecarbonyl-amino)-cyclohexyloxy]-benzamide | m/z: 437 (M + 1)+; Rt = 2.08 min. |
| 6c | 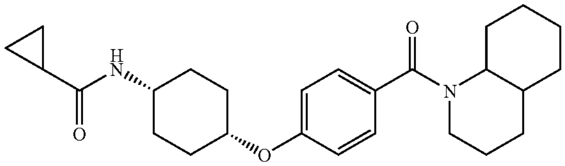 | Cis-Cyclopropanecarboxylic acid {4-[4-(octahydro-quinoline-1-carbonyl)-phenoxy]-cyclohexyl}-amide | m/z: 425 (M + 1)+; Rt = 1.99 min. |
| 7c | 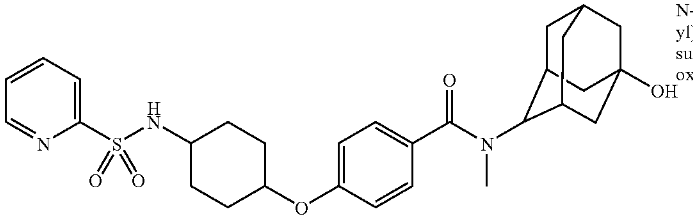 | N-(5-Hydroxy-adamantan-2-yl)-N-methyl-4-[4-(pyridine-2-sulfonylamino)-cyclohexyl-oxy]-benzamide | m/z: 540 (M + 1)+; Rt = 1.57 & 1.62 min. Cis/trans-mixture |
| 8c | 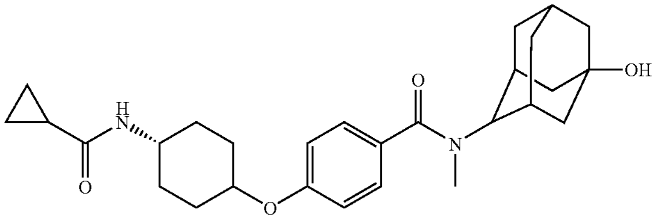 | 4-[4-(Cyclopropanecarbonyl-amino)-cyclohexyloxy]-N-(5-hydroxy-adamantan-2-yl)-N-methyl-benzamide | m/z: 467 (M + 1)+; Rt = 1.49 & 1.54 min. Cis/trans-mixture. |
| 9c | 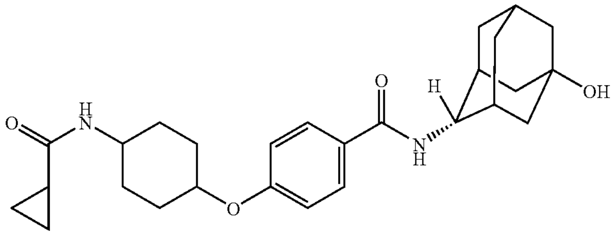 | 4-[4-(Cyclopropanecarbonyl-amino)-cyclohexyloxy]-N-(Z)-(5-hydroxy-adamantan-2-yl)-benzamide | m/z: 454 (M + 1)+; Rt = 1.58 min. |

-continued

| Ex no | Molecule | IUPAC | LC-MS (electrospray) |
|---|---|---|---|
| 10c | 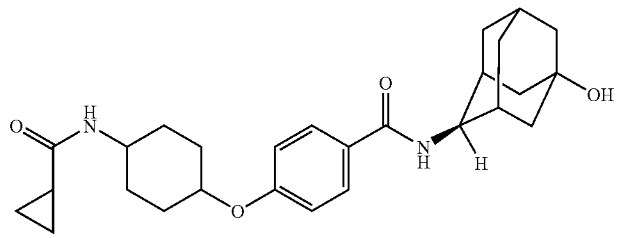 | 4-[4-(Cyclopropanecarbonyl-amino)-cyclohexyloxy]-N-(E)-(5-hydroxy-adamantan-2-yl)-benzamide | m/z: 454 (M + 1)+; Rt = 1.55 min. |

General Example D

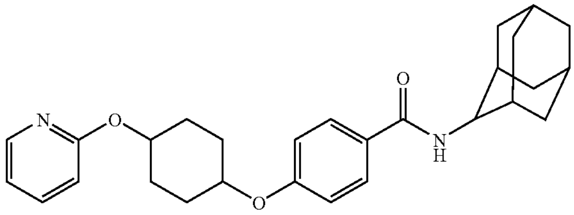

4-[4-(Pyridin-2-yloxy)-cyclohexyloxy]-N-adamantan-2-yl-benzamide

4-(t-Butyl-diphenyl-silanyloxy)-cis/trans-cyclohexanol

To a solution of 1,4-cyclohexanediole (20 g, 0.172 mol) and imidazole (11.72 g, 0.172 mol) in a mixture of DCM/DMF 2:1 (600 mL) was added a solution of t-butyl-chloro-diphenylsilane (47.33 g, 0.172 mol) in DCM (150 mL) and the resulting mixture was stirred for 16 hrs at room temperature. The mixture was washed with aq. sat. $NH_4Cl$ (2×100 mL), aq. sat. $NaHCO_3$ (2×100 mL) and water (100 mL). The organic phase was dried ($MgSO_4$), filtered and evaporated in vacuo affording 50.8 g (83%) of 4-(t-butyl-diphenyl-silanyloxy)-cis/trans-cyclohexanol as an oil.

1H-NMR (400 MHz, $CDCl_3$) □ 1.01 (s, 1H), 1.03-1.10 (m, 9H), 1.10-1.23 (m, 1H), 1.28-1.49 (m, 2H), 1.56-1.67 (m, 1H), 1.67-1.83 (m, 3H), 1.83-1.94 (m, 1H), 3.59-3.77 (m, 1H), 3.81-3.89 (m, 1H), 4.12 (q, 1H), 7.30-7.47 (m, 6H), 7.59-7.74 (m, 4H), m/z: 355 (M+1)+;

N-Adamantan-2-O-4-[4-(t-butyl-diphenyl-silanyloxy)-cyclohexyloxy]-benzamide

To a stirred solution of N-adamantan-2-yl-4-hydroxy-benzamide (4 g, 14.74 mmol) in dry THF (100 mL) and DMF (75 mL) was added triphenyl phosphine (5.8 g, 22.11 mmol) and 4-(t-butyl-diphenyl-silanyloxy)-cyclohexanol (6.27 g, 17.69 mmol). The reaction mixture was cooled to 0° C. and DEAD (3.48 mL, 22.11 mmol) was added dropwise from an addition funnel over a period of 30 min. The reaction was gradually brought to room temperature and stirring continued for 16 hrs. The solvent was removed under vacuum and ether (100 mL) was added and cooled to 0° C. The solid formed was filtered off and the clear filtrate concentrated and purified by column chromatography using DCM as solvent to give 4.73 g (53%) of N-adamantan-2-yl-4-[4-(t-butyl-diphenyl-silanyloxy)-cyclohexyloxy]-benzamide as an oil.

m/z: 609 (M+1)+;

N-Adamantan-2-yl-4-(4-hydroxy-cyclohexyloxy)-benzamide

To a solution of N-adamantan-2-yl-4-[4-(t-butyl-diphenyl-silanyloxy)-cyclohexyloxy]-benzamide (4.73 g, 7.78 mmol) in dry THF (50 mL) was added a 1N TBAF solution in THF (31, 12 mL) and the mixture was stirred for 48 hrs. at room temperature. The volatiles were evaporated in vacuo and the residue redissolved in AcOEt (50 mL) and washed with 5% aqueous citric acid and vand. The organic phase was dried ($MgSO_4$), filtered and the solvent evaporated in vacuo. The residue was purified using a Combi Flash Sq16× with a solvent gradient starting from AcOEt/heptan (20:80) to (85:15). Desired fractions were collected and the solvent evaporated in vacuo affording 780 mg (27%) of N-adamantan-2-yl-4-(4-hydroxy-cyclohexyloxy)-benzamide as a solid.

$^1$H-NMR (300 MHz, $CDCl_3$) δ 0.78-1.01 (m, 1H), 1.11-1.42 (m, 4H), 1.43-2.17 (m, 18H), 3.73-3.90 (m, 1H), 4.20-4.29 (m, 1H), 4.41-4.54 (m, 1H), 6.34 (d, 1H), 6.93 (d, 2H), 7.73 (d, 2H).

m/z: 370 (M+1)+;

To a stirred solution of N-adamantan-2-yl-4-(4-hydroxy-cyclohexyloxy)-benzamide (150 mg, 0.41 mmol) in dry THF (10 mL) was added triphenyl phosphine (160 mg, 0.61 mmol) and 2-hydroxypyridine (38.6 mg, 0.41 mmol). The reaction mixture was cooled to 0° C. and DEAD (96 μL, 0.61 mmol) was added. The reaction was gradually brought to room temperature and stirring continued for 16 hrs. The solvent was removed in vacuo and purified by prep. HPLC. Desired fractions were pooled and the solvent evaporated in vacuo affording 30 mg (17%) of the title compound as a solid.

1H-NMR (400 MHz, $CDCl_3$) δ 1.63-1.81 (m, 8H), 1.81-1.95 (m, 8H), 2.02 (br.s., 2H), 2.17 (t, 4H), 4.15-4.31 (m, 1H), 4.40-4.53 (m, 1H), 5.08-5.21 (m, 1H), 6.36 (d, 1H), 6.74 (d, 1H), 6.82-6.91 (m, 1H), 6.95 (d, 2H), 7.56-7.65 (m, 1H), 7.73 (d, 2H), 8.17 (d, 1H).

m/z: 447 (M+1)+;

In a similar way as described in general example D above the following compounds 1d-4-d were made.

| Ex no | Molecule | IUPAC | LC-MS (electrospray) |
|---|---|---|---|
| 1d | 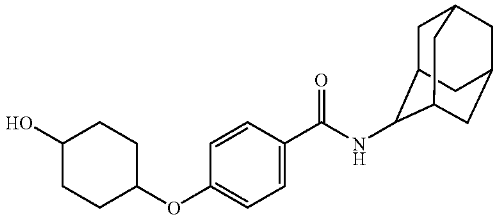 | N-Adamantan-2-yl-4-(4-hydroxy-cyclohexyloxy)-benzamide | m/z: 370 (M + 1)+; Rt = 1.94 min. |
| 2d | 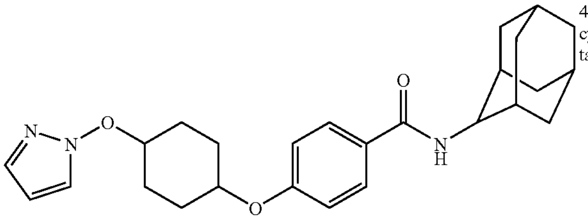 | 4-[4-(Pyrazol-1-yloxy)-cyclohexyloxy]-N-adamantan-2-yl-benzamide | m/z: 436 (M + 1)+; Rt = 2.43 min. |
| 3d | 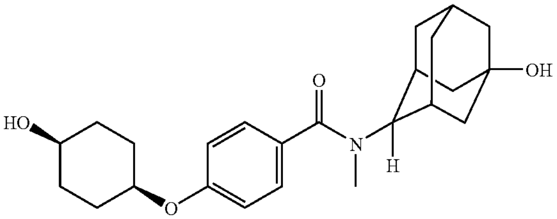 | N-(cis-5-Hydroxy-adamantan-2-yl)-4-(cis-4-hydroxy-cyclohexyl-oxy)-N-methyl-benzamide | |
| 4d | 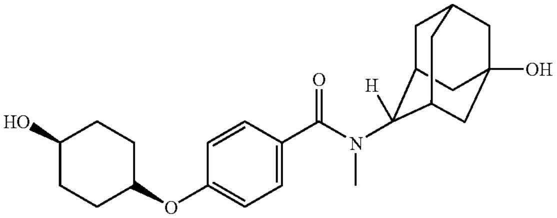 | N-(trans-5-Hydroxy-adamantan-2-yl)-4-(cis-4-hydroxy-cyclo-hexyl-oxy)-N-methyl-benzamide | |

General Example E

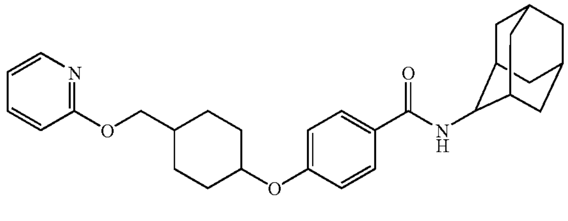

4-[4-(Pyridin-2-yl-oxy-methyl)-cyclohexyloxy]-N-adamantan-2-yl-benzamide

4-[4-(Adamantan-2-ylcarbamoyl)-phenoxy]-cyclohexanecarboxylic acid ethyl ester

To a stirred solution of N-adamantan-2-yl-4-hydroxy-benzamide (6 g, 22.11 mmol) in dry THF (100 mL) was added triphenyl phosphine (8.7 g, 33.17 mmol) and 4-hydroxy cyclo-hexane carboxylic acid ethyl ester (4.57 g, 26.53 mmol). The reaction mixture was cooled to 0° C. and DEAD (5.22 mL, 33.17 mmol) was added dropwise from an addition funnel over a period of 30 min. The reaction was gradually brought to room temperature and stirring continued for 48 hrs. The solvent was removed under vacuum and ether (100 mL) was added and cooled to 0° C. The solid formed was filtered off and the clear filtrate concentrated and purified by column chromatography (Gyan-flash). Desired fractions were collected and the solvent evaporated. The residue was crystallised from diethyl ether and filtered off affording 3 g (32%) of 4-[4-(adamantan-2-ylcarbamoyl)-phenoxy]-cyclohexane carboxylic acid ethyl ester as a solid.

$^1$H-NMR (400 MHz, $CDCl_3$) δ 1.27 (t, 3H), 1.41-2.25 (m, 22H), 2.30-2.47 (m, 1H), 4.10-4.20 (m, 2H), 4.21-4.30 (m, 1H), 4.55 (br.s., 1H), 6.34 (d, 1H), 6.92 (t, 2H), 7.73 (d, 2H). m/z: 427 (M+1)+

N-Adamantan-2-yl-4-(4-hydroxymethyl-cyclohexyloxy)-benzamide

In a flame dried flask was 4-[4-(adamantan-2-ylcarbamoyl)-phenoxy]-cyclohexane carboxylic acid ethyl ester (2 g, 4.7 mmol) dissolved in dry THF (300 mL) and cooled to −35° C. To this solution was added 1M DIBAL in toluene (14 mL, 14.1 mmol) and the mixture was stirred at −35° C. for 3 hrs. and left in a freezer at −18° C. for 16 hrs. Due to incomplete reaction an additional portion of 1M DIBAL (5 mL) was added and the mixture was stirred at −18° C. for 1 hr. The reaction was quenched by slowly addition of sat. aq. NH4Cl followed by evaporation to ¼ of the volume and extracted with DCM (3×50 mL). The combined organic phases were evaporated in vacuo and the residue purified using column chromatography (Isco, 120 gram column) and a solvent gradient of heptane/AcOEt from 0 to 100%. Desired fractions were collected and the solvent evaporated in vacuo affording 1 g (60%) of N-adamantan-2-yl-4-(4-hydroxymethyl-cyclohexyloxy)-benzamide as an oil.

$^1$H-NMR (400 MHz, $CDCl_3$) δ 1.05-1.20 (m, 1H), 1.29-1.66 (m, 7H), 1.66-1.85 (m, 5H), 1.85-1.96 (m, 6H), 1.99-2.11 (m, 3H), 2.21 (d, 1H), 3.52 (t, 2H), 4.19-4.28 (m, 2H), 4.62 (br.s., 1H), 6.34 (d, 1H), 6.92 (t, 2H), 7.72 (d, 2H).

To a solution of N-adamantan-2-yl-4-(4-hydroxymethyl-cyclohexyloxy)-benzamide (150 mg, 0.39 mmol) in dry THF (5 mL) was added 2-hydroxypyridine (38 mg, 0.4 mmol) followed by tributyl phosphine (144 μL, 0.59 mmol). The resulting mixture was cooled and azodicarboxylic dipiperidide (149 mg, 0.59 mmol) dissolved in dry THF (3 mL) was added. The mixture was stirred for 6 hrs. at room temperature, filtered and the volatiles evaporated in vacuo. The residue was purified on prep. HPLC and the desired fractions collected and the solvent evaporated in vacuo affording 87 mg (48%) of the title compound as a solid.

$^1$H-NMR (400 MHz, $CDCl_3$) δ 1.27 (q, 1H), 1.44-1.81 (m, 9H), 1.81-1.97 (m, 9H), 1.99-2.12 (m, 3H), 2.17-2.26 (m, 1H), 4.17 (dd, 2H), 4.21-4.32 (m, 1H), 4.64 (br.s., 1H), 6.35 (d, 1H), 6.77 (dd, 1H), 6.87-6.97 (m, 3H), 7.57-7.66 (m, 1H), 7.72 (d, 2H), 8.15-8.21 (m, 1H). m/z: 461 (M+1)+;

In a similar way as described in general example E above the following compounds 1e-4-e were made.

| Ex no | Molecule | IUPAC | LC-MS (electrospray) |
|---|---|---|---|
| 1e | 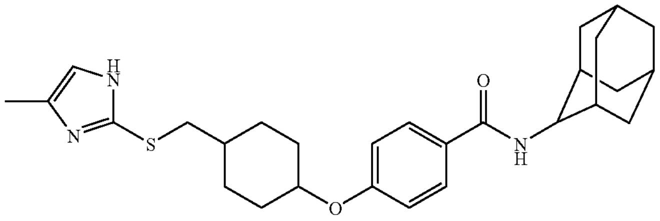 | N-Adamantan-2-yl-4-[4-(4-methyl-1H-imidazol-2-yl-sulfanylmethyl)-cyclo-hexyloxy]-benzamide | m/z: 481 (M + 1)+; Rt = 1.78 min |
| 2e | 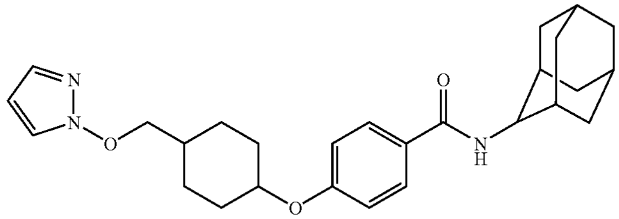 | 4-[4-(Pyrazol-1-yl-oxy-methyl)-cyclohexyloxy]-N-adamantan-2-yl-benzamide | m/z: 450 (M + 1)+; Rt = 2.56 min. |
| 3e | 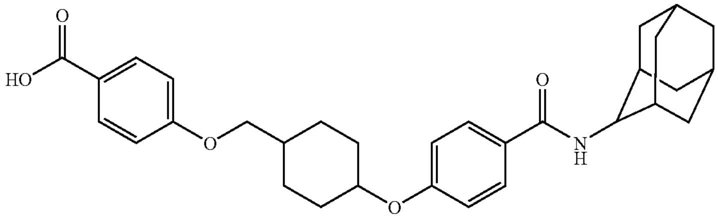 | 4-{4-[4-(Adamantan-2-yl-carbamoyl)-phenoxy]-cyclo-hexylmethoxy}-benzoic acid | m/z: 504 (M + 1)+; Rt = 2.50 min. |
| 4e | 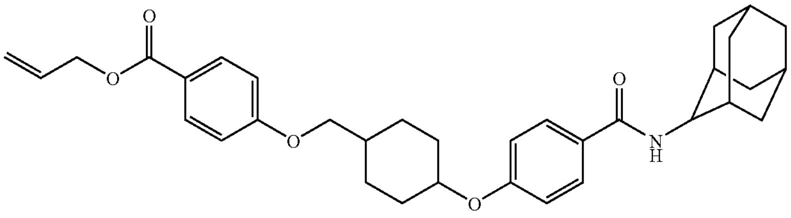 | 4-{4-[4-(Adamantan-2-yl-carbamoyl)-phenoxy]-cyclo-hexylmethoxy}-benzoic acid allyl ester | m/z: 544 (M + 1)+; Rt = 3.03 min. |

General Example F

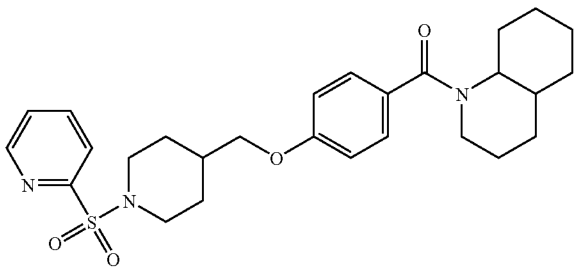

(Octahydro-quinolin-1-yl)-{4-[1-(pyridine-2-sulfonyl)-piperidin-4-ylmethoxy]-phenyl}-methanone 4-(4-Methoxycarbonyl-phenoxymethyl)-piperidine-1-carboxylic acid t-butyl ester To a stirred solution of N-Boc-4-piperidinemethanol (10 g, 46.45 mmol) in dry THF (500 mL) was added tributyl phosphine (18.77 g, 92.9 mmol) and 4-hydroxy benzoic acid methyl ester (10.6 g, 69.67 mmol). The reaction mixture was cooled to 0° C. and ADDP (23.41 g, 92.9 mmol) was added dropwise from an addition funnel over a period of 1 hr. The reaction was gradually brought to room temperature and stirring continued for 1 hr. The sol-vent was removed under vacuum and EtOAc (50 mL) was added and cooled to 0° C. The solid formed was filtered and the clear filtrate concentrated and purified by column chromatography (ISCO) using a step gradient starting with heptane going to EtOAc 100%. Desired fractions were collected and the solvent evaporated in vacuo affording 5.9 g (36%) of 4-(4-methoxycarbonyl-phenoxymethyl)-piperidine-1-carboxylic acid t-butyl ester as an oil.

$^1$H-NMR (400 MHz, $CDCl_3$) δ 1.28 (q, 2H), 1.39-1.54 (m, 9H), 1.81 (d, 2H), 1.97 (br.s., 1H), 3.79-3.94 (m, 6H), 4.17 (d, 2H), 6.89 (d, 2H), 7.99 (d, 2H).

4-(Piperidin-4-ylmethoxy)-benzoic acid methyl ester

To a solution of 4-(4-methoxycarbonyl-phenoxymethyl)-piperidine-1-carboxylic acid t-butyl ester (8.5 g, 24.61 mmol) in DCM (150 mL) was added TFA (45 mL) and the mixture was stirred for 2 hrs at room temperature. The volatiles were evaporated in vacuo and the residue crystallised from addition of diethyl ether. The solid was filtered off washed with a small portion of diethyl ether and dried. This afforded 8.8 g (99%) of 4-(piperidin-4-ylmeth-oxy)-benzoic acid methyl ester as a TFA salt.

$^1$H-NMR (400 MHz, $CDCl_3$) δ 1.75 (q, 2H), 1.98-2.21 (m, 3H), 2.95 (q, 2H), 3.42-3.56 (m, 3H), 3.84-3.98 (m, 4H), 6.90 (d, 2H), 7.98 (d, 2H), 9.19 (br.s., 1H), 9.72 (br.s., 1H).

m/z: 250 (M+1)+;

4-[1-(Pyridine-2-sulfonyl)-piperidin-4-ylmethoxy]-benzoic acid

To a suspension of 4-(piperidin-4-ylmethoxy)-benzoic acid methyl ester, TFA salt (1.6 g, 4.403 mmol) in DCM was added DIPEA (2.3 mL, 13.21 mmol) followed by 2-pyridinesulfonyl chloride HCl salt (1.89 g, 8.81 mmol). The resulting mixture was stirred for 16 hrs at room temperature and washed with 5% aqous citric acid. The organisk phase was dried ($MgSO_4$), filtered and the volatiles evaporated in vacuo. The crude ester was hydrolysed directly in the next step without further purification.

The crude ester was dissolved in a mixture of MeOH (100 mL) and THF (50 mL) and to this mixture was added 1 N NaOH (20 mL) followed by stirring for 16 hrs. at room temperature. The volume was reduced to ¼ and 1N HCl was added to pH ~1. The organic phase was separated and the aqueous phase extracted with DCM (2×50 mL). The combined organic phases were washed with water, dried ($MgSO_4$), filtered and the solvent evaporated in vacuo. The solid residue was washed in a mixture of water and diethyl ether, filtered and dried which afforded 1.45 g (87%) of 4-[1-(pyridine-2-sulfonyl)-piperidin-4-ylmethoxy]-benzoic acid as a solid.

$^1$H-NMR (400 MHz, $CDCl_3$) δ 1.39-1.61 (m, 2H), 1.90 (d, 3H), 2.78 (t, 2H), 3.87 (d, 2H), 4.04 (d, 2H), 6.90 (d, 2H), 7.45-7.57 (m, 1H), 7.87-8.00 (m, 2H), 8.05 (d, 2H), 8.74 (d, 1H).

m/z: 378 (M+1)+;

To a solution of 4-[1-(pyridine-2-sulfonyl)-piperidin-4-ylmethoxy]-benzoic acid (113 mg) in DMF (1.5 mL) was added HOBt (69 mg) and EDAC (58 mg) and the resulting mixture was stirred for 1 hr. cis-trans-Decahydroquinoline (42 mg) was added and stirring was continued for 16 hrs at ambient temperature. The crude reaction mixture was purified on a prep LC/MS and desired fractions were collected and the solvent evaporated in vacuo affording 132 mg (88%) of the title compound as an oil.

$^1$H-NMR (400 MHz, $CDCl_3$) δ 1.00-1.17 (m, 1H), 1.24-1.99 (m, 14H), 2.28 (d, 1H), 2.77 (t, 2H), 3.07 (br.s., 1H), 3.27-3.44 (m, 1H), 3.54 (br.s., 1H), 3.77-3.86 (m, 2H), 4.02 (d, 2H), 4.52 (br.s., 1H), 4.73 (br.s., 1H), 6.77-6.93 (m, 2H), 7.28-7.37 (m, 2H), 7.45-7.55 (m, 1H), 7.86-8.05 (m, 2H), 8.73 (d, 1H).

m/z: 499 (M+1)+;

In a similar way as described in general example F above the following compounds 1f-9f were made.

| Ex no | Molecule | IUPAC | LC-MS (electrospray) |
|---|---|---|---|
| 1f | 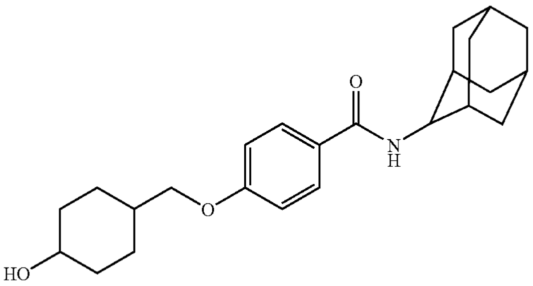 | 4-(4-Hydroxy-cyclohexyl-methoxy)-N-adamantan-2-yl-benzamide | m/z: 384 (M + 1)+; Rt = 2.14 min. |
| 2f | 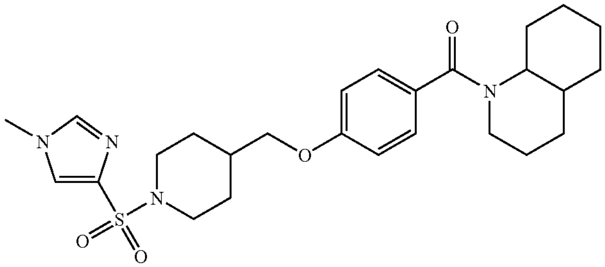 | {4-[1-(1-Methyl-1H-imidazole-4-sulfonyl)-piperidin-4-yl-methoxy]-phenyl}-(octahydro-quinolin-1-yl)-methanone | m/z: 501 (M + 1)+; Rt = 1.94 min. |
| 3f | 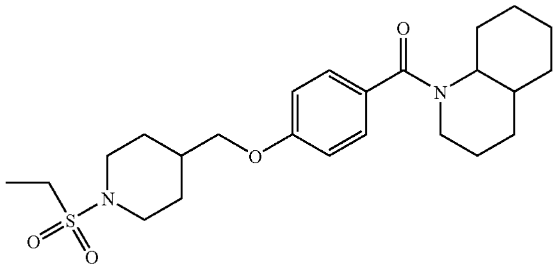 | [4-(1-Ethanesulfonyl-piperidin-4-yl-methoxy)-phenyl]-(octahydro-quinolin-1-yl)-methanone | m/z: 449 (M + 1)+; Rt = 2.14 min. |
| 4f | 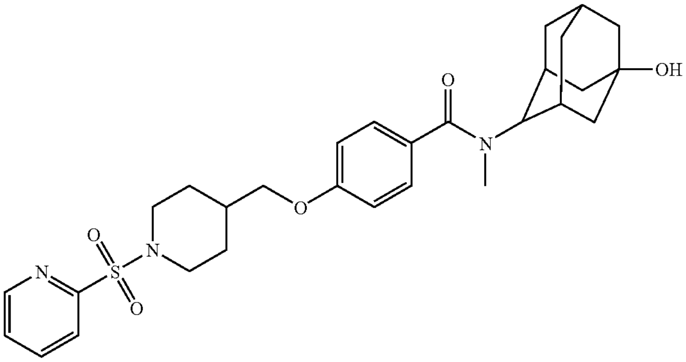 | N-(5-Hydroxy-adamantan-2-yl)-N-methyl-4-[1-(pyridine-2-sulfonyl)-piperidin-4-yl-methoxy]-benzamide | $^1$H-NMR (400 MHz, $CDCl_3$) δ 1.39-2.04(m, 13H), 2.21(d, 1H), 2.56 (d, 2H), 2.77(t, 2H), 3.14(d, 3H), 3.77-3.90 (m, 2H), 4.02(d, 2H), 4.20(d, 1H), 5.63(br.s., 1H), 6.81-6.93(m, 2H), 7.39(d, 2H), 7.51(t, 1H), 7.88-8.07(m, 2H), 8.75(d, 1H) |
| 5f | 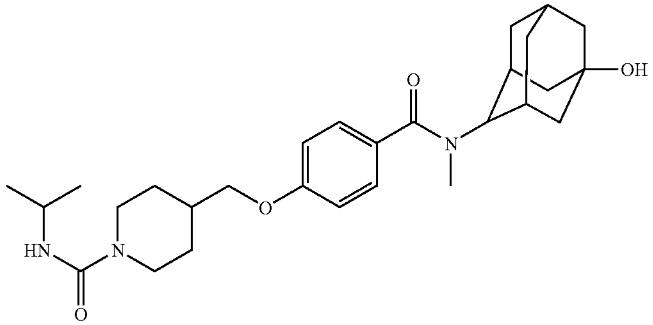 | 4-{4-[(5-Hydroxy-adamantan-2-yl)-methyl-carbamoyl]-phenoxy-methyl}-piperidine-1-carboxylic acid isopropyl-amide | $^1$H-NMR (400 MHz, $CDCl_3$) δ 1.15(d, 6H), 1.26-1.39(m, 2H), 1.52-2.04(m, 14H), 2.20(d, 1H), 2.55(d, 2H), 2.83(t, 2H), 3.13 (d, 3H), 3.83(d, 2H), 3.91-4.04(m, 3H), 4.08-4.23(m, 1H), 6.03(br.s., 1H), 6.88(d, 2H), 7.39(d, 2H) |

-continued

| Ex no | Molecule | IUPAC | LC-MS (electrospray) |
|---|---|---|---|
| 6f | 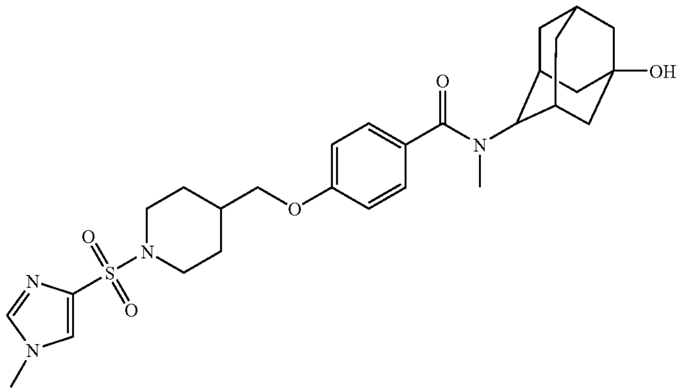 | N-(5-Hydroxy-adamantan-2-yl)-N-methyl-4-[1-(1-methyl-1H-imidazole-4-sulfonyl)-piperidin-4-ylmethoxy]-benzamide | $^1$H-NMR (400 MHz, $CDCl_3$) δ 1.41-1.62(m, 3H), 1.62-2.04(m, 13H), 2.20(d, 1H), 2.48-2.69(m, 3H), 3.11(d, 3H), 3.77(s, 3H), 3.82 (d, 2H), 3.90(d, 2H), 4.15(d, 1H), 4.90(br.s., 1H), 6.86(d, 2H), 7.39 (d, 2H), 7.45(s, 1H), 7.61(s, 1H) |
| 7f | 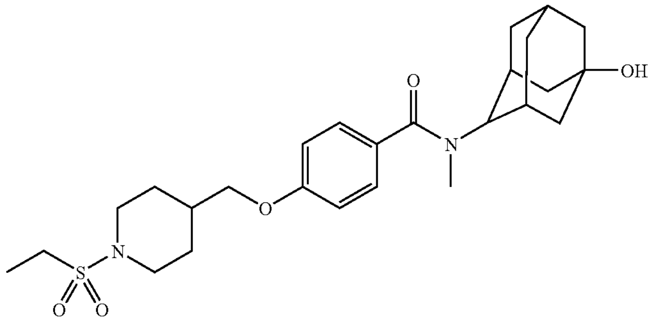 | 4-(1-Ethanesulfonyl-piperidin-4-ylmethoxy)-N-(5-hydroxy-adamantan-2-yl)-N-methyl-benzamide | $^1$H-NMR (400 MHz, $CDCl_3$) δ 1.37(t, 3H), 1.40-2.03(m, 15H), 2.20(d, 1H), 2.56(d, 2H), 2.83(t, 2H), 2.91-3.07(m, 4H), 3.12(d, 2H), 3.80-3.96(m, 4H), 4.15(d, 1H), 6.88(d, 2H), 7.41(d, 2H) |
| 8f | 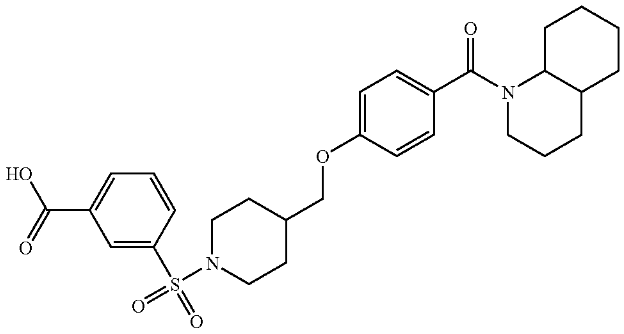 | 3-{4-[4-(Octahydro-quinoline-1-carbonyl)-phenoxymethyl]-piperidine-1-sulfonyl}-benzoic acid | m/z: 542 (M + 1)+ |
| 9f | 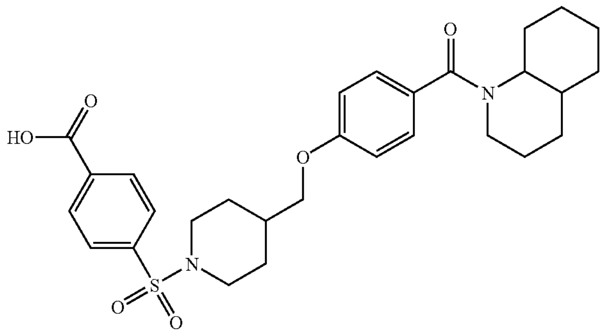 | 4-{4-[4-(Octahydro-quinoline-1-carbonyl)-phenoxymethyl]-piperidine-1-sulfonyl}-benzoic acid | $^1$H-NMR (400 MHz, $CDCl_3$) δ 1.05(br.s., 1H), 1.22-2.00(m, 15H), 2.34(t, 2H), 2.84 (t, 1H), 3.08(t, 1H), 3.63 (dd, 1H), 3.75-3.83(m, 2H), 3.89(d, 2H), 4.67 (d, 1H), 5.23(br.s., 1H), 6.83(d, 2H), 7.33(d, 2H), 7.85(d, 2H), 8.23 (d, 2H) |

General Example G

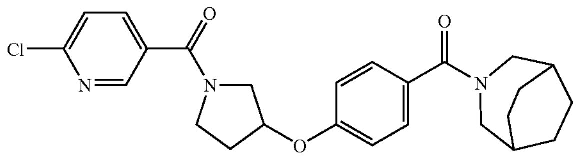

{3-[4-(3-Aza-bicyclo[3.2.2]nonane-3-carbonyl)-phenoxy]-pyrrolidin-1-yl}-(6-chloro-pyridin-3-yl)-methanone 3-(4-Carboxy-phenoxy)-pyrrolidine-1-carboxylic acid t-butyl ester To a stirred solution of 3-hydroxy-pyrrolidine-1-carboxylic acid t-butyl ester (3 g, 16.02 mmol) in dry THF (75 mL) was added triphenyl phosphine (4.62 g, 17.62 mmol) and 4-hydroxy-benzoic acid benzyl ester (4.02 g, 17.62 mmol). The reaction mixture was cooled to 0° C. and DEAD (2.78 mL, 17.62 mmol) was added dropwise over a period of 30 min. The reaction was gradually brought to room temperature and stirring continued for 16 hrs. The solvent was removed under vacuum and the residue purified by column chromatography (Flash 40) using a gradient of starting from EtOAc-heptane 1:20 to 1:5. Desired fractions were collected and the solvent evaporated in vacuo. The residue was dissolved in EtOH (80 mL) and 10% Pd/C (0.5 g) was added and the mixture was hydrogenated for 16 hrs. The mixture was filtered and the volatiles were evaporated in vacuo affording 3.4 g (69%) of 3-(4-carboxy-phenoxy)-pyrrolidine-1-carboxylic acid t-butyl ester as a solid.

$^1$H-NMR (400 MHz, DMSO-$d_6$) δ 1.40 (d, 9H), 2.05 (br.s., 1H), 2.17 (br.s., 1H), 3.23-3.50 (m, 3H) 3.51-3.66 (m, 1H), 5.11 (br.s., 1H), 6.81 (d, 1H), 7.03 (d, 1H), 7.78 (d, 1H), 7.90 (d, 1H), 10.30 (br.s., 1H).

(3-Aza-bicyclo[3.2.2]non-3-yl)-[4-(pyrrolidin-3-yloxy)-phenyl]-methanone

To a solution of 3-(4-carboxy-phenoxy)-pyrrolidine-1-carboxylic acid t-butyl ester (2.0 g, 6.53 mmol) in DMF (75 mL) was added HOBt (1.1 g, 7.83 mmol) and EDAC (1.5 g, 7.83 mmol) and the resulting mixture was stirred for 10 min. 3-Aza-bicyclo-[3.2.2]nonane (1 g, 7.83 mmol) and DIPEA (1.4 mL) were added and stirring was continued for 16 hrs at ambient temperature. The volatiles were evaporated in vacuo and to the residue was added water (50 mL) and diethyl ether (25 mL). A precipitate was forme, filtered off and redissolved in DCM (25 mL) followed by addition of TFA (10 mL). The mixture was stirred at room temperature for 16 hrs and the volatiles evaporated in vacuo. The residue was dissolved in water (50 mL) and washed with diethyl ether (2×10 mL). The pH of the aqueous phase was adjusted to ~11 by addition of 32% NaOH followed by extraction with diethyl ether (2×50 mL). The combined organic phases were dried ($Na_2SO_4$), filtered and evaporated in vacuo. The crude residue was stirred with EtOAc (20 mL) and the precipitate formed was filtered off. The filtrate was evaporated to dryness affording crude 1.1 g (55%) of (3-aza-bicyclo[3.2.2]non-3-yl)-[4-(pyrrolidin-3-yloxy)-phenyl]-methanone which was used without further purification.

m/z: 315 (M+1)+;

To a solution of (3-aza-bicyclo[3.2.2]non-3-yl)-[4-(pyrrolidin-3-yloxy)-phenyl]-methanone (150 mg, 0.48 mmol) in DCM (20 mL) was added TEA (130 μL) followed by 6-chloro-nicotinoyl chloride (126 mg, 0.72 mmol). The mixture was stirred at room temperature for 16 hrs followed by evaporation of the solvent in vacuo. The residue was purified on prep. HPLC affording after drying at 50° C. 115 mg (53%) of the title compound.

$^1$H-NMR (400 MHz, $CDCl_3$) δ 1.67 (br.s., 7H), 1.92 (br.s., 1H), 2.08-2.29 (m, 2H), 2.28-2.42 (m, 1H), 3.42-3.75 (m, 4H), 3.75-4.04 (m, 4H), 5.02 (d, 1H), 6.82 (d, 1H), 6.92 (d, 1H), 7.30-7.48 (m, 3H), 7.81-7.97 (m, 1H), 8.60 (dd, 1H).

m/z: 455 (M+1)+;

In a similar way as described in general example G above the following compounds 1 g-3 g were made.

| Ex no | Molecule | IUPAC | LC-MS (electrospray) |
|---|---|---|---|
| 1g | 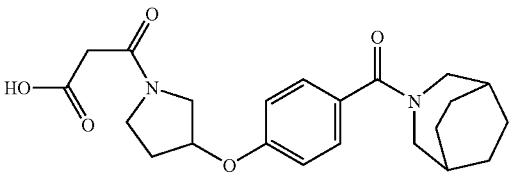 | 3-{3-[4-(3-Aza-bicyclo-[3.2.2]nonane-3-carbonyl)-phenoxy]-pyrrolidin-1-yl}-3-oxo-propionic acid | m/z: 401 (M + 1)+; Rt = 1.49 min. |
| 2g | 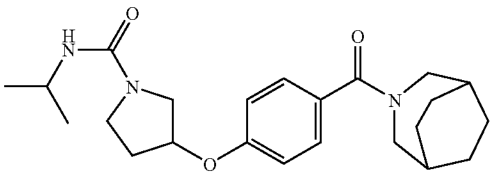 | 3-[4-(3-Aza-bicyclo[3.2.2]-nonane-3-carbonyl)-phenoxy]-pyrrolidine-1-carboxylic acid isopropyl-amide | m/z: 400 (M + 1)+; Rt = 1.72 min. |

-continued

| Ex no | Molecule | IUPAC | LC-MS (electrospray) |
|---|---|---|---|
| 3g | 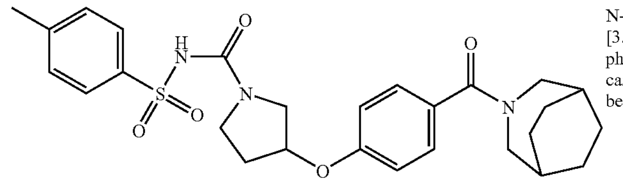 | N-{3-[4-(3-Aza-bicyclo-[3.2.2]nonane-3-carbonyl)-phenoxy]-pyrrolidine-1-carbonyl}-4-methyl-benzenesulfonamide | m/z: 512 (M + 1)+; Rt = 1.90 min. |

General Example H

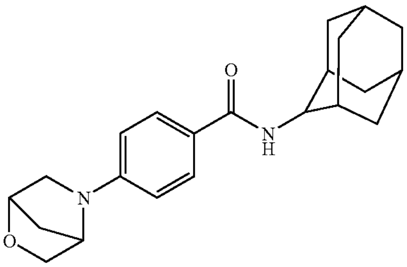

4-(2-Oxa-5-aza-bicyclo[2.2.1]hept-5-yl)-N-adamantan-2-yl-benzamide

4-Fluoro-N-adamantan-2-yl-benzamide

To a solution of 4-fluorobenzoic acid (15.0 g, 0.11 mol) in DMF (400 mL) was added HOBt (24.59 g, 0.16 mol) and EDAC (20.53 g, 0.11 mol). The resulting mixture was stirred for 1 hr at room temperature at which time a solution of 2-amino-adamantane.HCl (20.1 g, 0.11 mol) and DIPEA (20.52 mL) in DMF (100 mL) was added dropwise. The mixture was stirred at room temperature for 16 hrs and the volatiles evaporated in vacuo. The residue was dissolved in AcOEt and washed with aq. NaHCO3, brine, dried (MgSO4), filtered and the solvent evaporated in vacuo affording 28.66 g, (98%) of 4-fluoro-N-adamantan-2-yl-benzamide as a solid.

1H-NMR (300 MHz, $CDCl_3$) δ ppm 1.64-2.00 (m, 12H), 2.04 (br.s., 2H), 4.18-4.32 (m, 1H), 6.38 (d, 1H), 7.11 (t, 2H), 7.78 (dd, 2H).

m/z: 274.1 $(M+H)^+$

A solution of 4-fluoro-N-adamantan-2-yl-benzamide (0.5 g, 1.83 mmol), 2-oxa-5-aza-bicyclo[2.2.1]heptane (0.47 g, 2.01 mmol) and K2CO3 (0.5 g, 3.84 mmol) in NMP (3 mL) was heated in a microwave oven for 3 hrs. at 200° C. The cooled reaction mixture was added water (30 mL) and extracted with AcOEt (2×30 mL). The volatiles were evaporated in vacuo and the residue purified on column chromathrography (Flash 40) using first AcOEt-Heptan 1:4 followed by AcOEt-Heptan 1:1 as eluents. Pure fractions were collected and the solvent evaporated in vacuo. The solid residue was trituated with diethyl ether and filtered off affording after drying in vacuo at 50° C. 260 mg (46%) of the title compound as a solid.

1H-NMR (400 MHz, $CDCl_3$) 8 ppm 1.58-1.67 (m, 2H), 1.71 (br.s., 2H), 1.74-1.88 (m, 9H), 1.89-2.00 (m, 5H), 3.16 (d, 1H), 3.50 (dd, 1H), 4.13-4.22 (m, 1H), 4.41 (s, 1H), 4.62 (s, 1H), 6.24 (d, 1H), 6.50 (dd, 2H), 7.61 (d, 2H).

m/z: 353 $(M+1)^+$

In a similar way as described in general example H above the following compounds 1 g-3 g were made.

| Ex no | Molecule | IUPAC | LC-MS (elctrospray) |
|---|---|---|---|
| 1h | 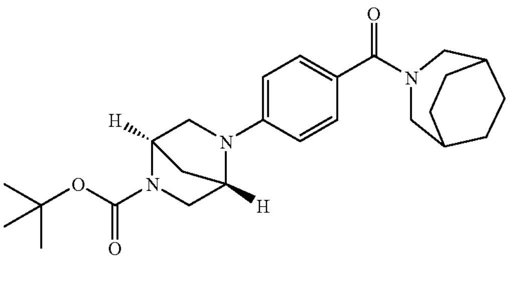 | (1S,4S)-5-[4-(3-Aza-bicyclo[3.2.2]nonane-3-carbonyl)-phenyl]-2,5-diaza-bicyclo[2.2.1]heptane-2-carboxylic acid tert-butyl ester | m/z: 426 (M + 1)+ |
| 2h | 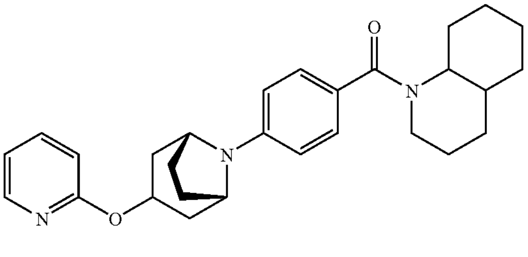 | (Octahydro-quinolin-1-yl)-{4-[(1S,5R)-3-(pyridin-2-yloxy)-8-aza-bicyclo[3.2.1]oct-8-yl]-phenyl}-methanone | m/z: 446 (M + 1)+ |

-continued

| Ex no | Molecule | IUPAC | LC-MS (elctrospray) |
|---|---|---|---|
| 3h | 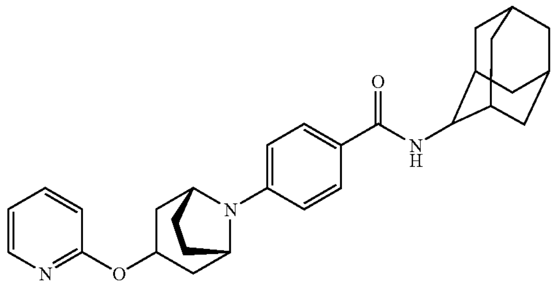 | 4-[(1S,5R)-3-(Pyridin-2-yloxy)-8-aza-bicyclo[3.2.1]oct-8-yl]-N-adamantan-2-yl-benzamide | m/z: 458 (M + 1)+ |

Pharmacological Methods

11βHSD1 Enzyme Assay

Materials $^3$H-cortisone and anti-rabbit Ig coated scintillation proximity assay (SPA) beads were purchased from Amersham Pharmacia Biotech, β-NADPH was from Sigma and rabbit anti-cortisol antibodies were from Fitzgerald. An extract of yeast transformed with h-11βHSD1 (Hult et al., *FEBS Lett,* 441, 25 (1998)) was used as the source of enzyme. The test compounds were dissolved in DMSO (10 mM). All dilutions were performed in a buffer containing 50 mM TRIS-HCl (Sigma Chemical Co), 4 mM EDTA (Sigma Chemical Co), 0.1% BSA (Sigma Chemical Co), 0.01% Tween-20 (Sigma Chemical Co) and 0.005% bacitracin (Novo Nordisk A/S), pH=7.4. Optiplate 96 wells plates were supplied by Packard. The amount of $^3$H-cortisol bound to the SPA beads was measured on TopCount NXT, Packard.

Methods h-11βHSD1, 120 nM $^3$H-cortisone, 4 mM β-NADPH, antibody (1:200), serial dilutions of test compound and SPA particles (2 mg/well) were added to the wells. The reaction was initiated by mixing the different components and was allowed to proceed under shaking for 60 min at 30° C. The reaction was stopped be the addition of 10 fold excess of a stopping buffer containing 500 μM carbenoxolone and 1 μM cortisone. Data was analysed using GraphPad Prism software.

TABLE 1

Inhibition of 11βHSD1 by compounds of the invention

| Example No. | h-11βHSD1 $IC_{50}$ values (nM) |
|---|---|
| A | 360 |
| B | 1350 |
| C | 1070 |
| E | 295 |
| F | 134 |
| G | 1178 |
| H | 43 |
| 1a | 130 |
| 2a | 1450 |
| 3a | 405 |
| 4a | 678 |
| 5a | 588 |
| 6a | 1200 |
| 7a | 1403 |
| 8a | 604 |
| 12a | 111 |

TABLE 1-continued

Inhibition of 11βHSD1 by compounds of the invention

| Example No. | h-11βHSD1 $IC_{50}$ values (nM) |
|---|---|
| 13a | 73 |
| 1b | 205 |
| 2b | 284 |
| 3b | 1398 |
| 4b | 2307 |
| 5b | 1298 |
| 2c | 118 |
| 3c | 96 |
| 4c | 51 |
| 5c | 158 |
| 6c | 120 |
| 7c | 1120 |
| 8c | 1652 |
| 11c | 421 |
| 1d | 75 |
| 2d | 180 |
| 1e | 190 |
| 2e | 190 |
| 3e | 300 |
| 4e | 482 |
| 1f | 465 |
| 2f | 134 |
| 3f | 271 |
| 4f | 1361 |
| 5f | 1800 |
| 6f | 2271 |
| 7f | 2185 |
| 8f | 266 |
| 9f | 163 |
| 3g | 2816 |
| 1h | 389 |
| 2h | 359 |
| 3h | 976 |

While the invention has been described and illustrated with reference to certain preferred embodiments thereof, those skilled in the art will appreciate that various changes, modifications, and substitutions can be made therein without departing from the spirit and scope of the present invention. For example, effective dosages other than the preferred dosages as set forth herein may be applicable as a consequence of variations in the responsiveness of the mammal being treated for the disease(s). Likewise, the specific pharmacological responses observed may vary according to and depending on the particular active compound selected or whether there are present pharmaceutical carriers, as well as the type of formulation and mode of administration employed, and such expected variations or differences in the results are contemplated in accordance with the objects and practices of the present invention. Accordingly, the invention is not to be limited as by the appended claims.

The features disclosed in the foregoing description and/or in the claims may both separately and in any combination thereof be material for realising the invention in diverse forms thereof.

Preferred features of the invention:

1. A compound of the general formula (I):

(I)

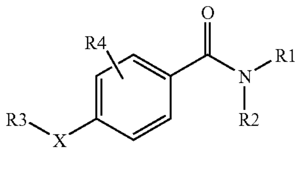

wherein $R^1$ and $R^2$ together with the nitrogen to which they are attached, are forming a 8-11 membered saturated or partially saturated bicyclic or tricyclic ring consisting of the shown nitrogen, 5-10 carbon atoms and from 0 to 1 additional heteroatoms selected from nitrogen, oxygen, and $S(O)_m$, where m is 0, 1 or 2, and said ring being substituted with 0 to 3 groups independently selected from $C_1$-$C_4$alkyl, halogen, hydroxy, oxo, COOH, —$NHR^{17}$, $NR^{17}R^{17}$, $C_1$-$C_4$alkyloxy, $C_1$-$C_4$alkyloxy$C_1$-$C_4$alkyl and $C_1$-$C_4$alkylcarbonyl, wherein each alkyl group is substituted with 0 to 1 $R^{21}$, or $R^1$ is hydrogen, $C_1$-$C_4$alkyl or cyclopropyl and $R^2$ is a substituted or unsubstituted adamantyl;

$R^{21}$ is halogen, hydroxy, oxo or COOH;

$R^4$ is selected from hydrogen, $C_1$-$C_4$alkyl, trifluoromethyl, halogen, $C_1$-$C_4$alkyloxy, $C_1$-$C_4$alkyloxy$C_1$-$C_4$alkyl and $C_1$-$C_4$alkylcarbonyl, wherein each alkyl group is substituted with 0 to 1 $R^{21}$;

X is selected from —O—, —S—, —$CR^5R^6$—, —NH—, and —$NR^6$—;

$R^5$ is hydrogen or fluorine;

$R^6$ is hydrogen, methyl, ethyl, iso-propyl or cyclo-propyl;

$R^3$ is selected from -1,4-cyclohexyl-$R^7$, —$CH_2$-1,4-cyclohexyl-$R^8$, -1,3-cyclohexyl-$R^9$, —$CH_2$-1,3-cyclohexyl-$R^{10}$, -4-piperidin-1-yl-$R^{11}$, —$CH_2$-4-piperidin-1-yl-$R^{12}$, -3-piperidin-1-yl-$R^{13}$, —$CH_2$-3-piperidin-1-yl-$R^{14}$, -4-bicyclo[2.2.2]octan-1-yl-$R^{15}$ and —$CH_2$-4-bicyclo[2.2.2]octan-1-yl-$R^{16}$;

$R^7$, $R^8$, $R^9$, $R^{10}$, $R^{15}$ and $R^{16}$ are independently selected from $CO_2H$, $C(O)R^{19}$, OH, —$(CR^{22}$—$R^{23})_n$—C(O)—$NR^{17}R^{18}$, —$(CR^{22}R^{23})_n$—$NHC(O)R^{18}$, —$(CR^{22}R^{23})_n$—$OR^{18}$, —$(CR^{22}R^{23})_n$—$SR^{18}$, —$(CR^{22}$—$R^{23})_n$—$S(O)_2R^{18}$, —$(CR^{22}R^{23})_n$—$S(O)_2NR^{17}R^{18}$, —$(CR^{22}R^{23})_n$—$NR^{17}R^{18}$, —$(CR^{22}R^{23})$, —$NR^{17}C(O)$—$NR^{17}R^{18}$, —$(CR^{22}R^{23})_n$—C═C—$R^{18}$, —$(CR^{22}R^{23})_n$—C≡C—$R^{18}$, —$(CR^{22}R^{23})_n$-aryl substituted with 0 to 2 $R^{20}$, and —$(CR^{22}R^{23})_n$-hetaryl substituted with 0 to 2 $R^{20}$;

n is 0, 1 or 2;

each $R^{22}$ and $R^{23}$ are independently selected from hydrogen, halogen, $C_1$-$C_6$alkyl and cycloalkyl, each of which $C_1$-$C_6$alkyl and cycloalkyl may be substituted with 0 to 2 halogen, hydroxy or oxo and the carbon in $CR^{22}R^{23}$ can together with the $R^{22}$ and/or $R^{23}$ groups be part of a cycloalkyl ring;

$R^{20}$ is selected from halogen, hydroxy, oxo, —COOH, —$S(O)_{0\text{-}2}R^{19}$, —$S(O)_{0\text{-}2}NR^{19}R^{19}$, cyclopropyl, —O—$R^{19}$, $C_1$-$C_6$alkyl, aryl, hetaryl, $NR^{19}CONR^{19}R^{19}$; $NR^{19}SO_2NR^{19}R^{19}$ or $NCONHSO_2R^{19}$;

$R^{17}$ is selected from hydrogen or selected from $C_1$-$C_6$alkyl, $C_1$-$C_6$alkenyl, $C_1$-$C_6$alkynyl, cycloalkyl, aryl or hetaryl, each of which may be substituted with 0 to 2 $R^{20}$;

$R^{18}$ is selected from $C_1$-$C_6$alkyl, $C_1$-$C_6$alkenyl, $C_1$-$C_6$alkynyl, cycloalkyl, aryl or hetaryl, each of which may be substituted with 0 to 2 $R^{20}$;

where $R^{17}$ and $R^{18}$ are optionally connected by a covalent bond so as to form a ring comprising the N to which $R^{17}$ and $R^{18}$ are connected;

$R^{19}$ is selected from hydrogen, hydroxy, $C_1$-$C_6$alkyl, $C_1$-$C_6$alkenyl, $C_1$-$C_6$alkynyl, cycloalkyl, $C_1$-$C_6$alkyloxy, aryl or hetaryl wherein hydroxy, $C_1$-$C_6$alkyl, cycloalkyl, $C_1$-$C_6$alkyloxy, aryl or hetaryl are optional substituted with $R^{20}$;

$R^{11}$, $R^{12}$, $R^{13}$ and $R^{14}$ are independently selected from —C(O)—$NR^{17}R^{18}$, —$CH_2C(O)$—$NR^{17}R^{18}$, —$C(O)R^{19}$, —$S(O)_2R^{18}$, —$S(O)_2NR^{17}R^{18}$, $C_1$-$C_6$alkyl substituted with 0 to 2 $R^{20}$, aryl substituted with 0 to 2 $R^{20}$, and hetaryl substituted with 0 to 2 $R^{20}$; or a salt thereof with a pharmaceutically acceptable acid or base, or any optical isomer or mixture of optical isomers, including a racemic mixture, or any tautomeric forms.

2. The compound according to clause 1, wherein n is 0.

3. The compound according to clause 1, wherein $R^{22}$ and $R^{23}$ are both hydrogen.

4. The compound according to clause 3, wherein n is 1.

5. The compound according to any of the preceding clauses, wherein $R^{17}$ and $R^{18}$ are connected by a covalent bond so as to form a piperidine, a piperazine, a substituted piperidine or a substituted piperazine.

6. The compound according to any of the preceding clauses, wherein $R^4$ is hydrogen.

7. The compound according to any of the preceding clauses, wherein $R^1$ and $R^2$ together with the nitrogen to which they are attached, are forming a 8-11 membered saturated or partially saturated bicyclic or tricyclic ring, said ring being selected from the group consisting of

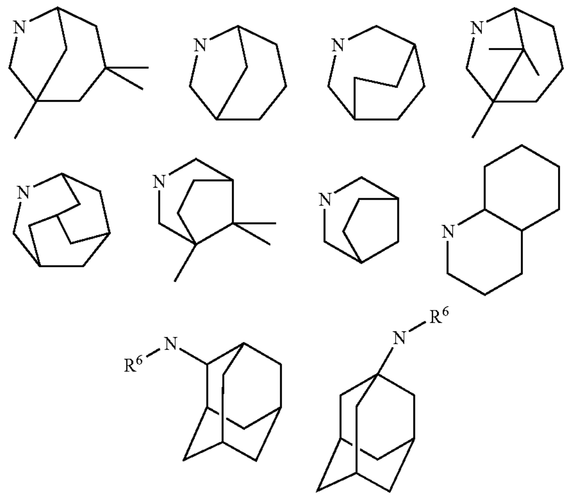

where each carbon is substituted with 0 to 2 $R^{25}$, and $R^{25}$ is independently selected from $C_1$-$C_8$alkyl, halogen, hydroxy, oxo, COOH, and $C_1$-$C_6$alkyloxy.

8. The compound according to clause 7, wherein $R^1$ and $R^2$ together with the nitrogen to which they are attached, are forming a 8-11 membered saturated or partially saturated bi-cyclic or tricyclic ring, said ring being selected from the group consisting of

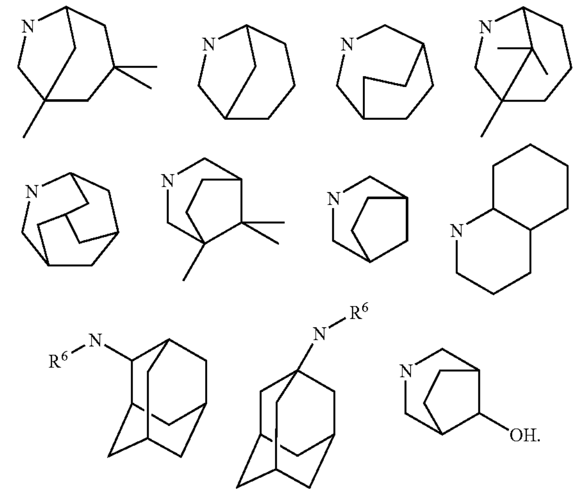

9. The compound according to any of the preceding clauses, wherein X is —O—.

10. The compound according to any of the preceding clauses, wherein $R^3$ is -1,4-cyclohexyl-$R^7$ or —$CH_2$-1,4-cyclohexyl-$R^8$.

11. The compound according to clause 10, wherein $R^7$ and $R^8$ are $C(O)R^{19}$.

12. The compound according to clause 11, wherein $R^{19}$ is hydroxy.

13. The compound according to clause 10, wherein $R^7$ and $R^8$ are selected from —$CH_2$—O-aryl, —$CH_2$—O-hetaryl, —O-aryl, —O-hetaryl, —$CH_2$—O—$C_{1-6}$alkyl, —NHC(O)$R^{18}$, where the aryl, hetaryl and $C_{1-6}$alkyl groups are optionally substituted.

14. The compound according to clause 10, wherein $R^7$ and $R^8$ are selected from —NH—$S(O)_r$ aryl, —NH—$S(O)_2$-hetaryl, —NH-aryl, —NH-hetaryl, —$S(O)_2$-aryl and —$S(O)_2$-hetaryl, where the aryl and hetaryl groups are optionally substituted.

15. The compound according to any of clauses 1-9, wherein $R^3$ is -1,3-cyclohexyl-$R^9$ or —$CH_2$-1,3-cyclohexyl-$R^{10}$.

16. The compound according to any of the preceding clauses, wherein $R^3$ comprises a cyclohexyl ring and $R^7$, $R^8$, $R^9$ or $R^{10}$ is attached in the cis-configuration.

17. The compound according to any of clauses 1-15, wherein $R^3$ comprises a cyclohexyl ring and $R^7$, $R^8$, $R^9$ or $R^{10}$ is attached in the trans-configuration.

18. The compound according to any of the clauses 1-9, wherein $R^3$ is -4-piperidin-1-yl-$R^{11}$ or —$CH_2$-4-piperidin-1-yl-$R^{12}$.

19. The compound according to clause 18, wherein $R^{11}$ and $R^{12}$ are selected from aryl, hetaryl, —$S(O)_2$-aryl and —$S(O)_2$-hetaryl, where each aryl and hetaryl groups are optionally substituted.

20. The compound according to any of the clauses 1-9, wherein $R^3$ is -3-piperidin-1-yl-$R^{13}$ or —$CH_2$-3-piperidin-1-yl-$R^{14}$.

21. The compound according to any of clauses 1-6, wherein $R^1$ is hydrogen, $C_1$-$C_4$alkyl or cyclopropyl.

22. The compound according to clause 21, wherein $R^2$ is an unsubstituted adamantyl selected from 1-adamantyl and 2-adamantyl.

23. The compound according to clause 21, wherein $R^2$ is a substituted adamantyl.

24. The compound according to clause 23, wherein $R^2$ is a substituted 1-adamantyl or a substituted 2-adamantyl.

25. The compound according to any of clauses 23-24, wherein $R^2$ is an adamantyl substituted with one, two or more substituent independently selected from halogen, hydroxy, oxo, COOH, $C_1$-$C_6$alkyl and $C_1$-$C_6$alkyloxy.

26. The compound according to any of the preceding clauses, which is selected from the group consisting of

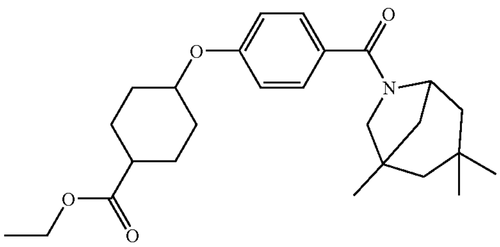

4-[4-(1,3,3-Trimethyl-6-aza-bicyclo[3.2.1]octane-6-carbonyl)-phenoxy]-cyclohexanecarboxylic acid ethyl ester,

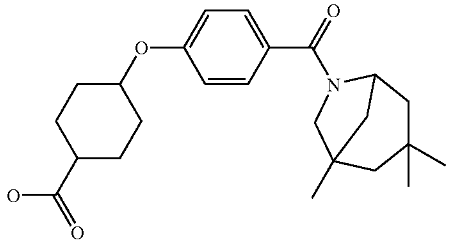

4-[4-(1,3,3-Trimethyl-6-aza-bicyclo[3.2.1]octane-6-carbonyl)-phenoxy]-cyclohexanecarboxylic acid,

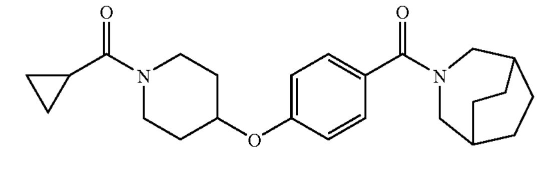

(3-Aza-bicyclo[3.2.2]non-3-yl)-[4-(1-cyclopropanecarbonyl-piperidin-4-yloxy)-phenyl]-methanone,

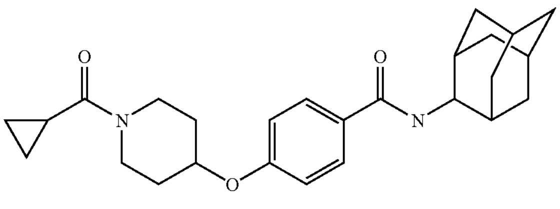

4-(1-Cyclopropanecarbonyl-piperidin-4-yloxy)-N-tricyclo[3.3.1.1.3.7]decan-2-yl-benzamide,

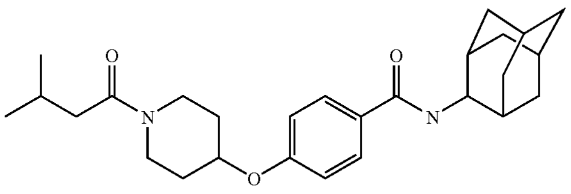

4-[1-(3-Methyl-butyryl)-piperidin-4-yloxy]-N-tricyclo[3.3.1.1.3.7]decan-2-yl-benzamide,

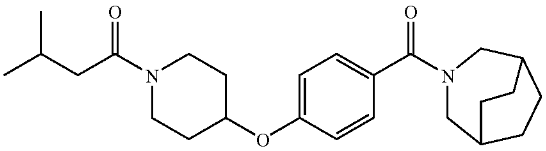

1-{4-[4-(3-Aza-bicyclo[3.2.2]nonane-3-carbonyl)phenoxy]-piperidin-1-yl}-3-methyl-butan-1-one,

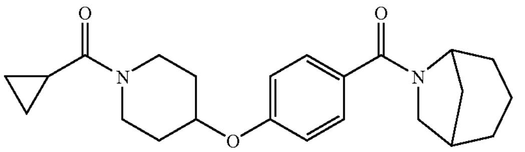

(6-Aza-bicyclo[3.2.1]oct-6-yl)-[4-(1-cyclopropanecarbonyl-piperidin-4-yloxy)-phenyl]-methanone,

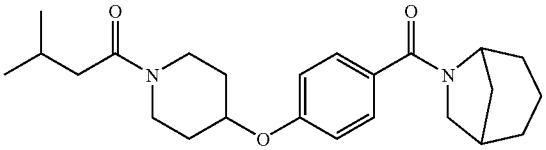

1-{4-[4-(6-Aza-bicyclo[3.2.1]octane-6-carbonyl)-phenoxy]-piperidin-1-yl}-3-methyl-butan-1-one,

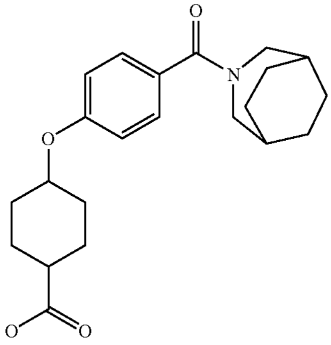

4-[4-(3-Aza-bicyclo[3.2.2]nonane-3-carbonyl)-phenoxy]-cyclohexanecarboxylic acid,

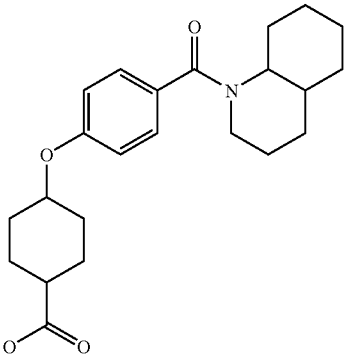

4-[4-(Octahydro-quinoline-1-carbonyl)-phenoxy]-cyclohexanecarboxylic acid,

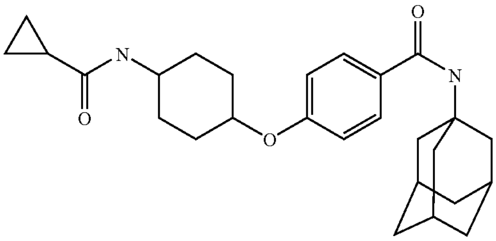

cis/trans-4-[4-(Cyclopropanecarbonyl-amino)-cyclohexyloxy]-N-tricyclo[3.3.1.1.3.7]decan-1-yl-benzamide,

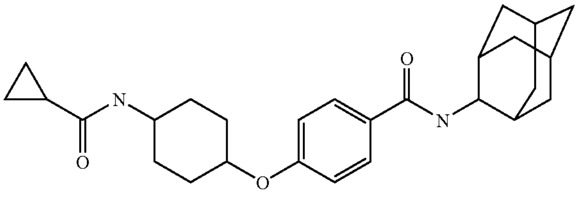

cis/trans-4-[4-(Cyclopropanecarbonyl-amino)-cyclohexyloxy]-N-tricyclo[3.3.1.1.3.7]decan-2-yl-benzamide,

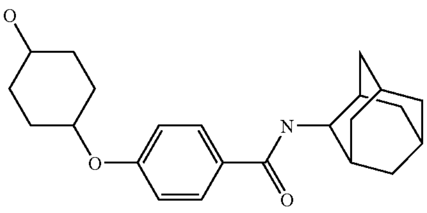

N-Adamantan-2-yl-4-(4-hydroxy-cyclohexyloxy)-benzamide,

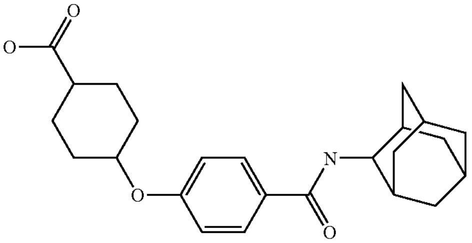

cis/trans 4-[4-(Tricyclo[3.3.1.1.3.7]decan-2-ylcarbamoyl)-phenoxy]-cyclohexanecarboxylic acid,

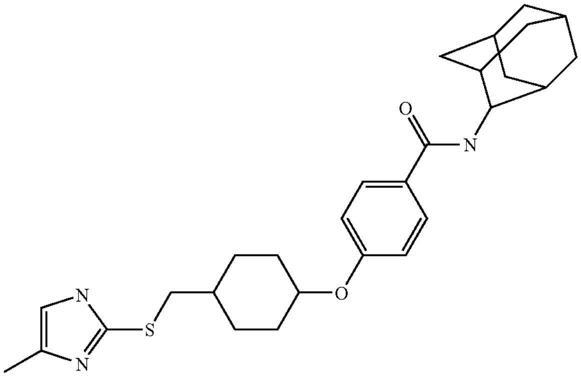

N-Adamantan-2-yl-4-[4-(4-methyl-1H-imidazol-2-ylsulfanylmethyl)-cyclohexyloxy]-benzamide,

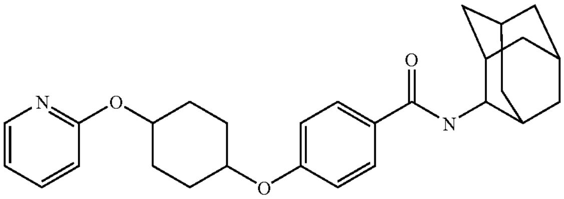

4-[4-(Pyridin-2-yloxy)-cyclohexyloxy]-N-tricyclo[3.3.1.1.3.7]decan-2-yl-benzamide,

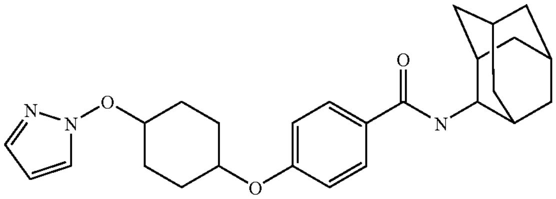

4-[4-(Pyrazol-1-yloxy)-cyclohexyloxy]-N-tricyclo[3.3.1.1.3.7]decan-2-yl-benzamide,

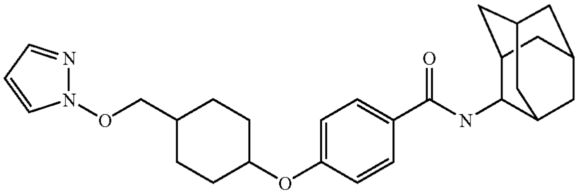

4-[4-(Pyrazol-1-yloxymethyl)-cyclohexyloxy]-N-tricyclo[3.3.1.1.3.7]decan-2-yl-benzamide,

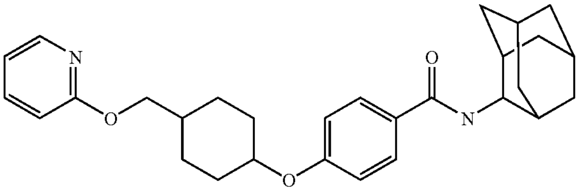

4-[4-(Pyridin-2-yloxymethyl)-cyclohexyloxy]-N-tricyclo[3.3.1.1.3.7]decan-2-yl-benzamide,

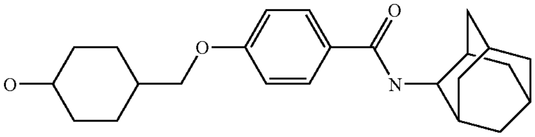

4-(4-Hydroxy-cyclohexylmethoxy)-N-tricyclo[3.3.1.1.3.7]decan-2-yl-benzamide,

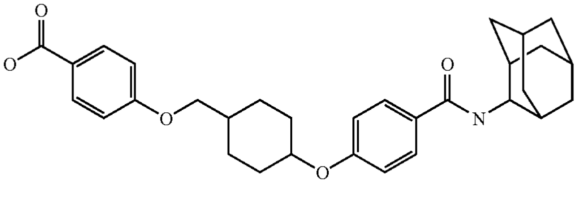

4-{4-[4-(Tricyclo[3.3.1.1.3.7]decan-2-ylcarbamoyl)-phenoxy]-cyclohexylmethoxy}-benzoic acid, and

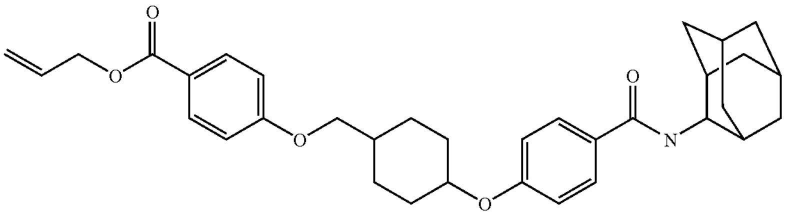

4-{4-[4-(Tricyclo[3.3.1.1.3.7]decan-2-ylcarbamoyl)-phenoxy]-cyclohexylmethoxy}-benzoic acid allyl ester, or a prodrug thereof, a salt thereof with a pharmaceutically acceptable acid or base, or any optical isomer or mixture of optical isomers, including a racemic mixture, or any tautomeric forms.

27. The compound according to any one of the preceding clauses, wherein polar surface area (PSA) of said compound is in the range from 40 Å$^2$ to 130 Å$^2$, preferably from 50 Å$^2$ to 130 Å$^2$, more preferably from 60 Å$^2$ to 120 Å$^2$, more preferably from 70 Å$^2$ to 120 Å$^2$, most preferable from 70 Å$^2$ to 110 Å$^2$.

28. The compound according to any one of the preceding clauses, wherein the molar weight of said compound is in the range from 350 D to 650 D, preferably from 400 D to 600 D.

29. The compound according to any one of the preceding clauses, which is an agent useful for the treatment, prevention and/or prophylaxis of any conditions, disorders and diseases wherein a modulation or an inhibition of the activity of 11βHSD1 is beneficial.

30. The compound according to any one of the clauses 1-28, which is an agent useful for the treatment, prevention and/or prophylaxis of any conditions, disorders and diseases that are influenced by intracellular glucocorticoid levels.

31. The compound according to any one of the clauses 1-28 which is an agent useful for the treatment, prevention and/or prophylaxis of conditions, disorders or diseases selected from the group consisting of the metabolic syndrome, insulin resistance, dyslipidemia, hypertension and obesity.

32. The compound according to any one of the clauses 1-28 which is an agent useful for the treatment, prevention and/or prophylaxis of type 2 diabetes, impaired glucose tolerance (IGT), impaired fasting glucose (IFG).

33. The compound according to any one of the clauses 1-28 which is an agent useful for the delaying or prevention of the progression from IGT into type 2 diabetes.

34. The compound according to any one of the clauses 1-28 which is an agent useful for delaying or prevention of the progression of the metabolic syndrome into type 2 diabetes.

35. The compound according to any one of the clauses 1-28 which is an agent useful for the treatment, prevention and/or prophylaxis of adverse effects of glucocorticoid receptor agonist treatment or therapy.

36. A pharmaceutical composition comprising, as an active ingredient, at least one compound according to any one of the clauses 1-28 together with one or more pharmaceutically acceptable carriers or excipients.

37. The pharmaceutical composition according to clause 36 which is for oral, nasal, buccal, transdermal, pulmonal or parenteral administration.

38. The pharmaceutical composition according to clause 36 or 37 in unit dosage form, comprising from 0.05 mg to 2000 mg/day, from 0.1 mg to 1000 mg or from 0.5 mg to 500 mg per day of the compound according to anyone of the clauses 1-28.

39. Use of a compound according to any of the clauses 1-28, for the preparation of a pharmaceutical composition for the treatment, prevention and/or prophylaxis of any conditions, disorders and diseases wherein a modulation or an inhibition of the activity of 11βHSD1 is beneficial.

40. Use of a compound according to any of the clauses 1-28, for the preparation of a pharmaceutical composition for the treatment, prevention and/or prophylaxis of any conditions, disorders and diseases that are influenced by intracellular glucocorticoid levels.

41. Use of a compound according to any of the clauses 1-28, for the preparation of a pharmaceutical composition for the treatment, prevention and/or prophylaxis of conditions, disorders or diseases selected from the group consisting of the metabolic syndrome, insulin resistance, dyslipidemia, hypertension and obesity.

42. Use of a compound according to any of the clauses 1-28, for the preparation of a pharmaceutical composition for the treatment, prevention and/or prophylaxis of type 2 diabetes, impaired glucose tolerance (IGT), impaired fasting glucose (IFG).

43. Use of a compound according to any of the clauses 1-28, for the preparation of a pharmaceutical composition for the delaying or prevention of the progression from IGT to type 2 diabetes.

44. Use of a compound according to any of the clauses 1-28, for the preparation of a pharmaceutical composition for the delaying or prevention of the progression of the metabolic syndrome into type 2 diabetes.

45. Use of a compound according to any of the clauses 1-28, for the preparation of a pharmaceutical composition for the treatment, prevention and/or prophylaxis of adverse effects of glucocorticoid receptor agonist treatment or therapy.

46. A method for the treatment, prevention and/or prophylaxis of any conditions, disorders or diseases wherein a modulation or an inhibition of the activity of 11βHSD1 is beneficial, the method comprising administering to a subject in need thereof an effective amount of a compound according to the invention.

47. The method according to clause 46 wherein the conditions, disorders or diseases are selected from the group consisting of the metabolic syndrome, insulin resistance, dyslipidemia, hypertension and obesity.

Other preferred features of the invention:

1. A compound of the general formula (I):

(I)

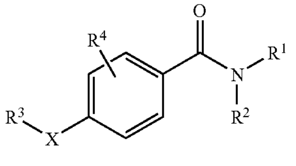

wherein $R^1$ and $R^2$ together with the nitrogen to which they are attached, are forming a 8-11 membered saturated or partially saturated bicyclic or tricyclic ring consisting of the shown nitrogen, 5-10 carbon atoms and from 0 to 1 additional heteroatom selected from nitrogen, oxygen, and $S(O)_m$, where m is 0, 1 or 2, and said ring being substituted with 0 to 3 groups independently selected from $C_1$-$C_4$alkyl, halogen, hydroxy, oxo, COOH, —$NHR^7$, $NR^7R^8$, —$S(O)_2C_1$-$C_4$alkyl, —$S(O)_2NR^7R^8$, $C_1$-$C_4$alkyloxy, $C_1$-$C_4$alkyloxy$C_1$-$C_4$alkyl and $C_1$-$C_4$alkylcarbonyl, wherein each alkyl group is substituted with 0 to 1 $R^{18}$, or $R^1$ is hydrogen, $C_1$-$C_4$alkyl or cyclopropyl and $R^2$ is adamantyl optionally substituted with 0 to 1 $R^{18}$;

$R^3$ is selected from -1,2-cyclopentyl-$R^9$, -1,3-cyclopentyl-$R^9$, -1,4-cyclohexyl-$R^9$, —$CH_2$-1,4-cyclohexyl-$R^9$, -1,3-cyclohexyl-$R^9$, —$CH_2$-1,3-cyclohexyl-$R^9$, -3-pyrrolidin-1-yl-$R^{10}$, —$CH_2$-3-pyrrolidin-1-$R^{10}$, 4-tetrahydro-pyran, 4-tetrahydro-pyran-2-yl-$R^9$, 4-tetrahydro-pyran-3-yl-$R^9$, -4-piperidin-1-yl-$R^{11}$, -3-piperidin-1-yl-$R^{11}$, —$CH_2$-3-piperidin-1-yl-$R^{11}$, -4-bicyclo[2.2.2]octan-1-yl-$R^{12}$ and —$CH_2$-4-bicyclo[2.2.2]octan-1-yl-$R^{12}$;

X is selected from —O—, —$S(O)_n$—, —$CR^5R^6$—, and —$NR^7$—; or $R^3$ and $R^7$ are connected by a covalent bond so as to form a bicyclic or tricyclic hetcycloalkyl ring comprising the N to which $R^3$ and $R^7$ are connected; the hetcycloalkyl ring may further be substituted with one or more $R^{19}$;

$R^4$ is selected from hydrogen, $C_1$-$C_4$alkyl, trifluoromethyl, halogen, $C_1$-$C_4$alkyloxy, $C_1$-$C_4$alkyloxy$C_1$-$C_4$alkyl and $C_1$-$C_4$alkylcarbonyl, wherein each alkyl group is substituted with 0 to 1 $R^{18}$;

$R^5$ and $R^6$ independently are selected from hydrogen, fluorine, methyl, ethyl, iso-propyl or cyclopropyl;

$R^7$ is selected from hydrogen or selected from $C_1$-$C_6$alkyl, $C_1$-$C_6$alkenyl, $C_1$-$C_6$alkynyl, cycloalkyl, aryl or hetaryl, each of which may be substituted with 0 to 2 $R^{19}$;

$R^8$ is selected from $C_1$-$C_6$alkyl, $C_1$-$C_6$alkenyl, $C_1$-$C_6$alkynyl, cycloalkyl, hetcycloalkyl, aryl or hetaryl, each of which may be substituted with 0 to 2 $R^{19}$; or $R^7$ and $R^8$ optionally are connected by a covalent bond so as to form a ring comprising the N to which $R^7$ and $R^8$ are connected; the ring may further be substituted with one or more $R^{19}$;

$R^9$ and $R^{12}$ independently are selected from hydroxy, cyano, $C(O)R^{13}$, —$(CR^{14}R^{15})_nC(O)NR^7R^8$, —$(CR^{14}R^{15})_nNHC(O)R^{16}$, —$(CR^{14}R^{15})_nOR^{16}$, —$(CR^{14}R^{15})_nS(O)_mR^{16}$, —$(CR^{14}R^{15})_nS(O)_2NR^7R^8$, —$(CR^{14}R^{15})_nNR^7R^8$, —$(CR^{14}R^{15})_nNR^{17}C(O)NR^7R^8$, —$(CR^{14}R^{15})_nNR^{17}S(O)_2R^{16}$, —$(CR^{14}R^{15})_nC{=}C$—$R^{16}$, —$(CR^{14}R^{15})_nC{\equiv}C$—$R^{16}$, —$(CR^{14}R^{15})_n$aryl substituted with 0 to 2 $R^{20}$, and —$(CR^{14}R^{15})_n$hetaryl optionally substituted with 0 to 2 $R^{19}$;

$R^{10}$ and $R^{11}$ independently are selected from —$C(O)NR^7R^8$, —$CH_2C(O)NR^7R^8$, —$C(O)R^{17}$, —$S(O)_2R^{16}$ or —$S(O)_2NR^7R^8$, wherein the alkyl, aryl and hetaryl groups are optionally substituted with 0 to 2 $R^{19}$;

m and n independently are 0, 1 or 2;

$R^{13}$ is selected from hydroxy, $C_1$-$C_6$alkyl, $C_1$-$C_6$alkenyl, $C_1$-$C_6$alkynyl, cycloalkyl, $C_1$-$C_6$alkyloxy, aryl, aryloxy, aryl$C_1$-$C_6$alkyloxy, hetaryl, hetaryloxy or hetaryl$C_1$-$C_6$alkyloxy wherein the $C_1$-$C_6$alkyl, cycloalkyl, aryl or hetaryl groups are optionally substituted with one or more $R^{19}$;

$R^{14}$ and $R^{15}$ independently are selected from hydrogen, halogen, $C_1$-$C_6$alkyl and cycloalkyl, each of which $C_1$-$C_6$alkyl and cycloalkyl may be substituted with 0 to 2 halogen, hydroxy or oxo and the carbon in $CR^{14}R^{15}$ can together with the $R^{14}$ and/or $R^{15}$ groups be part of a cycloalkyl ring;

$R^{16}$ is selected from hydrogen, $C_1$-$C_6$alkyl, $C_1$-$C_6$alkenyl, $C_1$-$C_6$alkynyl, cycloalkyl, hetcycloalkyl, aryl or hetaryl wherein the $C_1$-$C_6$alkyl, cycloalkyl, aryl or hetaryl groups are optionally substituted with one or more $R^{19}$;

$R^{17}$ is selected from hydrogen, $C_1$-$C_6$alkyl, $C_1$-$C_6$alkylC(O)$R^{20}$, —$(CR^{14}R^{15})_nNR^{17}S(O)_2R^{16}$, cycloalkyl, hetcycloalkyl, aryl or hetaryl, wherein the alkyl, cycloalkyl, hetcycloalkyl, aryl and hetaryl groups optionally are substituted with one or more $R^{21}$;

$R^{18}$ is halogen, hydroxy, oxo, —$S(O)_2C_1$-$C_4$alkyl, —$S(O)_2NR^7R^8$ or —$C(O)R^{13}$;

$R^{19}$ is selected from halogen, hydroxy, oxo, —$C(O)R^{20}$, $C_1$-$C_6$alkylC(O)$R^{20}$, —$S(O)_nR^{16}$, —$S(O)_nNR^7R^8$, cyclopropyl, —$OR^{16}$, $C_1$-$C_6$alkyl, aryl, hetaryl, —$NR^{22}C(O)NR^7R^8$, —$NR^{22}S(O)_2NR^7R^8$ or —$NC(O)NHS(O)_2R^{16}$;

$R^{20}$ is selected from hydroxy, $C_1$-$C_6$alkyl, $C_1$-$C_6$alkenyl, $C_1$-$C_6$alkynyl, cycloalkyl, $C_1$-$C_6$alkyloxy, aryl, aryloxy, aryl$C_1$-$C_6$alkyloxy, hetaryl, hetaryloxy or hetaryl$C_1$-$C_6$alkyloxy;

$R^{21}$ is halogen, cyano or hydroxy; or a salt thereof with a pharmaceutically acceptable acid or base, or any optical isomer or mixture of optical isomers, including a racemic mixture, or any tautomeric forms.

2. The compound according to clause 1, wherein n is 0.

3. The compound according to clause 1, wherein $R^{14}$ and $R^{15}$ are both hydrogen.

4. The compound according to clause 3, wherein n is 1.

5. The compound according to any of the preceding clauses, wherein $R^7$ and $R^8$ are connected by a covalent bond so as to form a pyrrolidine, a piperidine, a piperazine, a substituted pyrrolidine, a substituted piperidine or a substituted piperazine.

6. The compound according to any of the preceding clauses, wherein $R^7$ and $R^8$ are connected by a covalent bond so as to form a piperidine, a piperazine, a substituted piperidine or a substituted piperazine.

7. The compound according to any of the preceding clauses, wherein $R^4$ is hydrogen.

8. The compound according to any of the preceding clauses, wherein $R^1$ and $R^2$ together with the nitrogen to which they are attached, are forming a 8-11 membered saturated or partially saturated bicyclic or tricyclic ring, said ring being selected from the group consisting of

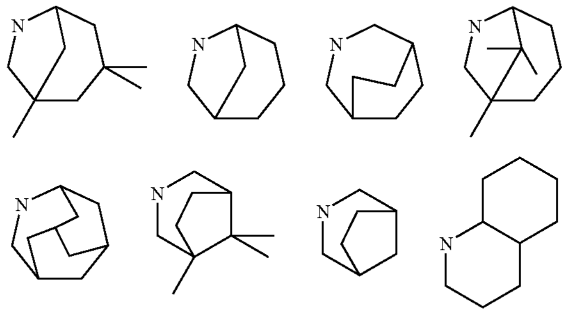

-continued

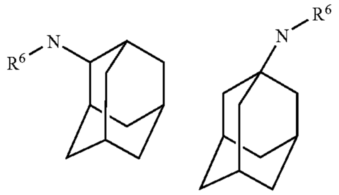

where each carbon is substituted with 0 to 2 $R^{22}$, and $R^{22}$ is independently selected from $C_1$-$C_8$alkyl, halogen, hydroxy, oxo, C(O)$R^{13}$, —S(O)$_2$N$R^7R^8$, —S(O)$_n$$C_1$-$C_4$alkyl and $C_1$-$C_6$alkyloxy.

9. The compound according to any of the preceding clauses, wherein X is —O—.

10. The compound according to any of the preceding clauses, wherein $R^3$ is -1,4-cyclohexyl-$R^9$ or —CH$_2$-1,4-cyclohexyl-$R^9$.

11. The compound according to clause 10, wherein $R^9$ is C(O)$R^{13}$.

12. The compound according to clause 11, wherein $R^{13}$ is hydroxy.

13. The compound according to clause 10, wherein $R^9$ is selected from —CH$_2$—O-aryl, —CH$_2$—O-hetaryl, —O-aryl, —O-hetaryl, —CH$_2$—O—$C_{1-6}$alkyl, —NHC(O)$R^{16}$, where the aryl, hetaryl and $C_{1-6}$alkyl groups are optionally substituted.

14. The compound according to clause 10, wherein $R^9$ is selected from —NH—S(O)$_2$-aryl, —NH—S(O)$_2$-hetaryl, —NH-aryl, —NH-hetaryl, —S(O)$_2$-aryl and —S(O)$_2$-hetaryl, where the aryl and hetaryl groups are optionally substituted.

15. The compound according to any of clauses 1-9, wherein $R^3$ is -1,3-cyclohexyl-$R^9$ or —CH$_2$-1,3-cyclohexyl-$R^9$.

16. The compound according to any of the preceding clauses, wherein $R^3$ comprises a cyclohexyl ring and $R^9$ or $R^{12}$ is attached in the cis-configuration.

17. The compound according to any of clauses 1-15, wherein $R^3$ comprises a cyclohexyl ring and $R^9$ or $R^{12}$ is attached in the trans-configuration.

18. The compound according to any of the clauses 1-9, wherein $R^3$ is -4-piperidin-1-yl-$R^{11}$ or —CH$_2$-4-piperidin-1-yl-$R^{11}$.

19. The compound according to clause 18, wherein $R^{11}$ is selected from aryl, hetaryl, —S(O)$_2$-aryl and —S(O)$_2$-hetaryl, where each aryl and hetaryl groups are optionally substituted.

20. The compound according to any of the clauses 1-9, wherein $R^3$ is -3-piperidin-1-yl-$R^{11}$ or —CH$_2$-3-piperidin-1-yl-$R^{11}$.

21. The compound according to any of clauses 1-6, wherein $R^1$ is hydrogen, $C_1$-$C_4$alkyl or cyclopropyl.

22. The compound according to clause 21, wherein $R^2$ is an unsubstituted adamantyl selected from 1-adamantyl and 2-adamantyl.

23. The compound according to clause 21, wherein $R^2$ is a substituted adamantyl.

24. The compound according to clause 23, wherein $R^2$ is a substituted 1-adamantyl or a substituted 2-adamantyl.

25. The compound according to any of clauses 23-24, wherein $R^2$ is an adamantyl substituted with one, two or more substituents independently selected from halogen, hydroxy, oxo, C(O)$R^{13}$, $C_1$-$C_6$alkyl, $C_1$-$C_6$alkyloxy, —S(O)$_2$N$R^7R^8$, and —S(O)$_n$$C_1$-$C_4$alkyl.

26. The compound according to clauses 1-6, wherein $R^1$ and $R^2$ together with the nitrogen to which they are attached, are forming a substituted 8-aza-bicyclo[3.2.1]octane.

27. The compound according to clause 26, wherein the substituted 8-aza-bicyclo[3.2.1]octane is 8-aza-bicyclo[3.2.1]octan-3-yl.

28. The compound according to clauses 26-27, wherein the substituted 8-aza-bicyclo[3.2.1]octane is substituted with one, two or more substituents independently selected from halogen, hydroxy, oxo, C(O)$R^{13}$, $C_1$-$C_6$alkyl, $C_1$-$C_6$alkyloxy, —S(O)$_2$N$R^7R^8$ and —S(O)$_n$$C_1$-$C_4$alkyl.

29. The compound according to any of the preceding clauses, which is selected from the group consisting of

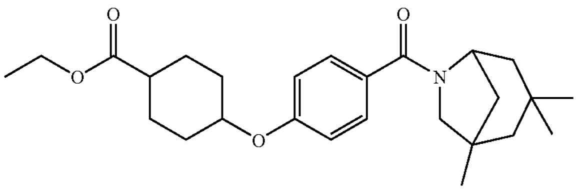

4-[4-1,3,3-Trimethyl-6-aza-bicyclo[3.2.1]octane-6-carbonyl)-phenoxy]-cyclohexane carboxylic acid ethyl ester,

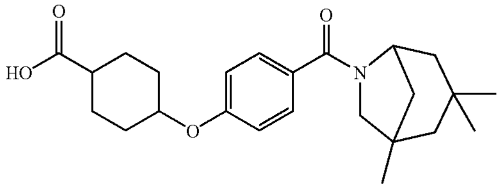

4-[4-(1,3,3-Trimethyl-6-aza-bicyclo[3.2.1]octane-6-carbonyl)-phenoxy]-cyclohexane carboxylic acid,

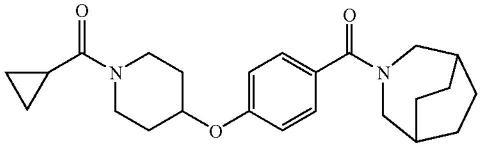

(3-Aza-bicyclo[3.2.2]non-3-yl)-[4-(1-cyclopropanecarbonyl-piperidin-4-yloxy)-phenyl]-methanone,

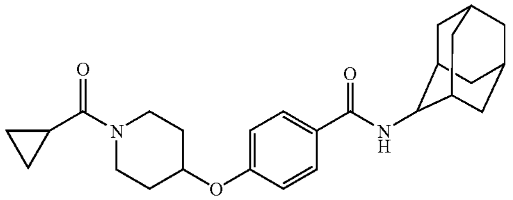

4-(1-Cyclopropanecarbonyl-piperidin-4-yloxy)-N-adamantan-2-yl-benzamide,

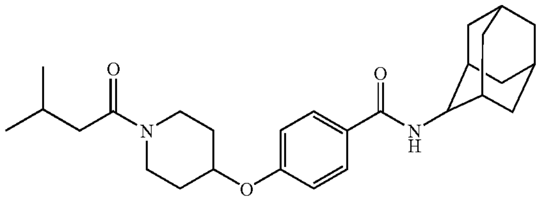

4-[1-(3-Methyl-butyryl)-piperidin-4-yloxy]-N-adamantan-2-yl-benzamide,

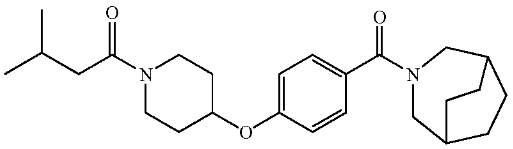

1-[(4-[4-(3-Aza-bicyclo[3.2.2]nonane-3-carbonyl)-phenoxy]-piperidin-1-yl]-3-methyl-butan-1-one,

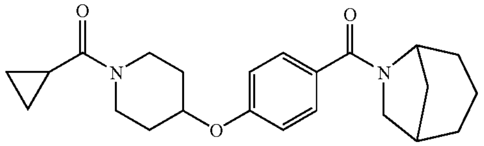

(6-Aza-bicyclo[3.2.1]oct-6-yl)-[4-(1-cyclopropanecarbonyl-piperidin-4-yloxy)-phenyl]-methanone,

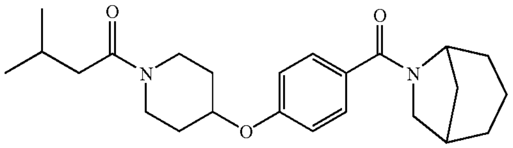

1-{4-[4-(6-Aza-bicyclo[3.2.1]octane-6-carbonyl)-phenoxy]-piperidin-1-yl}-3-methyl-butan-1-one,

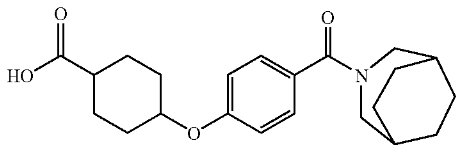

4-[4-(3-Aza-bicyclo[3.2.2]nonane-3-carbonyl)-phenoxy]-cyclohexanecarboxylic acid,

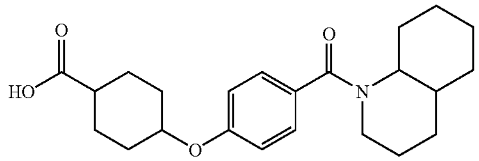

4-[4-(Octahydro-quinoline-1-carbonyl)-phenoxy]-cyclohexanecarboxylic acid,

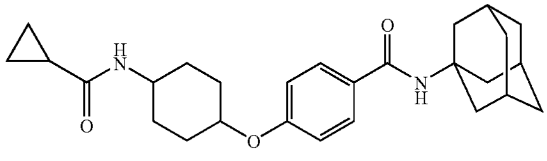

cis/trans-4-[4-(Cyclopropanecarbonyl-amino)-cyclohexyloxy]-N-adamantan-1-yl-benzamide,

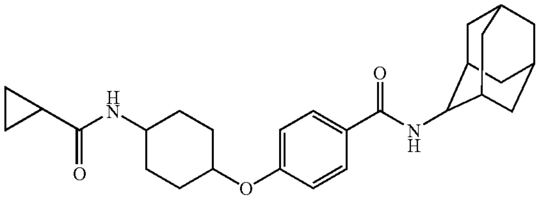

cis/trans-4-[4-(Cyclopropane-carbonyl-amino)-cyclohexyloxy]-N-adamantan-2-yl-benzamide,

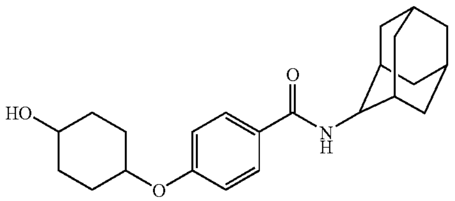

N-Adamantan-2-yl-4-(4-hydroxy-cyclohexyloxy)-benzamide,

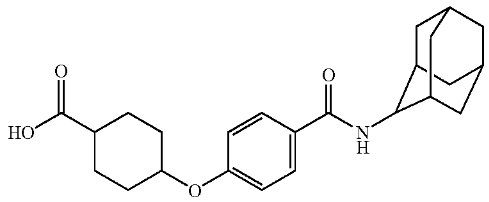

Cis/trans 4-[4-adamantan-2-ylcarbamoyl)-phenoxy]-cyclohexanecarboxylic acid,

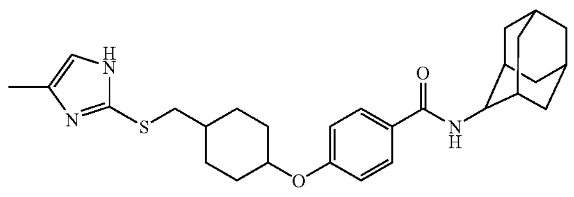

N-Adamantan-2-yl-4-[4-(4-methyl-1H-imidazol-2-ylsulfanylmethyl)-cyclohexyloxy]-benzamide,

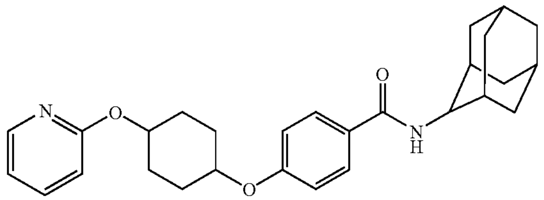

4-[4-(Pyridin-2-yloxy)-cyclohexyloxy]-N-adamantan-2-yl-benzamide,

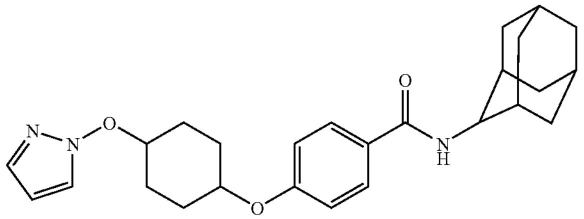

4-[4-(Pyrazol-1-yloxy)-cyclohexyloxy]-N-adamantan-2-yl-benzamide,

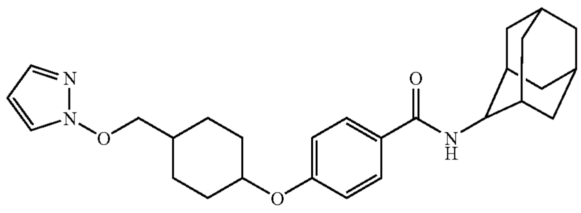

4-[4-(Pyrazol-1-yl-oxymethyl)-cyclohexyloxy]-N-adamantan-2-yl-benzamide,

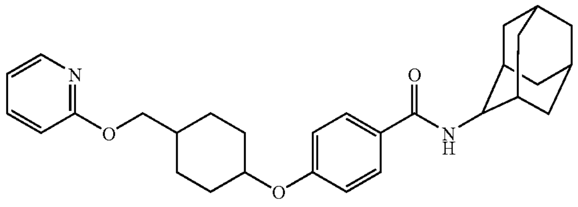

4-[4-(Pyridin-2-yloxymethyl)-cyclohexyloxy]-N-adamantan-2-yl-benzamide,

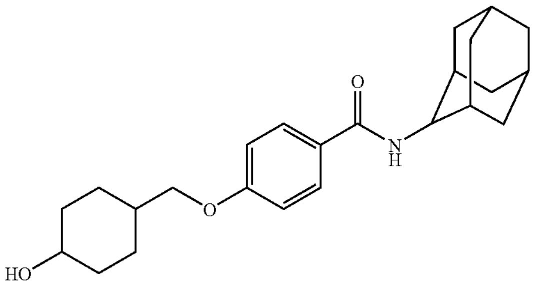

4-(4-Hydroxy-cyclohexyl-methoxy)-N-adamantan-2-yl-benzamide,

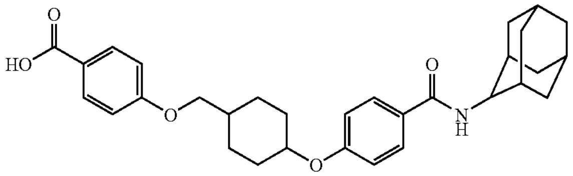

4-{4-[4-(Adamantan-2-yl-carbamoyl)-phenoxy]-cyclohexylmethoxy}-benzoic acid,

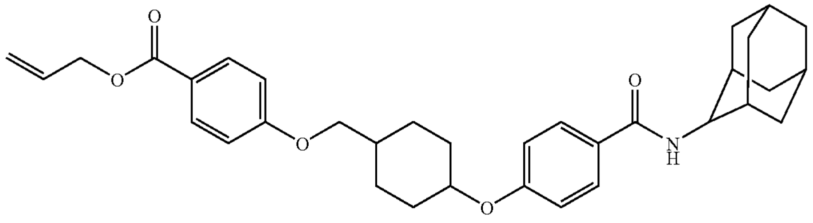

4-{4-[4-(Adamantan-2-yl-carbamoyl)-phenoxy]-cyclohexylmethoxy}-benzoic acid allyl ester,

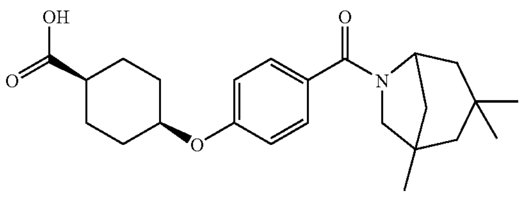

Cis-4-[4-(1,3,3-trimethyl-6-aza-bicyclo[3.2.1]octane-6-carbonyl)-phenoxy]-cyclohexane carboxylic acid,

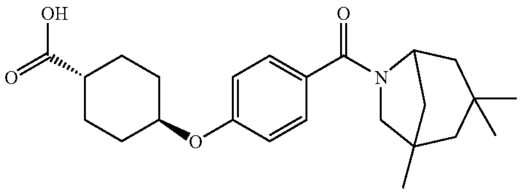

Trans-4-[4-(1,3,3-trimethyl-6-aza-bicyclo[3.2.1]octane-6-carbonyl)-phenoxy]-cyclohexane carboxylic acid,

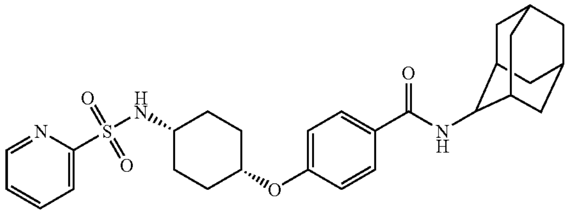

Cis-N-Adamantan-2-yl-4-[4-(pyridine-2-sulfonylamino)-cyclohexyloxy]-benzamide,

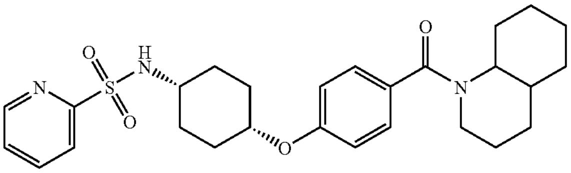

Cis-Pyridine-2-sulfonic acid {4-[4-(octahydro-quinoline-1-carbonyl)-phenoxy]-cyclohexyl}-amide,

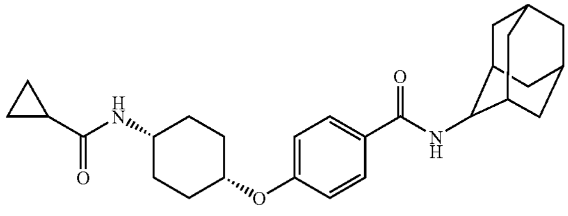

Cis-N-Adamantan-2-yl-4-[4-(cyclopropanecarbonyl-amino)-cyclohexyloxy]-benzamide,

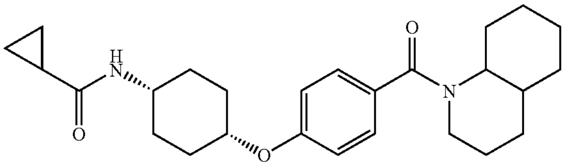

Cis-Cyclopropanecarboxylic acid {4-[4-(octahydro-quinoline-1-carbonyl)-phenoxy]-cyclohexyl}-amide,

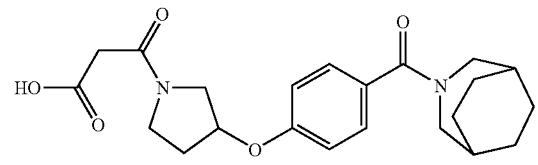

3-{3-[4-(3-Aza-bicyclo[3.2.2]nonane-3-carbonyl)-phenoxy]-pyrrolidin-1-yl}-3-oxo-propionic acid,

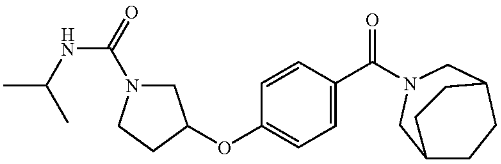

3-[4-(3-Aza-bicyclo[3.2.2]nonane-3-carbonyl)-phenoxy]-pyrrolidine-1-carboxylic acid isopropylamide,

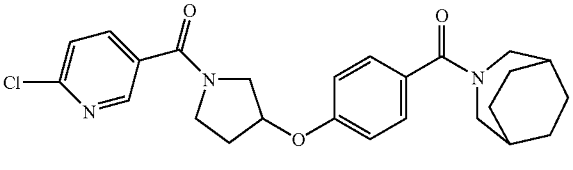

(3-[4-(3-Aza-bicyclo[3.2.2]nonane-3-carbonyl)-phenoxy]-pyrrolidin-1-yl)-(6-chloro-pyridin-3-yl)-methanone,

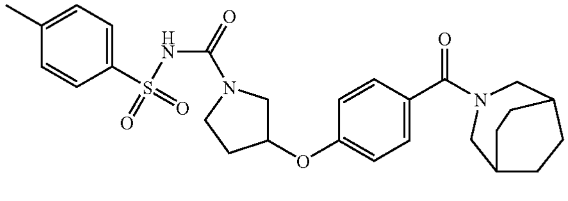

N-{3-[4-(3-Aza-bicyclo[3.2.2]nonane-3-carbonyl)-phenoxy]-pyrrolidine-1-carbonyl}-4-methyl-benzene-sulfonamide,

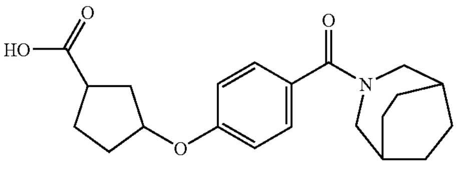

3-[4-(3-Aza-bicyclo[3.2.2]nonane-3-carbonyl)-phenoxy]-cyclopentanecarboxylic acid,

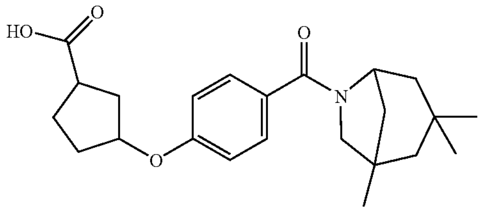

3-[4-(1,3,3-Trimethyl-6-aza-bicyclo[3.2.1]octane-6-carbonyl)-phenoxy]-cyclopentane carboxylic acid,

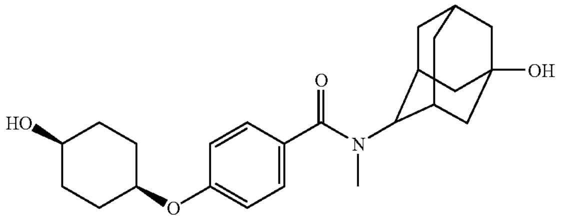

N-(5-Hydroxy-adamantan-2-yl)-4-(4-hydroxy-cyclohexyloxy)-N-methyl-benzamide,

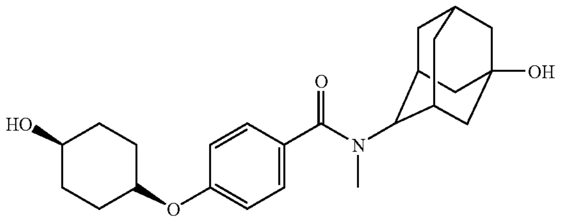

N-(5-Hydroxy-adamantan-2-yl)-4-(4-hydroxy-cyclohexyloxy)-N-methyl-benzamide,

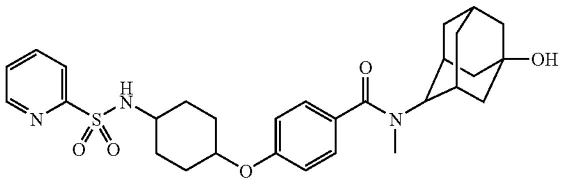

N-(5-Hydroxy-adamantan-2-yl)-N-methyl-4-[4-(pyridine-2-sulfonylamino)-cyclohexyloxy]-benzamide,

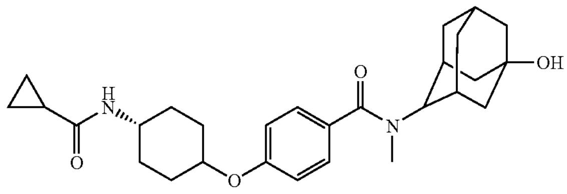

4-[4-(Cyclopropanecarbonyl-amino)-cyclohexyloxy]-N-(5-hydroxy-adamantan-2-yl)-N-methyl-benzamide,

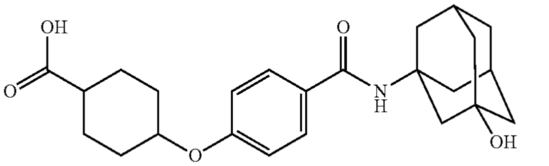

4-[4-(3-Hydroxy-adamantan-1-ylcarbamoyl)-phenoxy]-cyclohexanecarboxylic acid,

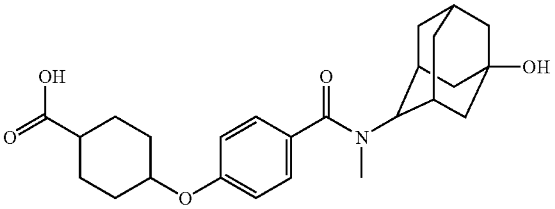

4-{4-[(5-Hydroxy-adamantan-2-yl)-methyl-carbamoyl]-phen-oxy}-cyclohexanecarboxylic acid,

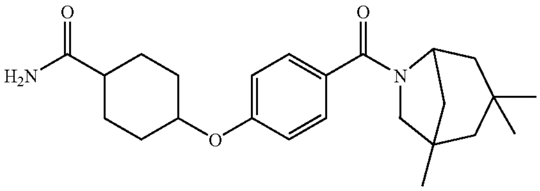

4-[4-(1,3,3-Trimethyl-6-aza-bicyclo[3.2.1]octane-6-carbonyl)-phenoxy]-cyclohexane carboxylic acid amide,

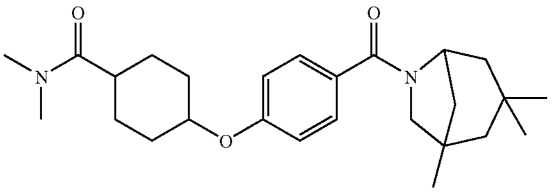

4-[4-(1,3,3-Trimethyl-6-aza-bicyclo[3.2.1]octane-6-carbonyl)-phenoxy]-cyclo-hexane carboxylic acid dimethylamide,

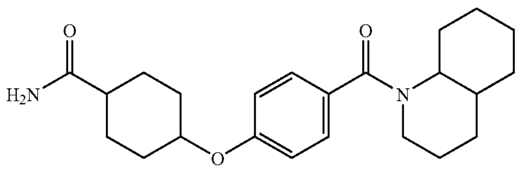

4-[4-(Octahydro-quinoline-1-carbonyl)-phenoxy]-cyclohexanecarboxylic acid amide,

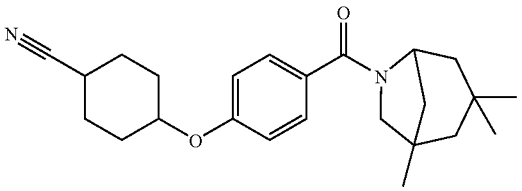

4-[4-(1,3,3-Trimethyl-6-aza-bicyclo[3.2.1]octane-6-carbonyl)-phenoxy]-cyclohexane carbonitrile,

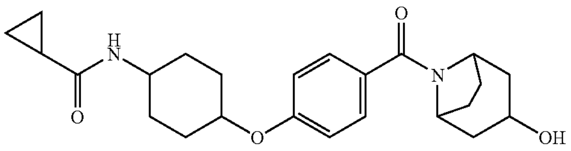

Cyclopropanecarboxylic acid {4-[4-(3-hydroxy-8-aza-bicyclo[3.2.1]octane-8-carbonyl)-phenoxy]-cyclohexyl}-amide,

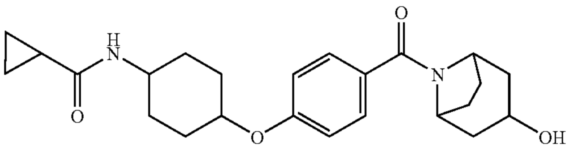

Cyclopropanecarboxylic acid {4-[4-(3-hydroxy-8-aza-bicyclo[3.2.1]octane-8-carbonyl)-phenoxy]-cyclohexyl}-amide,

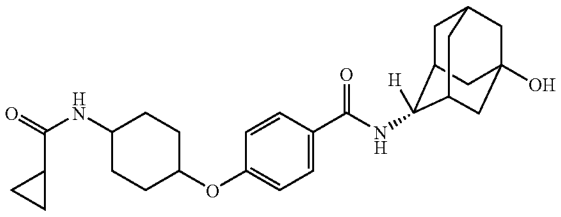

4-[4-(Cyclopropanecarbonyl-amino)cyclohexyloxy]-N-(Z)-(5-hydroxy-adamantan-2-yl)-benzamide,

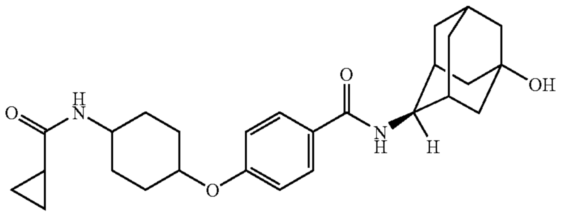

4-[4-(Cyclopropanecarbonyl-amino)-cyclohexyloxy]-N-(E)-(5-hydroxy-adamantan-2-yl)-benzamide,

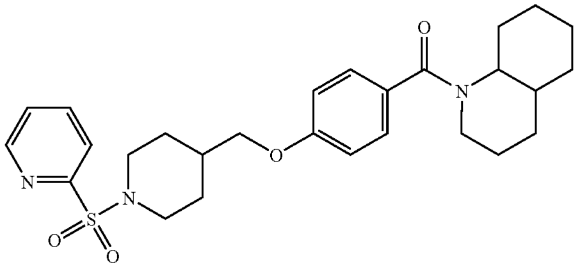

(Octahydro-quinolin-1-yl)-{4-[1-(pyridine-2-sulfonyl)-piperidin-4-ylmethoxy]phenyl}-methanone,

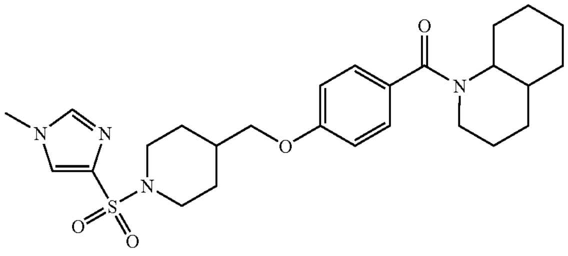

{4-[1-(1-Methyl-1H-imidazole-4-sulfonyl)-piperidin-4-ylmethoxy]-phenyl}-(octahydro-quinolin-1-yl)-methanone,

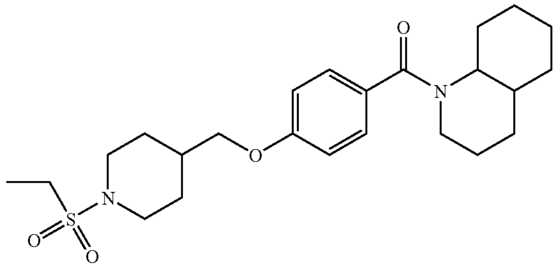

[4-(1-Ethanesulfonyl-piperidin-4-yl-methoxy)-phenyl]-(octahydro-quinolin-1-yl)-methanone,

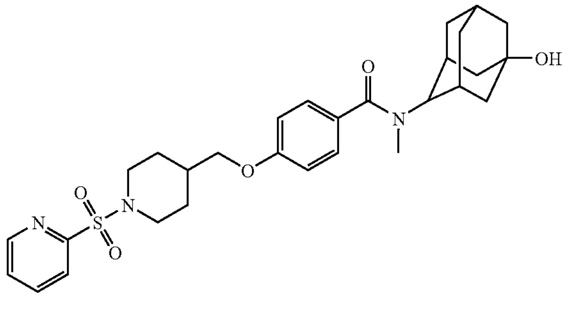

N-(5-Hydroxy-adamantan-2-yl)-N-methyl-4-[1-(pyridine-2-sulfonyl)-piperidin-4-yl-methoxy]-benzamide,

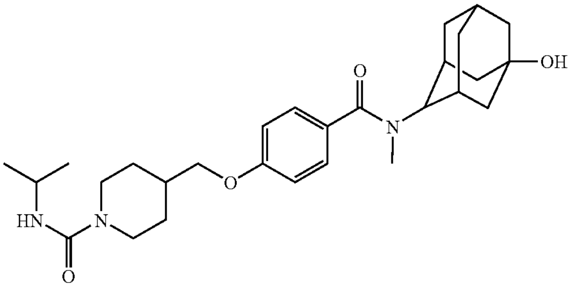

4-{4-[(5-Hydroxy-adamantan-2-yl)-methyl-carbamoyl]-phenoxy-methyl}-piperidine-1-carboxylic acid isopropylamide,

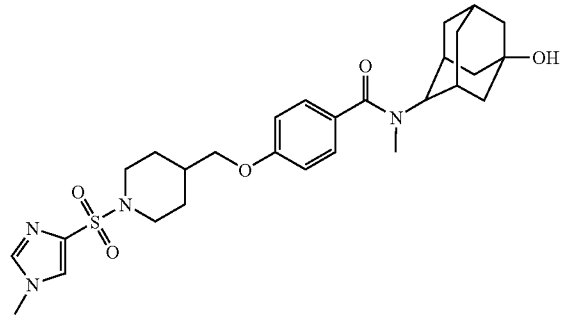

N-(5-Hydroxy-adamantan-2-yl)-N-methyl-4-[1-(1-methyl-1H-imidazole-4-sulfonyl)-piperidin-4-ylmethoxy]-benzamide,

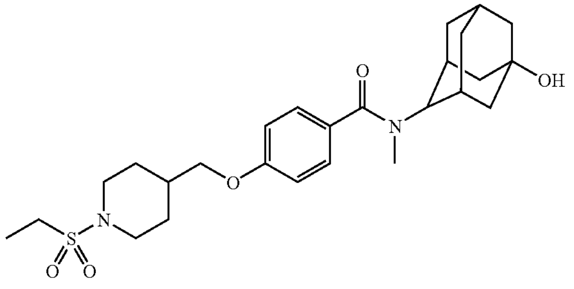

4-(1-Ethanesulfonyl-piperidin-4-ylmethoxy)-N-(5-hydroxy-adamantan-2-yl)-N-methyl-benzamide,

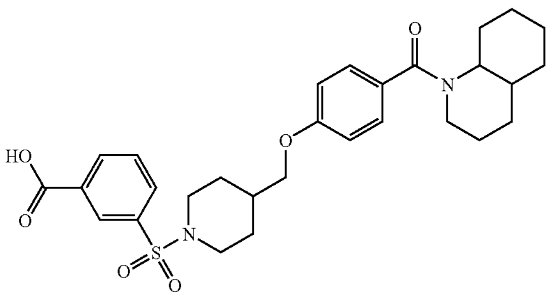

3-{4-[4-(Octahydro-quinoline-1-carbonyl)-phenoxymethyl]-piperidine-1-sulfonyl}-benzoic acid,

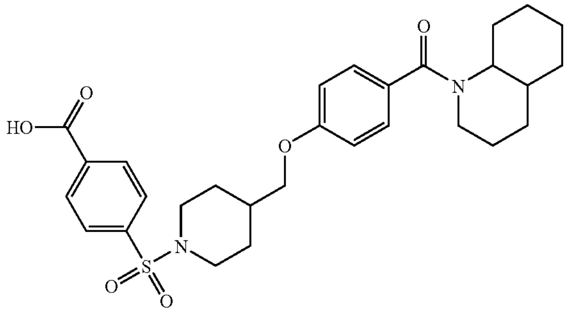

4-{4-[4-(Octahydro-quinoline-1-carbonyl)-phenoxymethyl] piperidine-1-sulfonyl}-benzoic acid,

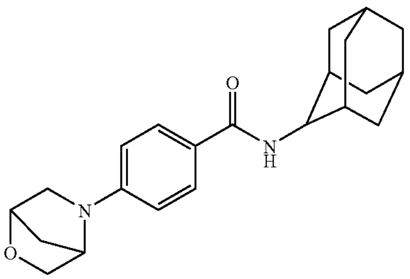

4-(2-Oxa-5-aza-bicyclo[2.2.1]hept-5-yl)-N-adamantan-2-yl-benzamide,

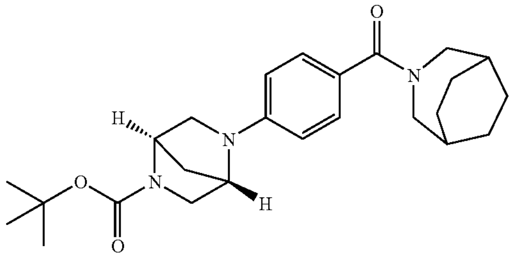

(1S,4S)-5-[4-(3-Aza-bicyclo[3.2.2]nonane-3-carbonyl)-phenyl]-2,5-diaza-bicyclo[2.2.1]heptane-2-carboxylic acid tert-butyl ester,

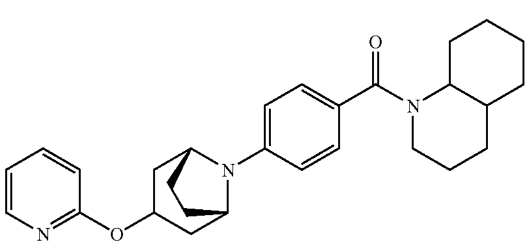

(Octahydro-quinolin-1-yl)-{4-[(1S,5R)-3-(pyridin-2-yloxy)-8-aza-bicyclo[3.2.1]oct-8-yl]-phenyl}-methanone,

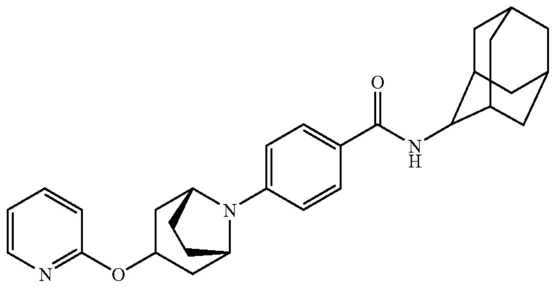

4-[(1S,5R)-3-(Pyridin-2-yloxy)-8-aza-bicyclo[3.2.1]oct-8-yl]-N-adamantan-2-yl-benzamide; or a prodrug thereof, a salt thereof with a pharmaceutically acceptable acid or base, or any optical isomer or mixture of optical isomers, including a racemic mixture, or any tautomeric forms.

30. The compound according to any one of the preceding clauses, wherein polar surface area (PSA) of said compound is in the range from 40 $Å^2$ to 130 $Å^2$, preferably from 50 $Å^2$ to 130 $Å^2$, more preferably from 60 $Å^2$ to 120 $Å^2$, more preferably from 70 $Å^2$ to 120 $Å^2$, most preferable from 70 $Å^2$ to 110 $Å^2$.

31. The compound according to any one of the preceding clauses, wherein the molar weight of said compound is in the range from 350 D to 650 D, preferably from 400 D to 600 D.

32. The compound according to any one of the preceding clauses, which is an agent useful for the treatment, prevention and/or prophylaxis of any conditions, disorders and diseases wherein a modulation or an inhibition of the activity of 11βHSD1 is beneficial.

33. The compound according to any one of the clauses 1-29, which is an agent useful for the treatment, prevention and/or prophylaxis of any conditions, disorders and diseases that are influenced by intracellular glucocorticoid levels.

34. The compound according to any one of the clauses 1-29 which is an agent useful for the treatment, prevention and/or prophylaxis of conditions, disorders or diseases selected from the group consisting of the metabolic syndrome, insulin resistance, dyslipidemia, hypertension and obesity.

35. The compound according to any one of the clauses 1-29 which is an agent useful for the treatment, prevention and/or prophylaxis of type 2 diabetes, impaired glucose tolerance (IGT), impaired fasting glucose (IFG).

36. The compound according to any one of the clauses 1-29 which is an agent useful for the delaying or prevention of the progression from IGT into type 2 diabetes.

37. The compound according to any one of the clauses 1-29 which is an agent useful for delaying or prevention of the progression of the metabolic syndrome into type 2 diabetes.

38. The compound according to any one of the clauses 1-29 which is an agent useful for the treatment, prevention and/or prophylaxis of adverse effects of glucocorticoid receptor agonist treatment or therapy.

39. A pharmaceutical composition comprising, as an active ingredient, at least one compound according to any one of the clauses 1-29 together with one or more pharmaceutically acceptable carriers or excipients.

40. The pharmaceutical composition according to clause 39 which is for oral, nasal, buccal, transdermal, pulmonal or parenteral administration.

41. The pharmaceutical composition according to clause 39 or 40 in unit dosage form, comprising from 0.05 mg to 2000 mg/day, from 0.1 mg to 1000 mg or from 0.5 mg to 500 mg per day of the compound according to anyone of the clauses 1-29.

42. Use of a compound according to any of the clauses 1-29, for the preparation of a pharmaceutical composition for the treatment, prevention and/or prophylaxis of any conditions, disorders and diseases wherein a modulation or an inhibition of the activity of 11βHSD1 is beneficial.

43. Use of a compound according to any of the clauses 1-29, for the preparation of a pharmaceutical composition for the treatment, prevention and/or prophylaxis of any conditions, disorders and diseases that are influenced by intracellular glucocorticoid levels.

44. Use of a compound according to any of the clauses 1-29, for the preparation of a pharmaceutical composition for the treatment, prevention and/or prophylaxis of conditions, disorders or diseases selected from the group consisting of the metabolic syndrome, insulin resistance, dyslipidemia, hypertension and obesity.

45. Use of a compound according to any of the clauses 1-29, for the preparation of a pharmaceutical composition for the treatment, prevention and/or prophylaxis of type 2 diabetes, impaired glucose tolerance (IGT), impaired fasting glucose (IFG).

46. Use of a compound according to any of the clauses 1-29, for the preparation of a pharmaceutical composition for the delaying or prevention of the progression from IGT to type 2 diabetes.

47. Use of a compound according to any of the clauses 1-29, for the preparation of a pharmaceutical composition for the delaying or prevention of the progression of the metabolic syndrome into type 2 diabetes.

48. Use of a compound according to any of the clauses 1-29, for the preparation of a pharmaceutical composition for the treatment, prevention and/or prophylaxis of adverse effects of glucocorticoid receptor agonist treatment or therapy.

49. A method for the treatment, prevention and/or prophylaxis of any conditions, disorders or diseases wherein a modulation or an inhibition of the activity of 11βHSD1 is beneficial, the method comprising administering to a subject in need thereof an effective amount of a compound according to the invention.

50. The method according to clause 49 wherein the conditions, disorders or diseases are selected from the group consisting of the metabolic syndrome, insulin resistance, dyslipidemia, hypertension and obesity.

The invention claimed is:

1. A compound of Formula (I) or a pharmaceutically acceptable salt thereof:

(I)

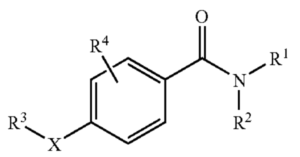

wherein:

$R^1$ is hydrogen, $C_1$-$C_4$alkyl, or cyclopropyl;

$R^2$ is adamantyl optionally substituted with 0 to 1 $R^{18}$;

$R^4$ is hydrogen, $C_1$-$C_4$alkyl, trifluoromethyl, halogen, $C_1$-$C_4$alkyloxy, $C_1$-$C_4$alkyloxy$C_1$-$C_4$alkyl, or $C_1$-$C_4$alkylcarbonyl, wherein the alkyl portion of each is substituted with 0 to 1 $R^{18}$;

X is —O—;

$R^3$ is -1,4-cyclohexyl-$R^9$, —$CH_2$-1,4-cyclohexyl-$R^9$, -4-piperidin-1-yl-$R^{11}$, or —$CH_2$-4-piperidin-1-yl-$R^{11}$;

$R^9$ is hydroxy, cyano, $C(O)R^{13}$, —$(CR^{14}R^{15})_n C(O)NR^7R^8$, —$(CR^{14}R^{15})_n NHC(O)R^{16}$, —$(CR^{14}R^{15})_n OR^{16}$, —$(CR^{14}R^{15})_n S(O)_m R^{16}$, —$(CR^{14}R^{15})_n S(O)_2 NR^7R^8$, —$(CR^{14}R^{15})_n NR^7R^8$, —$(CR^{14}R^{15})_n NR^{17}C(O)NR^7R^8$, —$(CR^{14}R^{15})_n NR^{17}S(O)_2R^{16}$, —$(CR^{14}R^{15})_n C{=}C$—$R^{16}$, —$(CR^{14}R^{15})_n C{\equiv}C$—$R^{16}$, —$(CR^{14}R^{15})_n$ aryl substituted with 0 to 2 $R^{20}$, or —$(CR^{14}R^{15})_n$hetaryl optionally substituted with 0 to 2 $R^{19}$;

$R^{11}$ is —$C(O)NR^7R^8$, —$CH_2C(O)NR^7R^8$, —$C(O)R^{17}$, —$S(O)_2R^{16}$ or —$S(O)_2NR^7R^8$;

$R^{13}$ is hydroxy, $C_1$-$C_6$alkyl, $C_1$-$C_6$alkenyl, $C_1$-$C_6$alkynyl, cycloalkyl, $C_1$-$C_6$alkyloxy, aryl, aryloxy, aryl$C_1$-$C_6$alkyloxy, hetaryl, hetaryloxy or hetaryl$C_1$-$C_6$alkyloxy, wherein the $C_1$-$C_6$alkyl, cycloalkyl, aryl and hetaryl groups are optionally substituted with one or more $R^{19}$;

$R^{14}$ and $R^{15}$ independently are hydrogen, halogen, $C_1$-$C_6$alkyl or cycloalkyl, wherein each is optionally substituted with 0 to 2 substituents selected independently from the group consisting of halogen, hydroxyl, and oxo;

or $R^{14}$ and $R^{15}$, together with the carbon atom to which they are attached, form a cycloalkyl ring;

$R^{16}$ is hydrogen, $C_1$-$C_6$alkyl, $C_1$-$C_6$alkenyl, $C_1$-$C_6$alkynyl, cycloalkyl, hetcycloalkyl, aryl, or hetaryl, wherein the $C_1$-$C_6$alkyl, cycloalkyl, aryl and hetaryl groups are each optionally substituted with one or more $R^{19}$;

$R^{17}$ is hydrogen, $C_1$-$C_6$alkyl, $C_1$-$C_6$alkyl$C(O)R^{20}$, —$(CR^{14}R^{15})_n NR^{17}S(O)_2R^{16}$, cycloalkyl, hetcycloalkyl, aryl, or hetaryl, wherein the alkyl, cycloalkyl, hetcycloalkyl, aryl and hetaryl groups are each optionally are substituted with one or more $R^{21}$;

$R^{18}$ is halogen, hydroxy, oxo, —$S(O)_2C_1$-$C_4$alkyl, —$S(O)_2NR^7R^8$ or —$C(O)R^{13}$;

$R^{19}$ is halogen, hydroxy, oxo, —$C(O)R^{20}$, $C_1$-$C_6$alkyl$C(O)R^{20}$, —$S(O)_nR^{16}$, —$S(O)_nNR^7R^8$, cyclopropyl, —$OR^{16}$, $C_1$-$C_6$alkyl, aryl, hetaryl, —$NR^{22}C(O)NR^7R^8$, —$NR^{22}S(O)_2NR^7R^8$, or —$NC(O)NHS(O)_2R^{16}$;

$R^{20}$ is hydroxy, $C_1$-$C_6$alkyl, $C_1$-$C_6$alkenyl, $C_1$-$C_6$alkynyl, cycloalkyl, $C_1$-$C_6$alkyloxy, aryl, aryloxy, aryl$C_1$-$C_6$alkyloxy, hetaryl, hetaryloxy or hetaryl$C_1$-$C_6$alkyloxy;

$R^{21}$ is halogen, cyano or hydroxy; and m and n independently are 0, 1 or 2.

2. The compound of claim 1, wherein $R^3$ is -1,4-cyclohexyl-$R^9$ or —$CH_2$-1,4-cyclohexyl-$R^9$.

3. The compound of claim 2, wherein $R^9$ is $C(O)R^{13}$.

4. The compound of claim 3, wherein $R^{13}$ is hydroxy.

5. The compound of claim 2, wherein $R^9$ is selected from —$CH_2$—O-aryl, —$CH_2$—O-hetaryl, —O-aryl, —O-hetaryl, —$CH_2$—O—$C_{1-6}$alkyl, or —$NHC(O)R^{16}$, wherein the aryl, hetaryl, and alkyl groups are each optionally substituted with one or more $R^{19}$.

6. The compound of claim 2, wherein $R^9$ is —NH—$S(O)_2$-aryl, —NH—$S(O)_2$-hetaryl, —NH-aryl, —NH-hetaryl, —$S(O)_2$-aryl, or —$S(O)_2$-hetaryl, where the aryl and hetaryl groups are each optionally substituted with one or more $R^{19}$.

7. The compound of claim 1, wherein $R^3$ is -4-piperidin-1-yl-$R^{11}$, or —$CH_2$-4-piperidin-1-yl-$R^{11}$.

8. A compound selected from the group consisting of:

4-(1-Cyclopropanecarbonyl-piperidin-4-yloxy)-N-adamantan-2-yl-benzamide;

4-[1-(3-Methyl-butyryl)-piperidin-4-yloxy]-N-adamantan-2-yl-benzamide;

4-[4-(Cyclopropanecarbonyl-amino)-cyclohexyloxy]-N-adamantan-1-yl-benzamide;

4-[4-(Cyclopropane-carbonyl-amino)-cyclo-hexyloxy]-N-adamantan-2-yl-benzamide;

N-Adamantan-2-yl-4-(4-hydroxy-cyclohexyloxy)-benzamide;

4-[4-adamantan-2-ylcarbamoyl)-phenoxy]-cyclohexanecarboxylic acid;

N-Adamantan-2-yl-4-[4-(4-methyl-1H-imidazol-2-ylsulfanylmethyl)-cyclohexyloxy]-benzamide;

4-[4-(Pyridin-2-yloxy)-cyclohexyloxy]-N-adamantan-2-yl-benzamide;

4-[4-(Pyrazol-1-yloxy)-cyclohexyloxy]-N-adamantan-2-yl-benzamide;

4-[4-(Pyrazol-1-yl-oxymethyl)-cyclohexyloxy]-N-adamantan-2-yl-benzamide;

4-[4-(Pyridin-2-yloxymethyl)-cyclohexyloxy]-N-adamantan-2-yl-benzamide;

4-(4-Hydroxy-cyclohexyl-methoxy)-N-adamantan-2-yl-benzamide;

4-{4-[4-(Adamantan-2-yl-carbamoyl)-phenoxy]-cyclohexylmethoxy}-benzoic acid;

4-{4-[4-(Adamantan-2-yl-carbamoyl)-phenoxy]-cyclohexylmethoxy}-benzoic acid allyl ester;

Cis-N-Adamantan-2-yl-4-[4-(pyridine-2-sulfonylamino)-cyclohexyloxy]-benzamide;

Cis-Pyridine-2-sulfonic acid {4-[4-(octahydro-quinoline-1-carbonyl)-phenoxy]-cyclohexyl}-amide;

Cis-N-Adamantan-2-yl-4-[4-(cyclopropanecarbonyl-amino)-cyclohexyloxy]-benzamide;

N-(5-Hydroxy-adamantan-2-yl)-4-(4-hydroxy-cyclohexyl-oxy)-N-methyl-benzamide;

N-(5-Hydroxy-adamantan-2-yl)-4-(4-hydroxy-cyclohexyl-oxy)-N-methyl-benzamide;

N-(5-Hydroxy-adamantan-2-yl)-N-methyl-4-[4-(pyridine-2-sulfonylamino)-cyclohexyloxy]-benzamide;

4-[4-(Cyclopropanecarbonyl-amino)-cyclohexyloxy]-N-(5-hydroxy-adamantan-2-yl)-N-methyl-benzamide;

4-[4-(3-Hydroxy-adamantan-1-ylcarbamoyl)-phenoxy]-cyclohexanecarboxylic acid;

4-{4-[(5-Hydroxy-adamantan-2-yl)-methyl-carbamoyl]-phen-oxy}-cyclohexanecarboxylic acid;

4-[4-(Cyclopropanecarbonyl-amino)-cyclohexyloxy]-N-(Z)-(5-hydroxy-adamantan-2-yl)-benzamide;

4-[4-(Cyclopropanecarbonyl-amino)-cyclohexyloxy]-N-(E)-(5-hydroxy-adamantan-2-yl)-benzamide;

N-(5-Hydroxy-adamantan-2-yl)-N-methyl-4-[1-(pyridine-2-sulfonyl)-piperidin-4-yl-methoxy]-benzamide;

4-{4-[(5-Hydroxy-adamantan-2-yl)-methyl-carbamoyl]-phenoxy-methyl}-piperidine-1-carboxylic acid isopropylamide;

N-(5-Hydroxy-adamantan-2-yl)-N-methyl-4-[1-(1-methyl-1H-imidazole-4-sulfonyl)-piperidin-4-yl-methoxy]-benzamide; and 4-(1-Ethanesulfonyl-piperidin-4-ylmethoxy)-N-(5-hydroxy-adamantan-2-yl)-N-methyl-benzamide;

or a pharmaceutically acceptable salt thereof.

9. A pharmaceutical composition comprising a compound of claim 1 and a pharmaceutically acceptable carrier or excipient.

10. A pharmaceutical composition comprising a compound of claim 8 and a pharmaceutically acceptable carrier or excipient.

* * * * *